US010400013B2

(12) United States Patent
Liao et al.

(10) Patent No.: US 10,400,013 B2
(45) Date of Patent: Sep. 3, 2019

(54) FUSION POLYPEPTIDE FOR IMMUNO-ENHANCEMENT AND METHOD FOR ENHANCING STIMULATION OF IMMUNE RESPONSE USING THE SAME

(71) Applicants: Chao-Wei Liao, Hsinchu (TW); Chung-Chin Chen, Alexandria, VA (US)

(72) Inventors: Chao-Wei Liao, Hsinchu (TW); Ting-Kai Liao, Hsinchu (TW)

(73) Assignee: Chao-Wei Liao, Hsinchu (TW)

( * ) Notice: Subject to any disclaimer, the term of this patent is extended or adjusted under 35 U.S.C. 154(b) by 0 days.

(21) Appl. No.: 15/794,211

(22) Filed: Oct. 26, 2017

(65) Prior Publication Data

US 2018/0111964 A1 Apr. 26, 2018

Related U.S. Application Data

(60) Provisional application No. 62/412,896, filed on Oct. 26, 2016.

(51) Int. Cl.

| | |
|---|---|
| ***A61K 39/00*** | (2006.01) |
| ***A61K 39/12*** | (2006.01) |
| ***C07K 14/005*** | (2006.01) |
| ***C07K 7/08*** | (2006.01) |
| ***C07K 14/475*** | (2006.01) |
| ***C12N 9/10*** | (2006.01) |
| ***C07K 14/21*** | (2006.01) |
| *A61P 31/20* | (2006.01) |
| *A61P 31/14* | (2006.01) |

(52) U.S. Cl.

CPC ............ *C07K 7/08* (2013.01); *A61K 39/0005* (2013.01); *A61K 39/00113* (2018.08); *A61K 39/12* (2013.01); *C07K 14/005* (2013.01); *C07K 14/21* (2013.01); *C07K 14/475* (2013.01); *C12N 9/1077* (2013.01); *C12Y 204/02036* (2013.01); *A61K 2039/542* (2013.01); *A61K 2039/55544* (2013.01); *A61K 2039/55555* (2013.01); *A61K 2039/57* (2013.01); *A61K 2039/6037* (2013.01); *A61K 2039/70* (2013.01); *A61P 31/14* (2018.01); *A61P 31/20* (2018.01); *C07K 2319/01* (2013.01); *C07K 2319/10* (2013.01); *C07K 2319/33* (2013.01); *C07K 2319/40* (2013.01); *C12N 2710/20034* (2013.01); *C12N 2710/20071* (2013.01); *C12N 2770/10034* (2013.01); *C12N 2770/10071* (2013.01)

(58) Field of Classification Search

None

See application file for complete search history.

(56) References Cited

U.S. PATENT DOCUMENTS

| | | | | |
|---|---|---|---|---|
| 7,485,321 | B2 | 2/2009 | O'Mahony et al. | |
| 8,372,407 | B2 | 2/2013 | Liao et al. | |
| 2002/0127234 | A1 | 9/2002 | El Halawani et al. | |
| 2004/0247617 | A1* | 12/2004 | Liao .................... | C07K 14/005 424/192.1 |

OTHER PUBLICATIONS

Challa et al. Bacterial Toxin Fusion Proteins Elicit Mucosal Immunity against a Foot-and-Mouth Disease Virus Antigen When Administered Intranasally to Guinea Pigs. Advances in Virology. vol. 2011, Article ID 713769, 11 pages.*

Kim et al. The M Cell-Targeting Ligand Promotes Antigen Delivery and Induces Antigen-Specific Immune Responses in Mucosal Vaccination. J Immunol 2010; 185:5787-5795.*

Sae-Hae Kim, Ki-Weon Seo, Ju Kim, Kyung-Yeol Lee, and Yong-Suk Jang, The M Cell-Targeting Ligand Promotes Antigen Delivery and Induces Antigen-Specific Immune Responses in Mucosal Vaccination, J Immunol 2010; 185:5787-5795.

Ali Azizi, Ashok Kumar, Francisco Diaz-Mitoma and Jiri Mestecky, Enhancing Oral Vaccine Potency by Targeting Intestinal M Cells, PLoS Pathogens, Nov. 2010, vol. 6, Issue 11.

K J Syrjänen, HPV Infections and Oesophageal Cancer, J Clin Pathol 2002;55:721-728.

Roy C. Orlando, M.D., Esophageal Mucosal Defense Mechanisms, GI Motility online (2006).

Daniel J. Mulder, David Lobo, Nanette Mak and Christopher J. Justinich, Expression of Toll-Like Receptors 2 and 3 on Esophageal Epithelial Cell Lines and on Eosinophils During Esophagitis, Mar. 2012, vol. 57, Issue 3, pp. 630-642.

Joshua W.Wang and RichardB.S.Roden, L2, The Minor Capsid Protein of Papillomavirus, Virology 445(2013) 175-186.

Asis K. Sarkar, Guillermo Tortolero-Luna, Michele Follen, K. Jagannadha Sastry, Inverse correlation of cellular immune responses specific to synthetic peptides from the E6 and E7 oncoproteins of HPV-16 with recurrence of cervical intraepithelial neoplasia in a cross-sectional study, Gynecologic Oncology 99 (2005) S251-S261.

R. W. Tindle, S. Croft, K. Herd, K. Malcolm, A. F. Geczy, T. Stewart and G. J. P. Fernando, A vaccine conjugate of 'ISCAR' immunocarrier and peptide epitopes of the E7 cervical cancer-associated protein of human papillomavirus type 16 elicits specific Thl- and Th2-type responses in immunized mice in the absence of oil-based adjuvants, Clin Exp Immunol 1995; 101:265-271.

Mark W. Hamrick,Myostatin (GDF-8) as a Therapeutic Target for the Prevention of Osteoporotic Fractures, IBMS BoneKEy. Jan. 2010;7(1):8-17.

O. J. Lopez,M. F. Oliveira,E. Alvarez Garcia, B. J. Kwon, A. Doster, and F. A. Osorio, Protection against Porcine Reproductive and Respiratory Syndrome Virus (PRRSV) Infection through Passive Transfer of PRRSV-Neutralizing Antibodies Is Dose Dependent, Clinical and Vaccine Immunology, Mar. 2007, p. 269-275.

(Continued)

*Primary Examiner* — Nianxiang Zou

(74) *Attorney, Agent, or Firm* — Bacon & Thomas, PLLC

(57) ABSTRACT

A fusion polypeptide is disclosed, which includes: (a) a mucosa targeting polypeptide; (b) a translocating peptide for translocation; and (c) a antigenic epitope. In addition, a method for enhancing a stimulation of an immune response using the aforementioned fusion polypeptide is also disclosed.

33 Claims, No Drawings

Specification includes a Sequence Listing.

(56) References Cited

OTHER PUBLICATIONS

C.-W. Liao, T.-H. Hseu J. Hwang, A target-specific chimeric toxin composed of epidermal growth factor and Pseudomonas exotoxin A with a deletion in its toxin-binding domain, Appl Microbiol Biotechnol (1995) 43:498-507.
Suiyang Li, Sylvie Labrecque, M Cristina Gauzzi, Andrew R Cuddihy, Andrew HT Wong, Sandra Pellegrini, Gregory J Matlashewski and Antonis E Koromilas,The human papilloma virus (HPV)-18 E6 oncoprotein physically associates with Tyk2 and impairs Jak-STAT activation by interferon-a, Oncogene (1999) 18, 5727-5737.
Masaud Shah, Muhammad Ayaz Anwar, Seolhee Park, Syyada Samra JAFRI2 and Sangdun Choi , In silico mechanistic analysis of IRF3 inactivation and high-risk HPV E6 species-dependent drug response, Scientific Reports,5:13446.
Wen-Fang Cheng, Ming-Cheng Chang, Wei-Zen Sun, Yu-Wei Jen, Chao-Wei Liao, Yun-Yuan Chen, and Chi-An Chen, Fusion Protein Vaccines Targeting Two Tumor Antigens Generate Synergistic Anti-Tumor Effects, PLoS One, Sep. 2013, vol. 8, Issue 9.
Young-Sik Cho, Jeong-Woo Kang, Minchul Cho, Cheong-Weon Cho, Shinje Lee, Yong-Kyung Choe, Yongman Kim, Inpyo Choi, Sue-Nie Park, Soohyun Kim, Charles A. Dinarello and Do-Young Yoon, Down modulation of IL-18 expression by human papillomavirus type 16 E6 oncogene via binding to IL-18, FEBS Letters 501 (2001) 139-145.
Sedighe Ebrahimpoor, Saeed-Reza Pakzad, and Soheila Ajdary, IgG1 and IgG2a Profile of Serum Antibodies to Leishmania major Amastigote in BALB/c and C57BL/6Mice, Original Article Iran J Allergy Asthma ImmunolDec. 2013; 12(4):361-367.
Chao-Wei Liao, Chi-An Chen, Chien-Nan Lee, Yi-Ning Su,Ming-Cheng Chang, Ming-Houg Syu, Chang-Yao Hsieh, and Wen-Fang Cheng, Fusion Protein Vaccine by Domains of Bacterial Exotoxin Linked with a Tumor Antigen Generates Potent Immunologic Responses and Antitumor Effects, Cancer Res 2005; 65: (19). Oct. 1, 2005.
Joao-Paulo G. Camporez, Max C. Petersen, Abulizi Abudukadier, Gabriela V. Moreira, Michael J. Jurczak,Glenn Friedman, Christopher M. Haqq, Kitt Falk Petersen, and Gerald I. Shulman, Anti-myostatin antibody increases muscle mass and strength and improves insulin sensitivity in old mice, 2212-2217, PNAS,Feb. 23, 2016, vol. 113,No. 8.
Tingting Zhang, Lin Sun, Ying Xin, Lixia Ma, Youyou Zhang, Xin Wang, Kun Xu, Chonghua Ren, Cunfang Zhang, Zhilong Chen, Hanjiang Yang and Zhiying Zhang, A vaccine grade of yeast *Saccharomyces cerevisiae* expressing mammalian myostatin, Zhang et al. BMC Biotechnology 2012, 12:97.
S. Aravind, B.R. Patil, Sohini Dey, C. Madhan Mohan, Recombinant UL30 antigen-based single serum dilution ELISA for detection of duck viral enteritis, Journal of Virological Methods 185 (2012) 234-238.
O. J. Lopez, M. F. Oliveira, E. Alvarez Garcia, B. J. Kwon, A. Doster and F. A. Osorio, Protection against Porcine Reproductive and Respiratory Syndrome Virus (PRRSV) Infection through Passive Transfer of PRRSV-Neutralizing Antibodies Is Dose Dependent, Clinical and Vaccine Immunology, Mar. 2007, p. 269-275, vol. 14, No. 3.
Sreerupa Challa, Stevenm. Szczepanek, Debra Rood,Rogerw. Barrette, and Lawrence K. Silbart, Bacterial Toxin Fusion Proteins ElicitMucosal Immunity against a Foot-and-Mouth Disease Virus Antigen When Administered Intranasally to Guinea Pigs, Hindawi Publishing Corporation Advances in Virology vol. 2011, Article ID 713769, 11 pages.

* cited by examiner

FUSION POLYPEPTIDE FOR IMMUNO-ENHANCEMENT AND METHOD FOR ENHANCING STIMULATION OF IMMUNE RESPONSE USING THE SAME

CROSS REFERENCE TO RELATED APPLICATION

This application claims the benefit of filing date of U.S. Provisional Application Ser. No. 62/412,896, filed Oct. 26, 2016 under 35 USC § 119(e)(1).

BACKGROUND

1. Field

The present disclosure relates to a fusion polypeptide, a composition comprising the same and a method for enhancing a stimulation of an immune response using the same.

2. Description of Related Art

Over 35 years, the antigenic peptides are critical factors in mobilizing the immune system against foreign invaders and cancers. Most of the highly successful treatments, including vaccines, have been made empirically, with little immunological insight. Until 1986, it was never considered that peptides could have an essential role in the control of the specificity of immune responses in conjunction with molecules—MHC class I and II—best known for their involvement in transplant rejection. However, new knowledge about the chemistry and pharmacological properties of antigenic peptides as well as of the molecular biology of antigen processing, presentation, and recognition by immune cells, has now enabled a more rational approach to vaccine and immune enhancer design. Harnessing the immune system to treat disease or cancer therapy will be facilitated by a greater understanding of the origins and roles of antigenic peptides in immunity The roles of antigenic peptides in both the innate and adaptive immune systems are these key players can be used for therapy against infectious disease, cancer and autoimmune conditions. Innate immunity is the first line shotgun approach of defense against infections and is exemplified by antimicrobial peptides, also known as host defense peptides (HDPs). Adaptive immunity relies on the capacity of immune cells to distinguish between the body's own antigens and unwanted invaders and tumor cells. The antigen peptide belonging to the type of adaptive immunity, there is a path of the molecule from initial generation by proteolytic processing to its presentation to immune cells by major histocompatibility complex (MHC) molecules in immune system. Therefore, key players are MHC-I and MHC-II that form a noncovalent complex with antigen peptides and present these peptides in the context of antigen-presenting cells to T cells of the immune system Although the antigenic peptides are known to be an effective manner for stimulating immune response, many researches and studies still focus on finding novel antigenic peptides with improved effect. Therefore, an object of the present disclosure is to find an adjuvant, which can effectively transport to immune target organs for adaptive immunity route to achieve the purpose of enhancing the stimulation of the immune response.

SUMMARY

The present disclosure provides a fusion polypeptide, which can be used as an enhancer for stimulating the immune response.

The present disclosure also provides a composition for enhancing a stimulation of an immune response, which comprises the aforesaid fusion polypeptide. In addition, the present disclosure further provides a method with the aforesaid fusion polypeptide.

The fusion polypeptide of the present disclosure comprises: (a) a mucosa targeting polypeptide; (b) a first translocating peptide for translocation; and (c) a first antigenic epitope.

The mucosa targeting polypeptide is a binding epitope facilitating the binding of the fusion polypeptide to a receptor in a subject in need. The first translocating peptide for translocation is used as a carrier which is able to facilitate cytosolic localization and antigen presentation. The first antigenic epitope can enhance the immune-modulating activity. When the fusion polypeptide of the present disclosure comprises the aforesaid three components, the fusion polypeptide can be effectively delivered into a subject in need and enhance immune response to endogenously process target antigens.

Furthermore, another fusion polypeptide of the present disclosure comprises: (b) a first translocating peptide for translocation; and (c) a first antigenic epitope selected from SEQ ID NOs: 5 and 6. (E622, E713).

The first translocating peptide for translocation is used as a carrier which is able to facilitate cytosolic localization and antigen presentation. The first antigenic epitope is a modified antigenic epitope, which can enhance the immune-modulating activity. Especially, the sequence shown by SEQ ID NOs: 5 and 6 (i.e. E622 and E713) is modified and different from the known polypeptides of viral proteins of E6 and E7, which can further enhance the immune-modulating activity. When the fusion polypeptide of the present disclosure comprises the aforesaid two components, the fusion polypeptide can be effectively delivered into a subject in need and enhance immune response to endogenously process target antigens.

In addition, the present disclosure also provides a composition for enhancing a stimulation of an immune response, comprising: a vaccine and any one of the aforesaid fusion polypeptide. Herein, the vaccine may comprise: a second translocation peptide for translocation and a second antigenic epitope. The second translocation peptide is similar to the first translocation peptide, and the second antigenic epitope is similar to the second antigenic epitope. Thus, the descriptions about the second translocation peptide and the second antigenic epitope are not repeated again. Furthermore, in the present disclosure, the first antigenic epitope and the second antigenic epitope has to be compatible to each other. For example, both the first antigenic epitope and the second antigenic epitope are HPV antigenic epitopes; but the first antigenic epitope and the second antigenic epitope is not necessarily the same. Or, both the first antigenic epitope and the second antigenic epitope are Myostatin epitopes; but the first antigenic epitope and the second antigenic epitope is not necessarily the same. Or, both the first antigenic epitope and the second antigenic epitope are PRRSV antigenic epitopes; but the first antigenic epitope and the second antigenic epitope is not necessarily the same.

Moreover, the present disclosure also provides the method for enhancing a stimulation of an immune response, comprising: administering the aforesaid composition to a subject in need. Herein, the subject can be mammalian, such as human, pig, etc.

In one embodiment of the present disclosure, the antigenic epitope can be an HPV antigenic epitope, a Myostatin epitope, or a PRRSV antigenic epitope. In another embodiment of the present disclosure, the composition is orally administered to the subject in need.

Other objects, advantages, and novel features of the disclosure will become more apparent from the following detailed description.

EMBODIMENT

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory scheme of action.

The present disclosure is related to a platform for generating some immune-modulating chimeric polypeptides evolved in local mucosa systems, including the type-I and type-II mucosa immune system that contains a mucosa targeting polypeptide which can be a M-cell or an epithelial cell targeting domain, a translocating peptide for translocation which can be from *pseudomonas* exotoxin, and a antigenic epitope which can be a Th1 antigenic epitope.

We survey the immune responses against the antigenic epitopes of chimeric polypeptides. Especially, the immune responses can be elicited when the fusion polypeptide of the present disclosure is administered through orally administration. The fusion polypeptide of the present disclosure evolves the mucosal immune system in the intestine. Hereinafter, there are three groups of PE-based fusion antigens to demonstration the present disclosure that their specific immunities can be enhanced.

1. Mucosa Targeting Polypeptide Construct

The significant advances have been made in the identification of M-cell-specific surface markers (Kim S H et al., *J Immunol.* 2010 Nov. 15; 185(10):5787-95). In the oral route, it should comprise the M-cell or epithelial cell ligand for mucosal targeting (Azizi et al., *PLoS Pathog.* 2010 Nov. 11; 6(11); K J Syrjänen, *J Clin Pathol.* 2002 October; 55(10): 721-728; Roy C. et al., GI Motility online (2006) doi: 10.1038/gimo15). We have explored efficient recombinant production of several bio-polypeptides by exploiting the natural peptides as a fusion partner polypeptide.

The following embodiments use three kind peptides of binding epitopes as examples of the M-cell target peptides in type-I mucosa immune system. Also, one kind peptide of binding epitope is as an example of the epithelial cell targeting peptide in type-II mucosa immune system (Azizi et al., *PLoS Pathog.* 2010 Nov. 11; 6(11); K J Syrjänen, *J Clin Pathol.* 2002 October; 55(10): 721-728; Roy C. et al., *GI Motility online* (2006) doi:10.1038/gimo15; Mulder D J et al., *Dig Dis Sci.* 2012 March; 57(3):630-42). The M-cell target peptides used in the following examples are shown in Table 1. The epithelial cell targeting peptide is HPV L2-200, as shown in Table 2) for epithelial targeting ligand (Mulder D J et al., *Dig Dis Sci.* 2012 March; 57(3):630-42).

TABLE 1

The M-cell targeting polypeptides in type-I mucosa immune system

| SEQ ID NO. | Name of peptide | Amino acid codon |
|---|---|---|
| 01 | CO-1 | SFHQLPARSPAPLQ |
| 02 | DQ-2 | SSFHLFHHLPARAPLAPSELQP |
| 03 | RV-3 | STPFHPLPARKPLPLQP |

TABLE 2

The intestine epithelial cell targeting peptide

| SEQ ID NO. | Name of peptide | Amino acid codon |
|---|---|---|
| 04 | L2-200 from HPV L2 protein) | *EF*HM*VD*GMSIRAKRRKRASATQLYKTC KQAGTCPPDIIPKVEGKTIAEQILQYGSM GVFFGGLGIGTGSGTGGRTGYIPLGTRPP TATDTLAPVRPPLTVDPVGPSDPSIVSLVE ETSFIDAGAPTSVPSIPPDVSGFSITTSTDT TPAILDINNNTVTTVTTHNNPTFTDPSVL QPPTPAETGGHFTLSSSTISTHNYEEIPMD TKDEL*LE* |

*: EF, VD and LE shown in italics are the restriction enzyme sites, EcoR1 and Xho1, which are added for subcloning purpose.

1-1. Construction of M-Cell Targeting Polypeptide

The CO-1 peptide core sequence, SFHQLPARSPAPLQ (SEQ ID NO. 01), is chosen as described in Kim S H et al., *J Immunol.* 2010 Nov. 15; 185(10):5787-95. The DQ-2 and RV-3 amino acid code sequence are searched by Basic Local Alignment Search Tool (BLAST) to find the regions to mimic CO-1 sequence. The program compares protein sequences to sequence databases and calculates the statistical significance. From the amino acid codon sequence, we can find two CO-1-like peptides, DQ-2 (SEQ ID NO. 02): SFHLFHHLPARAPLAPL in *Daedalea quercina* Fr. (Polyporus-like Fugus), and RV-3 (SEQ ID NO. 03): STPFHPLPARKPLP in *Dasypus novemcinctus.*

To design and generate a DNA codon sequence without DNA template, the codon substitutions without altering the original amino acid sequence of the selected peptide segment was made for avoiding spurious restriction sites and for optimal expression in *E. coli*. Restriction site linkers were added at the ends of the peptide segment-encoding DNA sequence, EcoR1 and Xho1 at 5'end and 3'end, for insertion and sub-cloning into vector plasmids. The DNA fragment was generated by PCR and multiple primers extension. The PCR DNAs, as shown in Table 3, encoded above amino acid sequences were respectively subcloned in to *E. coli* vector plasmids by recombinant technique.

All synthesized and/or subcloned nucleotide fragments were analyzed by restriction enzyme cutting and electrophoresis to check if they were of the expected sizes and right cutting sites. Once a sample had been obtained, DNA sequences were produced automatically by machine and the result displayed on computer. Sequence analysis performed to identify the sequence of nucleotides in a nucleic acid, or amino acids in a polypeptide.

TABLE 3

The DNA sequence encoded M-cell target peptide epitopes

| SEQ ID NO. | Name of DNA | DNA codon |
|---|---|---|
| 05 | CO-1 | GAATTCAGCAGCTTTCATCTGTTCCACCATCTG CCAGCGCGTGCGCCATTAGCGCCTTCTGAATT ACAGCCCCTCGAG |
| 06 | DQ-2 | GAATTCAGCAGCTTTCATCTGTTCCACCATCTG CCAGCGCGTGCGCCATTAGCGCCTTCTGAATT ACAGCCCCTCGAG |

TABLE 3-continued

The DNA sequence encoded M-cell target peptide epitopes

| SEQ ID NO. | Name of DNA | DNA codon |
|---|---|---|
| 07 | RV-3 | GAATTCTCTACTCCTTTCCACCCATTGCCTGCC CGCAAACCATTGCCTCTGGTGCCCCTCGAG |

1-2. Construction of Intestine Epithelial Targeting Polypeptide

L2-200 DNA fragment encoding the N-terminal domain (aa 1 to 200; "L2-200") of HPV16 L2 protein was synthesized by multi-step PCR using primer pairs listed in Table 6. The primer pairs 1-10 generated DNA fragments of size 82 bp, 147 bp, 219 bp, 285 bp, 354 bp, 420 bp, 492 bp, 552 bp, and 613 bp, respectively. The final DNA product was digested by restriction enzymes Mun I and Sal I to isolate a 630 bp large DNA fragment, which was then subcloned into an EcoRI and Xho I digested vector.

TABLE 4

| Target peptide | No. of primer pairs | Fw.* primer | Nucleotide sequence of the forward primer | SEQ ID NO. | Rv.** primer | Nucleotide sequence of the reverse primer | SEQ ID NO. |
|---|---|---|---|---|---|---|---|
| L2-200 | Pair 1 | F1 | gttgacccggttgg tccgtccgacccgt ccatcgtttccctgg ttgaa | 55 | R1 | aggtcggagcaccagcgt cgatgaaggaggtttcttc aaccagggaaac | 56 |
| | Pair 2 | F2 | gacaccctggctcc ggttcgtccgccgc tgaccgttgacccg gttggt | 57 | R2 | accggaaacgtccggcg ggatggacggaacggag gtcggagcaccagc | 58 |
| | Pair 3 | F3 | tacatcccgctggg tacccgtccgccga ccgctaccgacac cctggctccg | 59 | R3 | agccggggtagtgtcggt ggaggtggtgatggagaa accggaaacgtccgg | 60 |
| | Pair 4 | F4 | ggtaccggttccgg tactggcggtcgta ccggttacatcccg ctgggt | 61 | R4 | tacggtagtaacggtgttgt tgttgatgtccaggatagc cggggtagtgtc | 62 |
| | Pair 5 | F5 | ggttctatgggtgttt tcttcggcggtctg ggcatcggtaccg gttccggt | 63 | R5 | cgggtcggtgaaggtcgg gttgttgtgagtggttacgg tagtaacggt | 64 |
| | Pair 6 | F6 | ggtaaaaccatcgc tgaacagatcctgc aatacggttctatgg gtgtt | 65 | R6 | ggtttcagccggggtcgg cggttgcagaacggacgg gtcggtgaaggt | 66 |
| | Pair 7 | F7 | ggtacctgcccgcc ggacatcatcccga aagttgaaggtaaa accatcgct | 67 | R7 | ggagatggtggaagagg acagggtgaagtgaccac cggtttcagccggggt | 68 |
| | Pair 8 | F8 | acccagctgtacaa aacctgcaaacag gctggtacctgccc gccg | 69 | R8 | gtccatcgggatttcttcgt agttgtgggtggagatggt ggaaga | 70 |
| | Pair 9 | F9 | ccgtgctaaacgtc gtaaacgtgcttcc gctacccagctgta caaaa | 71 | R9 | attatttttctcgagcagttc gtctttggtgtccatcggga tttcttc | 72 |

TABLE 4-continued

| Target peptide | No. of primer pairs | Fw.* primer | Nucleotide sequence of the forward primer | SEQ ID NO. | Rv.** primer | Nucleotide sequence of the reverse primer | SEQ ID NO. |
|---|---|---|---|---|---|---|---|
| | Pair 10 | F10 | cccgaattccatatg gtcgacggtatgtc catccgtgctaaac gtcgt | 73 | R10 | attatttttctcgagcagttc gtctttggtgtccatcggga tttcttc | 74 |

*Fw: Forward.
**Rv: Reversed.

TABLE 5

The DNA sequence encoded L2-200 target polypeptide

| SEQ ID NO. | Name of DNA | DNA codon |
|---|---|---|
| 08 | L2-200 (from HPV L2 protein) | GAATTCCATATGGTCGACGGTATGTCCATCCGTGCTA AACGTCGTAAACGTGCTTCCGCTACCCAGCTGTACA AAACCTGCAAACAGGCTGGTACCTGCCCGCCGGAC ATCATCCCGAAAGTTGAAGGTAAAACCATCGCTGAA CAGATCCTGCAATACGGTTCTATGGGTGTTTTCTTCG GCGGTCTGGGCATCGGTACCGGTTCCGGTACTGGCG GTCGTACCGGTTACATCCCGCTGGGTACCCGTCCGC CGACCGCTACCGACACCCTGGCTCCGGTTCGTCCGC CGCTGACCGTTGACCCGGTTGGTCCGTCCGACCCGT CCATCGTTTCCCTGGTTGAAGAAACCTCCTTCATCG ACGCTGGTGCTCCGACCTCCGTTCCGTCCATCCCGC CGGACGTTTCCGGTTTCTCCATCACCACCTCCACCG ACACTACCCCGGCTATCCTGGACATCAACAACAACA CCGTTACTACCGTAACCACTCACAACAACCCGACCT TCACCGACCCGTCCGTTCTGCAACCGCCGACCCCGG CTGAAACCGGTGGTCACTTCACCCTGTCCTCTTCCA CCATCTCCACCCACAACTACGAAGAAATCCCGATGG ACACCAAAGACGAACTGCTCGAG |

As shown in Tables 1 and 2, the mucosa targeting polypeptide used in the fusion polypeptide of the present disclosure may be an M-cell targeting polypeptide (such as CO1, DQ2 and RV3) or an intestine epithelial targeting polypeptide (such as L2-200). The polypeptides CO1, DQ2, RV3 and L2-200 respectively have an amino acid sequence represented by SEQ ID NOs: 1 to 4.

In the present disclosure, the antigenic epitope comprised in the fusion polypeptide of the present disclosure is a Th1 antigenic epitope. Examples of the Th1 antigenic epitope can be an HPV antigenic epitope, a Myostatin epitope, or a PRRSV antigenic epitope. Hereinafter, the syntheses of the HPV antigenic epitope, the Myostatin epitope and the PRRSV antigenic epitope are described in detail.

2. The HPV Th1 Epitopes and its Modified Polypeptides of Viral Proteins of E6 and E7

In the present disclosure, the HPV antigenic epitope can be an E7 peptide sequence or an E6 peptide sequence of human papillomavirus type 16.

Sarkar A. K. et al (2005) suggest that cellular immune responses specific to the E6 and E7 peptides have a role in the protective immunity against HPV-associated CIN (Sarkar A K et al., *Gynecol Oncol.* 2005 December; 99 (3 Suppl 1):S251-61). A fused peptide E601, SEQ ID NO. 9: EFVDQLLRREVFCGFRDLVYDFAFSDLKLPQLCTEL KLPQLCTELLE was introduced since the peptide Q15L (QLLRREVYDFAFRDL) and V10C (VYDFAFRDLC) of HPV-16 E6 had a good CMI response.

A fused peptide E701, SEQ ID NO. 11: EFVD QAEPDOAEPDRARAHYNIRARAHYNILRAHYNIVIF RAHYNIVIF LE was synthesized, according to Tindle R. W et al in 1995 (Tindle R. W et al., *Clin Exp Immunol.* 1995; 101:265-271). They report that an ISCAR (=Immunostimulatory Carrier) with a BT5 peptide of HPV16 E7 which contains the linear B epitope 44QAEPD48, the Th epitope 48DRAHYNI54, and the overlapping CTL epitope 49 RAHYNIVTF57, has a good therapeutic effect.

The E622 and E713 were modified from E601 and E701-polypeptide sequences according to the proteasome cleavage site prediction software (http://www.imtech.res.in/raghava/pcleavage/): an SVM based method for prediction of constitutive proteasome and immunoproteasome cleavage sites in antigenic sequences for Th1 pathway. The polypeptides sequence of E601, E622, E701 and E713 are shown as Table 6.

TABLE 6

The Th1 epitopes and its modified polypeptides of viral proteins of E6 and E7

| SEQ ID NO. | Name of peptide | Amino acid codon |
|---|---|---|
| 09 | E601 | *EFVD*QLLRREVFCGFRDLVYDFAFSDLKLPQLCTELKLPQ LCTEL*LE* |
| 10 | E622 | *EFVD*KDELREVYNFAFLLVLRREVYDKDELLLLLEDRQL LRREVFCGFRDLLEDRVYDFAFSDLKLPQLCTELKLPQLC TELKDELKDELVLLL*LE* |
| 11 | E701 | *EFVD*QAEPDQAEPDRARAHYNIRARAHYNILRAHYNIVIF RAHYNIVIF*LE* |
| 12 | E713 | *EFVD*QAEPDQAEPDRDELVLRARAHYNIRARAHYNILED RLLVLRAHYNIVIFRAHYNIVIFKDELLV*LE* |

*: EF, VD and LE shown in italics are the restriction enzyme sites, EcoR1 and Xho1, which are added for subcloning purpose.

The DNA encoded of the E601, E622, E701 and E713 was designed. Codon substitutions without altering the original amino acid sequence of the selected peptide segment were made for avoiding spurious restriction sites and for optimal expression in *E. coli*. Restriction site linkers were added at the ends of the peptide segment-encoding DNA sequence, EcoR1, Sal1 and Xho1 at 5'end and 3'end, for insertion and sub-cloning into a vector plasmid. The target DNA sequence of E601, E622, E701 and E713 were generated by PCR (polymerase chain reaction) and multiple primers extension, the DNA condones are shown as Table 7. The DNA fragments of the modified nucleic acid sequence encoding target chimeric polypeptides were synthesized by PCR with multiple primers (U.S. Pat. No. 8,372,407). Non-DNA template PCR was performed. After the first run PCR, 0.01-1 μl of the DNA product were used as a DNA template for the second run PCR, in which the second primer pair was added together with dNTPs, reagents and Pfu polymerase. The remaining primer pairs were sequentially added in this manner at the subsequent runs of PCR until the target peptide-encoding DNA fragments were respectively synthesized (US

TABLE 7

The DNA codon sequences of various HPV polypeptides

| SEQ ID NO. | Name of DNA | DNA sequence |
|---|---|---|
| 13 | E601 | *GAATTC***GTCGAC**CAACTGTTGCGTCGTGAAGTTTTC<br>TGTGGCTTTCGTGATCTGGTCTATGACTTCGCCTTTA<br>GTGATTTGAAGCTGCCACAATTGTGTACGGAACTGA<br>AACTGCCTCAACTGTGTACAGAACTGAAGGATGAG<br>CTG***CTCGAG*** |
| 14 | E622 | *GAATTC***GTCGAC**AAAGATGAACTGCGTGAGGTGTAT<br>AACTTTGCGTTCCTGTTAGTGTTACGCCGTGAGGTTT<br>ATGAcAAGGACGAGTTGTTACTGCTGTTAGAAGATC<br>GCCAACTGTTGCGTCGTGAAGTTTTCTGTGGCTTTC<br>GTGATCTGTTAGAAGACCGCGTCTATGACTTCGCCT<br>TTAGTGATTTGAAGCTGCCACAATTGTGTACGGAAC<br>TGAAACTGCCTCAACTGTGTACAGAACTGAAGGAT<br>GAGCTGAAAGATGAATTAGTGCTGTTATTG***CTCGAG*** |
| 15 | E701 | *GAATTC***GTCGAC**CAGGCGGAACCAGATCAAGCGGA<br>ACCTGACCGTGCCCGCGCACATTATAACATTCGCGC<br>ACGTGCACACTATAATCTGGAGGCGCATTATAACATT<br>GTCATCTTCCGCGCACATTATAACATCGTCATTTTC***C<br>TCGAG*** |
| 16 | E713 | *GAATTC***GTCGAC**CAGGCGGAACCAGATCAAGCGGA<br>ACCTGACCGTGACGAGCTGGTGTTACGCGCCCGCG<br>CACATTATAACATTCGCGCACGTGCACACTATAATCT<br>GGAGGATCGTTTACTGGTCTTGCGTGCGCATTATAAC<br>ATTGTCATCTTCCGCGCACATTATAACATCGTCATTTT<br>CAAAGATGAGTTGCTGGTT***CTCGAG*** |

3. The Polypeptides of Myostatin Epitopes

Myostatin (also known as growth differentiation factor 8, abbreviated GDF-8) is a myokine, a protein produced and released by myocytes that acts on muscle cells' autocrine function to inhibit myogenesis: muscle cell growth and differentiation. In humans, it is encoded by the MSTN gene. Myostatin is a secreted growth differentiation factor that is a member of the TGF beta protein family. Animals either lacking myostatin or treated with substances that block the activity of myostatin have significantly more muscle mass. Furthermore, individuals who have mutations in both copies of the myostatin gene have significantly more muscle mass and are stronger than normal. Studies into myostatin shows that myostatin may have therapeutic application in treating muscle wasting diseases such as muscular dystrophy (Hamrick M K, *IBMS BoneKEy.* 2010 January; 7(1):8-17).

3-1. M14 and M27 Construct

M14 peptide epitope was selected a partial fragment of myostatin binding domain; DFGLDCDEHSTESRCCRYPLTVDFEAFGWDWIIAPKRYKANYCSGECEFVFLQKYPHTHLVHQANPRGSAGPCCTPTLMSPINMLYFNGKEQIIYGKIP AMVVDRCGCS, which has been patented in US20020127234. The M14 peptide core sequence, FLQKYPHTHLVHQA, was selected. Codon substitutions without altering the original amino acid sequence of the selected peptide segment were made for avoiding spurious restriction sites and for optimal expression in *E. coli*. Restriction site linkers were added at the ends of the peptide segment-encoding DNA sequence, EcoR1-Sal1 and Xho1 at 5'end and 3'end, for insertion and sub-cloning into a vector plasmid. The DNA sequence encoded the amino acid sequence of EFVDFLQKYPHTHLVHQALE was 5'-GAATTCGTCGACGTGTTTTACAAAAATATCCTATACGCACTGGTCCATCAGGCGCTCGAC-3'. The DNA fragment was generated by PCR and multiple primers extension. Furthermore, the polypeptide with four repeated core sequence, EFVDVFLQKYPHTHLVHQALDVFLQKYPHTHLVHQALDVFLQKYPHTHLVHQALDVFLQKYPHTHLVHQALE (SEQ CO NO. 17), was generated with repeated insertion by recombinant technique.

M27 was modified polypeptide to present a Th1 epitope characteristics according to the proteasome cleavage site prediction software (http://www.imtech.res.in/raghava/pcleavage/): an SVM based method for prediction of constitutive proteasome and immunoproteasome cleavage sites in antigenic sequences. There are two polypeptide fragments: HTHLVHQA peptide and EFLQKYPH peptide are fused and modified to create the M27 chimeric polypeptide (no. 3). The HTHLVHQA peptide is searched by Basic Local Alignment Search Tool (BLAST) to find regions of similarity between biological sequences. The program compares protein sequences to sequence databases and calculates the statistical significance. Its amino acid codon sequence can be found in the CHLNCDRAFT_134428 protein of *Chlorella variabilis* (sequence ID: ref XP_005847307). The amino acid codon sequence of EFLQKYPH peptide can be found in the ROOT PRIMORDIUM DEFECTIVE 1 isoform X4 of *Cicer arietinum* (sequence ID: ref XP_012571622.1). The two fusion peptide genes are respectively subcloned in to *E. coli* vector plasmids and then fused together by recombinant technique. The modified DNA fragment encoded of LEP-HTHLVHQA-NVLLALQLLLEDREF, which added one Xho1 restriction enzyme site at 5'-end and a DNA linker or bridge encoded with NVLLALQLLLEDREF peptide at 3'-end, is generated by primer extension and PCR running method. This DNA linker encoded NVLLALQLL peptide is created by an SVM based method for proteasome cleavage prediction. LEDR signal also is added into fusion peptide in order to enhance Th1 immune response when the peptide is sorted nearby ER location. The DNA fragment encoded of LE PHTHLVHQANVLLALQLLLEDREF peptide is generated by PCR technique. The DNA fragment encoded of HTHLVHQA is inserted into the site of Xho1 and EcoR1 of *E. coli* plasmid vector. The DNA fragment encoded of E FLQKYPHVD with two restriction enzyme sites, EcoR1 and Sal1, is generated by PCR technique. The DNA fragment encoded of the peptide of LEPHTHLVHQANVLLALQLLLEDREFVFLQKYPHVD is fused the DNA fragment encoded of HTHLVHQA and the DNA fragment encoded of EFLQKYPHVD by recombinant technique. Furthermore, a DNA fragment with eight repeated insertion was created.

As shown in Table 8, a core of fused epitope: EFVFLQKYPHVEPHTHLVHQANV was generated, and the amino acid sequence is similar to the EFVFLQKYPHTHLVHQAN of Myostatin domain in US20020127234. Finally, the polypeptides sequence of M14 (SEQ ID NO. 17) and M27 (SEQ ID NO. 18) are shown as Table 8. The DNA coded M14 and M27 are shown as Table 9.

TABLE 8

The modified polypeptides of Myo14 and Myo27

| SEQ ID NO. | Name of peptide | Amino acid codon |
|---|---|---|
| 17 | M14 | *EFVD*VFLQKYPHTHLVHQALDVFLQKYPHTHL<br>VHQALDVFLQKYPHTHLVHQALDVFLQKYPHT<br>HLVHQA*LE* |
| 18 | M27 | *EF*L*LE*PHTHLVHQANVLLALQLLLEDREFVFLQ<br>KYPHVEPHTHLVHQANVLLALQLLLEDREFVFL<br>QKYPHVEPHTHLVHQANVLLALQLLLEDREFV<br>FLQKYPHVEPHTHLVHQANVLLALQLLLEDREF<br>VFLQKYPHVEPHTHLVHQANVLLALQLLLEDR<br>EFVFLQKYPHVEPHTHLVHQANVLLALQLLLE<br>DREFVFLQKYPHVEPHTHLVHQANVLLALQLL<br>LEDREFVFLQKYPHVEPHTHLVHQANVLLALQ<br>LLLEDREFVFLQKYPH*VD* |

*: VD, EF and LE shown in italics are the restriction enzyme sites, EcoR1 and Xho1, which are added for subcloning purpose.

TABLE 9

The DNA code sequences of Myo14 and Myo27

| SEQ ID NO. | Name of DNA | DNA code sequence |
|---|---|---|
| 19 | M14 | *GAATTC***GTCGAC**GTGTTTTTACAAAAATATCCTCAT<br>ACGCACCTGGTCCATCAGGCGCTCGACGTGTTTTT<br>ACAAAAATATCCTCATACGCACCTGGTCCATCAGG<br>CGCTCGACGTGTTTTTACAAAAATATCCTCATCGC<br>ACCTGGTCCATCAGGCGCTCGACGTGTTTTTACAA<br>AAATATCCTCATACGCACCTGGTCCATCAGGCG***CTC<br>CAG*** |
| 20 | M27 | *GAATTC*CTC***CTCGAG***CCACATACGCACTTAGTGCAT<br>CAAGCGAACGTTTTGCTGGCACTGCAATTATTATTA<br>GAAGATCGTGAATTTGTCTTCTTGCAAAAATATCCA<br>CACGTCGAGCCACATACGCACTTAGTGCATCAAGC<br>GAACGTTTTGCTGGCACTGCAATTATTATTAGAAGA<br>TCGTGAATTTGTCTTCTTGCAAAAATATCCACACGT<br>CGAGCCACATACGCACTTAGTGCATCAAGCGAACG<br>TTTTGCTGGCACTGCAATTATTATTAGAAGATCGTG<br>AATTTGTCTTCTTGCAAAAATATCCACACGTCGAGC<br>CACATACGCACTTAGTGCATCAAGCGAACGTTTTG<br>CTGGCACTGCAATTATTATTAGAAGATCGTGAATTT<br>GTCTTCTTGCAAAAATATCCACACGTCGAGCCACAT<br>ACGCACTTAGTGCATCAAGCGAACGTTTTGCTGGC<br>ACTGCAATTATTATTAGAAGATCGTGAATTTGTCTT<br>CTTGCAAAAATATCCACACGTCGAGCCACATACGC<br>ACTTAGTGCATCAAGCGAACGTTTTGCTGGCACTG<br>CAATTATTATTAGAAGATCGTGAATTTGTCTTCTTGC<br>AAAAATATCCACACGTCGAGCCACATACGCACTTA<br>GTGCATCAAGCGAACGTTTTGCTGGCACTGCAATT<br>ATTATTAGAAGATCGTGAATTTGTCTTCTTGCAAAA<br>ATATCCACACGTCGAGCCACATACGCACTTAGTGCA<br>TCAAGCGAACGTTTTGCTGGCACTGCAATTATTATT<br>AGAAGATCGTGAATTTGTCTTCTTGCAAAAATATCC<br>ACAC**GTCGAC** |

4. The Fusion Polypeptides of PRRSV Epitope

Porcine reproductive and respiratory syndrome virus (PRRSV) causes chronic, economically devastating disease in pigs. Frequent mutations in the viral genome result in viruses with immune escape mutants. Irrespective of regular vaccination, control of PRRSV remains a challenge to swine farmers. At present, enhancing the early immunological mechanisms in PRRSV-infected pigs can improve preventive or therapeutic purpose (0. J. Lopez et al., *Clin Vaccine Immunol.* 2007 March; 14(3): 269-275). Recently, we try to develop an immune enhancer for oral administration. Three immunomodulating polypeptides (GP317, GP417 and GP437) from PRRSV GP3 and GP4 epitopes are selected.

4-1. GP317, GP417 and GP437 Construct

GP317, GP417 and GP437 DNA fragment encoding the virus neutralization domain of PRRSV GP3 and GP4 proteins, as shown in Table 10, were synthesized by multi-step PCR using primer pairs. Codon substitutions without altering the original amino acid sequence of the selected peptide segment were made for avoiding spurious restriction sites and for optimal expression in *E. coli*. Restriction site linkers were added at the ends of the peptide segment-encoding DNA sequence, EcoR1 and Xho1 at 5'end and 3'end, for insertion and sub-cloning into a vector plasmid. The final DNA products, as shown in Table 11, were digested by restriction enzymes EcoR1 and Xho1 to isolate DNA fragments, which were then subcloned into an EcoRI and Xho I digested vector. Once a sample had been obtained, DNA sequences were produced automatically by machine and the result displayed on computer. Sequence analysis performed to identify the sequence of nucleotides in a nucleic acid, or amino acids in a polypeptide.

TABLE 10

The immunomodulating polypeptide-enhancers

| SEQ ID NO. | Name of peptide | Amino acid codon |
|---|---|---|
| 21 | GP317 | *EF*VSFSTGGSQNWTVERLLQAEFCSTSQAARQRLE<br>TGRNCSTGQAARQRLEPGRNLVLCLTSQAAQQRLE<br>PGGNCQTSQAAHQRLEPGRNCRTSQAASQRLEPGR<br>NCRTSQAAHQRLEPGRNCSTRQAAQQRLEPGRNLL<br>CPTSQAAHQRRLEPGRNCSTSQAAYQRLEPGRNCP<br>TSRAARQRLEPGRNLLCSTSQAALQRLEPGRNLCPT<br>SQAAKQRLEPGRNLVVCLTSQAARQRLEPGRNCST<br>SQAASQRLEPGRNCPTSQAARQRLEPGRNVLLLCL<br>TSQAAHQRLEPGRN*LE* |
| 27 | GP417 | *EF*GVSAAQEKISFGLLGVPTAQETTSIREVLEVSTAQ<br>ENSPFMLGASATEEKTSLRLGASTTQETSFGKCLRP<br>HGVSAAQGTTPFRGVSTTQENTSFGRVPTAQENVSF<br>GLHGVPAAQKTNSFGGVPTAQENISFKEVSATQREI<br>PFRCLRPHGVSTAQETPFRGVSTAQETIPFRGVSATH<br>ENISFGCLRPHGVSAAQESIPIRLGASAAQENTSFRG<br>TPAAQEKIP*LE* |
| 23 | GP437 | *EF*LGVSAAQERIPIREVSADKEVSNEKKEISFGVSTA<br>QGNISFGLGVSTAQEAIPFLALGVSTAQETIPFGLLG<br>VSTAQGIISFGGVSTAQENISFGGVSTAQETISFGLLG<br>VSTAQENISFGCLRTHEVSAAQEKISFGGVSEAQKIS<br>FGVSAAGVSAAQEEIPFGCLRPHGLPAAQEKTSFGG<br>VSAAQEKTSFGGVSAAQEEFSFGCLRPHRVSAAQE<br>KISFEVSALEVSAAQEKISFGVSAALGVSAAQEKNS<br>FGCLRPHGVSAAQEKTSFGGVSAAQKKISFG*LE* |

*: VD, EF and LE shown in italics are the restriction enzyme sites, EcoR1 and Xho1, which are added for subcloning purpose.

TABLE 11

The DNA sequence encoded the immunomodulating polypeptide-enhancers

| SEQ ID NO. | Name of peptide | Amino acid codon |
|---|---|---|
| 24 | GP317 | GGAATTCGTGAGCTTTAGCACGGGTGGCAGCCAG<br>AACTGGACGGTGGAACGTCTGCTGCAAGCCGAGT<br>TCTGTAGTACTTCTCAGGCGGCGCGCCAGCGTCTG |

TABLE 11-continued

The DNA sequence encoded the immunomodulating polypeptide-enhancers

| SEQ ID NO. | Name of peptide | Amino acid codon |
|---|---|---|
| | | GAACCAGGGCGTAATTGTTCTACAGGCCAGGCCGC<br>ACGTCAACGTTTAGAGCCAGGTCGCAATTTAGTTT<br>TGTGTCTGACGAGCCAGGCCGCACAGCAGCGCTT<br>GGAACCAGGCGGTAACTGTCAAACTTCTCAAGCG<br>GCCCATCAACGCCTGGAACCAGGTCGCAACTGTCG<br>CACTAGCCAAGCCGCCAGCCAACGTTTAGAGCCA<br>GGCCGCAACTGTCGCACGAGTCAGGCGGCGCACC<br>AACGTCTGGAACCAGGCCGTAATTGTAGTACGCGC<br>CAAGCAGCCCAGCAACGCTTAGAACCAGGGCGCA<br>ACCTGTTATGTCCAACTTCTCAGGCGGCCCATCAA<br>CGCCGCTTAGAACCAGGGCGTAATTGTAGCACGTC<br>TCAAGCAGCATATCAACGTCTGGAACCAGGCCGCA<br>ACTGTCCAACTTCTCGTGCGGCACGCCAGCGCTTA<br>GAACCAGGTCGTAATTTATTATGTTCTACTAGCCAA<br>GCCGCATTACAGCGTTTAGAGCCAGGGCGTAACCT<br>GTGTCCAACTAGCCAAGCAGCAAAACAACGCCTG<br>GAGCCAGGTCGTAATTTAGTGGTCTGTTTAACGAG<br>CCAAGCGGCGCGTCAACGCTTAGAACCAGGTCGC<br>AATTGTTCTACTAGCCAAGCGGCCAGTCAACGTTT<br>AGAACCAGGGCGCAACTGTCCAACGAGCCAAGCG<br>GCGCGCCAACGTTTAGAGCCAGGGCGCAACGTTTT<br>ATTGTTGTGTCTGACGAGTCAAGCCGCCCATCAAC<br>GTCTGGAACCAGGTCGCAATCTCGAG |
| 25 | GP417 | GAATTCGGCGTGAGCGCGGCCCAGGAAAAGATCA<br>GTTTCGGCCTGTTAGGTGTGCCAACGGCCCAAGAG<br>ACTACAAGTATTCGCGAGGTTTTGGAAGTCAGTAC<br>TGCACAAGAAAACAGTCCATTTATGTTAGGCGCGA<br>GTGCCACGGAGGAAAAAACGTCTTTGCGCCTGGG<br>GGCAAGCACAACGCAGGAGACGAGTTTTGGCAAG<br>TGTTTACGTCCACATGGGGTTTCTGCAGCCCAAGG<br>GACGACTCCATTTCGCGGTGTCAGTACAACGCAAG<br>AAAACACGAGTTTTGGTCGTGTCCCAACGGCACA<br>AGAGAACGTGTCTTTTGGCCTGCATGGTGTTCCAG<br>CAGCGCAAAAGACGAACAGCTTCGGTGGCGTTCC<br>AACGGCACAAGAAAACATTAGTTTTAAGGAGGTTA<br>GTGCCACGCAACGTGAAATCCCATTCCGTTGTTTA<br>CGCCCACACGGGGTTAGCACAGCCCAGGAGACTC<br>CATTTCGCGGGGTGAGTACTGCCCAGGAGACGATC<br>CCATTCCGTGGGGTTTCTGCAACGCATGAAAACAT<br>CAGTTTTGGGTGTTTGCGTCCACATGGTGTCAGCG<br>CCGCACAGGAATCTATTCCAATCCGTCTGGGCGCG<br>AGCGCAGCCCAAGAGAATACCAGTTTTCGCGGGA<br>CACCAGCGGCACAGGAGAAAATCCCATTGGAACT<br>CGAG |
| 26 | GP437 | GAATTCCTGGGCGTGAGCGCAGCCCAAGAGCGCA<br>TCCCAATTCGCGAGGTGAGCGCCGACAAAGAGGT<br>GAGTGCCGAGAAGAAAGAGATCTCTTTCGGGGTG<br>AGCACCGCGCAGGGTAATATCAGTTTTGGTTTGGG<br>CGTCAGCACCGCACAGGAGGCAATTCCATTCTTGG<br>CACTGGGGGTCAGTACCGCCCAGGAAACTATTCCA<br>TTTGGCTTGCTGGGGGTTAGCACTGCACAAGGTAT<br>CATTAGTTTCGGCGGGGTCTCTACTGCGCAGGAGA<br>ATATCAGCTTTGGCGGGGTTAGTACTGCGCAAGAG<br>ACCATTAGTTTTGGTTTGCTGGGCGTTTCTACCGCC<br>CAGGAGAATATTAGCTTTGGTTGTTTACGCACTCAT<br>GAAGTTAGTGCCGCACAAGAGAAAATTAGCTTCGG<br>CGGCGTTAGTGAAGCGCAAGAGAAGATTAGTTTCG<br>GGGTCTCTGCAGCAGGCGTCAGCGCCGCCCAAGA<br>GGAGATTCCATTTGGGTGTCTGCGCCCACACGGCC<br>TGCCAGCGGCGCAGGAGAAAACCAGCTTCGGCGG<br>CGTTAGTGCCGCCCAGGAAAAGACCTCTTTCGGTG<br>GTGTCAGCGCAGCACAAGAAGAGTTCTCTTTTGGT<br>TGTTTGCGCCCACATCGTGTTAGTGCCGCACAGGA<br>AAAGATCAGCTTTGAAGTTAGCGCGCTGGAAGTCA<br>GTGCCGCGCAAGAGAAGATTAGTTTTGGCGTTAGC<br>GCGGCATTGGGTGTCAGCGCAGCACAAGAAAAGA<br>ACTCTTTCGGTTGTTTACGCCCACACGGTGTTAGC<br>GCCGCGCAAGAGAAAACCAGCTTCGGGGGTGTTA<br>GTGCCGCACAAAAAAAGATCAGCTTTGGGCTCGA<br>G |

As shown in Tables 6, 8 and 10, the antigenic epitope used in the fusion polypeptide of the present disclosure may be E622, E713, Myo27, Myo14, GP317, GP417 or GP437, which respectively has a sequence shown by SEQ ID NOs: 10, 12, 17, 18, 21, 22 or 23.

In the present disclosure, a translocating peptide is comprised in the fusion polypeptide of the present disclosure as a carrier. The translocating peptide can be from *pseudomonas* exotoxin. In one aspect of the present disclosure, the translocating peptide comprises a *pseudomonas* exotoxin A fragment deleted of only domain III. Hereinafter, the synthesis of the translocating peptide is described in detail.

5. *Pseudomonas* Exotoxin (PE) Toxoid Carrier Constructs for Delivered Peptide Antigens in the Intracellular Processing System

*Pseudomonas* exotoxin A (PE) polypeptide contains domains Ia, II, Ib and III. It has a total of 613 amino acids, the full length PE-DNA fragment was published (Liao C W et al., *Applied Microbiology and Biotechnology*, July 1995, Volume 43, Issue 3, pp 498-507) and the subcloned strains are stored in Liao Lab. To investigate whether the C-terminal deletions of the PE polypeptide fragment would impact the immunogenicity of PE-fused Th1 epitopes, A series of DNA fragments encoding various lengths of *Pseudomonas* exotoxin A polypeptide were synthesized using primer pairs listed in Table 12: PE-425, PE-407, PE-49. The term "PE-N" stands for a PE fragment consisting of as 1-N, in which N is an integer. For example, "PE-425" is a PE fragment consisting of as 1-425, and "PE-407" is a PE consisting of as 1-407.

5-1. Example 1: pPE49 Plasmid

PE49 target gene is cloned in pET15b plasmids under control of strong bacteriophage T7 transcription and (optionally) translation signals; expression is induced by providing a source of T7 RNA polymerase in the host cell. Plasmid pPE49 was constructed as follows. A 159 bp DNA fragment comprising a nucleotide sequence encoding PE as 1-49 was synthesized by PCR using the primer pair PE-F1 and PE-R1, as shown in Table 12. The 165 bp PCR product was digested by Xho1 I and Nde I to isolate a 159 bp fragment. It was then subcloned into the 5.9 kb large DNA fragment which was cut from pET15b with Xho1 I and Nde I to generate plasmid pPE-49 (6079 bp).

5-2. Example 2: pPE407 Plasmid

PE407 target gene is cloned in pET15b plasmids under control of strong bacteriophage T7 transcription and (optionally) translation signals; expression is induced by providing a source of T7 RNA polymerase in the host cell. Plasmid pPE407 was constructed as follows. A 1224 bp DNA fragment comprising a nucleotide sequence encoding PE aa 1-407 was synthesized by PCR using the primer pair PE-F1 and PE-R2 as shown in Table 12. The 1238 bp PCR product was digested by Xho1 I and Nde I to isolate a 1224 bp fragment. It was then subcloned into the 5.9 kb large DNA fragment which was cut from pET15b with Xho1 I and Nde I to generate plasmid pPE-407 (7159 bp).

5-3. Example 3: pPE425 Plasmid

PE425 target gene is cloned in pET15b plasmids under control of strong bacteriophage T7 transcription and (optionally) translation signals; expression is induced by providing a source of T7 RNA polymerase in the host cell. Plasmid pPE425 was constructed as follows. A 1299 bp DNA fragment comprising a nucleotide sequence encoding PE as 1-425 was synthesized by PCR using the primer pair PE-F1 and PE-R3 as shown in Table 12. The 1299 bp PCR product was digested by Xho1 I and Nde I to isolate a 1293 bp fragment. It was then subcloned into the 5.9 kb large DNA fragment which was cut from pET15b with Xho1 I and Nde I to generate plasmid pPE-425 (7213 bp).

The nucleotide and amino acid sequences of the above PE fragments are poly-His epitopes, flanked by linkers MGSSHHHHHH and LEHHHHHHZ at 5'- and 3'- (or N- and C-) ends, respectively.

TABLE 12

| Target PE | Fw.* primer | Nucleotide sequence of the forward primer | SEQ ID No. | Rv.** primer | Nucleotide sequence of the reverse primer | SEQ ID No. |
|---|---|---|---|---|---|---|
| PE49 | PE-F1 | ccccatatggc cgaagaagct | 75 | PE-R1 | tttctcgagttgaat tccatggagtagttc atcactccctggccg ttgg | 76 |
| PE407 | PE-F2 | ccccatatggc cgaagaagct | 77 | PE-R2 | tttctcgaggaattc gacgtcgccgccgtc gccgaggaactccg | 78 |
| PE425 | PE-F3 | ccccatatggc cgaagaagct | 79 | PE-R3 | tttctcgaggaattc cgcctggagcagccg ctccaccg | 80 |

*Fw: Forward.
**Rv: Reversed.

The target DNA fragment of PE-fused antigenic epitopes can be inserted into Xho1 restriction enzyme site of pPE407 and pPE425.

6. Plasmid Constructions for the Mucosal Targeting Fused Polypeptides of Immune Enhancer

6-1. Plasmid Vector Construction for Subcloning

PE49-3, plasmid construction for insertion of the DNA fragment of M-cells target peptide epitopes. The plasmid is original from the pPE49 plasmid. It was modified by PCR and recombinant manipulation. The primers and sequence modification were shown in Tables 13 and 14.

TABLE 13

| Target PE | Fw.* primer | Nucleotide sequence of the forward primer | SEQ ID No. | Rv.** primer | Nucleotide sequence of the reverse primer | SEQ ID No. |
|---|---|---|---|---|---|---|
| PE49-3 | PE-F4 | tataccatggc cgaacaattgg tggacctc | 81 | PE-R4 | tttctcgaggaatt cttccatgcagtag tgcagcacgccc | 82 |

*Fw: Forward.
**Rv: Reversed.

TABLE 14

The difference of N-terminal amino acid sequence and DNA sequences and its restriction sites between pPE49 and pPE49-3

The N-terminal amino acid sequence of P49:

MGSSHHHHHHSSGLVPRGSAMAE*EAF*DLWNECAKACVLDLKDGVRSS
RMSVDPAIADTNGQGVLHYSMEFLEHM

TABLE 14-continued

The difference of N-terminal amino acid sequence and DNA sequences and its restriction sites between pPE49 and pPE49-3

The N-terminal amino acid sequence of P49-3:

MAE*QLV*DLWNECAKACVLDLKDGVRSS
RMSVDPAIADTNGQGVLHY*C*MEFLEHM

The 5'-end pP49 DNA sequence behind T7 promotor site direction:

ATGGGCAGCAGCCATCATCATCATCATCACAGCAGCGGCCTGGTGCC

Nde1
GCGCGGCAGCGCCATGGCCGAAGAAGCTTTCGACCTCTGGAACGAA
TGCGCCAAAGCCTGCGTGCTCGACCTCAAGGACGGCGTGCGTTCCAG
CCGCATGAGCGTCGACCCGGCCATCGCCGACACCAACGGCCAGGG

Nco1 EcoR1 Xho1 Nde1
CGTGCTGCACTACTCCATG*GAATTC*CTCGAG*CATATG*GCCGAAG

HindIII
AAGCTTTCGACCTCTGGAACGAATGCGCCAAAGCCTGCGTGCTCGA

Sal1
CCTCAAGGACGGCGTGCGTTCCAGCCGCATGAGCGTCGAC

The 5'-end pP49-3 DNA sequence behind T7 promotor site direction:

Nco1 Mfe1
TTTTGTTTAACTTTAAGAAGGAGATATACCATGGCCGAACAATTGGT
GGACCTCTGGAACGAATGCGCCAAAGCCTGCGTGCTCGACCTCAAG
GACGGCGTGCGTTCCAGCCGCATGAGCGTCGACCCGGCCATCGCCG

EcoR1
ACACCAACGGCCAGGGCGTGCTGCACTACTGCATGGAATTC

Xho1 Nde1 HindIII
CTCGAG*CATATG*GCCGAAGAAGCTTTCGACCTCTGGAACGAATGCGC
CAAAGCCTGCGTGCTCGACCTCAAGGACGGCGTGCGTTCCAGCCGCA
TGAGCGTCGAGCACCACCACCACCACCACTGA

6-2. Plasmid Constructions for the M-Cell Targeting Polypeptides

Three DNA fragments (CO1, DQ2, RV3) of M-cell ligand were respectively ligated into EcoR1 and Xho1 restriction enzymes digested pPE49-3/pET plasmids so that the DNA fragment encode the M-cell ligand was inserted downstream of T7 promoter. Plasmids containing inserts were respectively transformed into *E. coli* and clones selected for by ampicillin resistance. The partial DNA sequences of the insertion portions of pP49-3-CO1, pPE49-3-DQ2, and pPE49-3-RV3 plasmids are shown in Table 15.

TABLE 15

| Plasmid name | SEQ ID NO. | DNA sequence |
|---|---|---|
| pP49-3-CO1 | 27 | GTTTAACTTTAAGAAGGAGATATACCATGGC CGAACAATTGGTGGACCTCTGGAACGAATG CGCCAAAGCCTGCGTGCTCGACCTCAAGGA CGGCGTGCGTTCCAGCCGCATGAGCGTCGA CCCGGCCATCGCCGACACCAACGGCCAGG GCGTGCTGCACTACTGCATGGAATTCTCTTT TCATCAGCTGCCAGCGCGTTCTCCAGCCC CACTGCAGCTCGAGCATATGGCCGAAGAAG CTTTCGACCTCTGGAACGAATGCGCCAAAG CCTGCGTGCTCGACCTCAAGGACGGCGTGC GTTCCAGCCGCATGAGCGTCGAGCACCACC ACCACCACCACTGAGATCCGGCTGCTAAC |

TABLE 15-continued

| Plasmid name | SEQ ID NO. | DNA sequence |
|---|---|---|
| pP49-3-DQ2 | 28 | GTTTAACTTTAAGAAGGAGATATACCATGGC<br>CGAACAATTGGTGGACCTCTGGAACGAATG<br>CGCCAAAGCCTGCGTGCTCGACCTCAAGGA<br>CGGCGTGCGTTCCAGCCGCATGAGCGTCGA<br>CCCGGCCATCGCCGACACCAACGGCCAGG<br>GCGTGCTGCACTACTGCATGGAATTCAGCA<br>GCTTTCATCTGTTCCACCATCTGCCAGCGC<br>GTGCGCCATTAGCGCCTTCTGAATTACAG<br>CCCCTCGAGCATATGGCCGAAGAAGCTTTCG<br>ACCTCTGGAACGAATGCGCCAAAGCCTGCG<br>TGCTCGACCTCAAGGACGGCGTGCGTTCCA<br>GCCGCATGAGCGTCGAGCACCACCACCACC<br>ACCACTGAGATCCGGCTGCTAAC |
| pP49-3-RV3 | 29 | GTTTAACTTTAAGAAGGAGATATACCATGGC<br>CGAACAATTGGTGGACCTCTGGAACGAATG<br>CGCCAAAGCCTGCGTGCTCGACCTCAAGGA<br>CGGCGTGCGTTCCAGCCGCATGAGCGTCGA<br>CCCGGCCATCGCCGACACCAACGGCCAGG<br>GCGTGCTGCACTACTGCATGGAATTCTCTAC<br>TCCTTTCCACCCATTGCCTGCCCGCAAACC<br>ATTGCCTCTGGTGCCCCTCGAGCATATGGC<br>CGAAGAAGCTTTCGACCTCTGGAACGAATG<br>CGCCAAAGCCTGCGTGCTCGACCTCAAGGA<br>CGGCGTGCGTTCCAGCCGCATGAGCGTCGA<br>GCACCACCACCACCACCACTGAGATCCGGC<br>TGCTAAC |

6-3. Plasmid Construction of the Epithelial Cell Targeting Polypeptides

L2-200 of targeting ligand DNA was ligated into EcoR1 and XhoI restriction enzymes digested pPE49-3/pET plasmid. Plasmid containing insert was respectively transformed into *E. coli* and clones selected for by ampicillin resistance. The partial DNA sequences of the insertion portion of pL2-200 plasmid are shown in Table 16.

TABLE 16

| Plasmid name | SEQ ID NO. | DNA sequence |
|---|---|---|
| pP49-3-L2-200 | 30 | GTTTAACTTTAAGAAGGAGATATACCATGGC<br>CGAACAATTGGTGGACCTCTGGAACGAATG<br>CGCCAAAGCCTGCGTGCTCGACCTCAAGGA<br>CGGCGTGCGTTCCAGCCGCATGAGCGTCGA<br>CCCGGCCATCGCCGACACCAACGGCCAGG<br>GCGTGCTGCACTACTGCATGGAATTCCATAT<br>GGTCGACGGTATGTCCATCCGTGCTAAAC<br>GTCGTAAACGTGCTTCCGCTACCCAGCT<br>GTACAAAACCTGCAAACAGGCTGGTACC<br>TGCCCGCCGGACATCATCCCGAAAGTTG<br>AAGGTAAAACCATCGCTGAACAGATCCT<br>GCAATACGGTTCTATGGGTGTTTTCTTCG<br>GCGGTCTGGGCATCGGTACCGGTTCCGG<br>TACTGGCGGTCGTACCGGTTACATCCCG<br>CTGGGTACCCGTCCGCCGACCGCTACCG<br>ACACCCTGGCTCCGGTTCGTCCGCCGCT<br>GACCGTTGACCCGGTTGGTCCGTCCGAC<br>CCGTCCATCGTTTCCCTGGTTGAAGAAA<br>CCTCCTTCATCGACGCTGGTGCTCCGAC<br>CTCCGTTCCGTCCATCCCGCCGGACGTT<br>TCCGGTTTCTCCATCACCACCTCCACCG<br>ACACTACCCCGGCTATCCTGGACATCAAC<br>AACAACACCGTTACTACCGTAACCACTCA<br>CAACAACCCGACCTTCACCGACCCGTCC<br>GTTCTGCAACCGCCGACCCCGGCTGAAA<br>CCGGTGGTCACTTCACCCTGTCCTCTTC<br>CACCATCTCCACCCACAACTACGAAGAA<br>ATCCCGATGGACACCAAAGACGAACTGC<br>TCGAGCATATGGCCGAAGAAGCTTTCGACCT<br>CTGGAACGAATGCGCCAAAGCCTGCGTGCT<br>CGACCTCAAGGACGGCGTGCGTTCCAGCCG<br>CATGAGCGTCGAGCACCACCACCACCACCA<br>CTGAGATCCGGCTGCTAAC |

6-4. Preparation of the Expressed Mucosa Targeting Fused Polypeptides

The chimeric polypeptides had expression in *E. coli*, BL21(DE3) system. Codon substitutions without altering the original amino acid sequence of the selected peptide segment were made for avoiding spurious restriction sites and for optimal expression in *E. coli*. Restriction site linkers were added at the ends of the peptide segment-encoding DNA sequence for insertion into the expression vector.

7. Plasmid Constructions and Preparations of the Recombinant PE-Based Fused Antigens and Immune Enhancers

7-1. PE-Based Chimeric Antigens Construct

Two DNA fragments (E601; SEQ ID NO. 13, and E701; SEQ ID NO. 15) of HPV Th1-antigenic epitopes were respectively ligated into EcoR1 and XhoI restriction enzymes digested pPE425 plasmids (PE toxoid vector derivative plasmids) so that the fusion protein was added at the PE(ΔIII) fragment C-terminal. Plasmids containing inserts were respectively transformed into *E. coli* and clones selected for by ampicillin resistance.

Two DNA fragment (M14; SEQ ID NO. 19, and M27; SEQ ID NO. 20) of the Myostatin epitope was ligated into EcoR1 and XhoI restriction enzymes digested pPE407 plasmids.

Three DNA fragments (GP317; SEQ ID NO. 24, GP417; SEQ ID NO 25, and GP437; SEQ ID NO. 26) of PRRSV epitopes were respectively ligated into EcoR1 and XhoI restriction enzymes digested pPE425 plasmids (pET and PE toxoid vector derivative plasmids) so that the fusion protein was added at the PE(ΔIII) fragment C-terminal. Plasmids containing inserts were respectively transformed into *E. coli* and clones selected for by ampicillin resistance.

TABLE 17

The examples of the PE-based recombinant chimeric antigens

| Groups | SEQ ID NO. | Name of PE-based chimeric antigen |
|---|---|---|
| HPV E601, E701 | 31<br>32 | PE-E601<br>PE-E701 |
| M14, M27 | 33<br>34 | PE-M14<br>PE-M27 |
| GP317 | 35 | PE-GP317 |
| GP417 | 36 | PE-GP417 |
| GP437 | 37 | PE-GP437 |

| SEQ ID NO. | Name of peptide | Amino acid codon |
|---|---|---|
| 31 | PE-E601 | MGSSHHHHHHSSGLVPRGSHMAEEAFDLW<br>NECAKACVLDLKDGVRSSRMSVDPAIADTN<br>GQGVLHYSMVLEGGNDALKLAIDNALSITS<br>DGLTIRLEGGVEPNKPVRYSYTRQARGSWS<br>LNWLVPIGHEKPSNIKVFIHELNAGNQLSHM<br>SPIYTIEMGDELLAKLARDATFFVRAHESNE<br>MQPTLAISHAGVSVVMAQTQPRREKRWSE<br>WASGKVLCLLDPLDGVYNYLAQQRCNLDD<br>TWEGKIYRVLAGNPAKHDLIIKPTVISHRLH<br>FPEGGSLAALTAHQACHLPLETFTRHRQPRG<br>WEQLEQCGYPVQRLVALYLAARLSWNQVD<br>QVIRNALASPGSGGDLGEAIREQPEQARLAL<br>TLAAAESERFVRQGTGNDEAGAANADVVS<br>LTCPVAAGECAGPADSGDALLERNYPTGAE<br>FLGDGGDVSFSTRGTQNWTVERLLQA**EF**QL<br>LRREVFCGFRDLVYDFAFSDLKLPQLCTELK<br>LPQLCTELKDEL**LE**HHHHHH* |
| 32 | PE-E701 | MGSSHHHHHHSSGLVPRGSHMAEEAFDLW<br>NECAKACVLDLKDGVRSSRMSVDPAIADTN<br>GQGVLHYSMVLEGGNDALKLAIDNALSITS<br>DGLTIRLEGGVEPNKPVRYSYTRQARGSWS<br>LNWLVPIGHEKPSNIKVFIHELNAGNQLSHM<br>SPIYTIEMGDELLAKLARDATFFVRAHESNE<br>MQPTLAISHAGVSVVMAQTQPRREKRWSE<br>WASGKVLCLLDPLDGVYNYLAQQRCNLDD<br>TWEGKIYRVLAGNPAKHDLDIKPTVISHRLH<br>FPEGGSLAALTAHQACHLPLETFTRHRQPRG<br>WEQLEQCGYPVQRLVALYLAARLSWNQVD<br>QVIRNALASPGSGGDLGEAIREQPEQARLAL<br>TLAAAESERFVRQGTGNDEAGAANADVVS<br>LTCPVAAGECAGPADSGDALLERNYPTGAE<br>FLGDGGDVSFSTRGTQNWTVERLLQA**EF**Q<br>AEPDQAEPDRARAHYNIRARAHYNLEAHY<br>NIVIFRAHYNIVIF**LE**HHHHHH* |
| 33 | PE-M14 | MGSSHHHHHHSSGLVPRGSHMAEEAFDLW<br>NECAKACVLDLKDGVRSSRMSVDPAIADTN<br>GQGVLHYSMVLEGGNDALKLAIDNALSITS<br>DGLTIRLEGGVEPNKPVRYSYTRQARGSWS<br>LNWLVPIGHEKPSNIKVFIHELNAGNQLSHM<br>SPIYTIEMGDELLAKLARDATFFVRAHESNE<br>MQPTLAISHAGVSVVMAQTQPRREKRWSE<br>WASGKVLCLLDPIDGVYNYLAQQRCNLDD<br>TWEGKIYRYLAGNPAKHDLDIKPTVISHRLH<br>FPEGGSLAALTAHQACHLPLETFTRHRQPRG<br>WEQLEQCGYPVQRLVALYLAARLSWNQVD<br>QVIRNALASPGSGGDLGEAIREQPEQARLAL<br>TLAAAESERFVRQGTGNDEAGAANADVVS<br>LTCPVAAGECAGPADSGDALLERNYPTGAE<br>FLGDGGDV**EF**VFLQKYPHTHLVHQALDVFL<br>QKYPHTHLVHQALDVFLQKYPHTHLVHQA<br>LDVFLQKYPHTHLVHQAL**E**HHHHHH* |
| 34 | PE-M27 | MGSSHHHHHHSSGLVPRGSHMAEEAFDLW<br>NECAKACVLDLKDGVRSSRMSVDPAIADTN<br>GQGVLHYSMVLEGGNDALKLAIDNALSITS<br>DGLTIRLEGGVEPNKPVRYSYTRQARGSWS<br>LNWLVPIGHEKPSNIKVFIHELNAGNQLSHM<br>SPIYTIEMGDELLAKLARDATFFVRAHESNE<br>MQPTLAISHAGVSVVMAQTQPRREKRWSE<br>WASGKVLCLLDPLDGVYNYLAQQRCNLDD<br>TWEGKIYRVLAGNPAKHDLDIKPTVISHRLH<br>FPEGGSLAALTAHQACHLPLETFTRHRQPRG<br>WEQLEQCGYPVQRLVALYLAARLSWNQVD<br>QVIRNALASPGSGGDLGEAIREQPEQARLAL<br>TLAAAESERFVRQGTGNDEAGAANADVVS<br>LTCPVAAGECAGPADSGDALLERNYPTGAE<br>FLGDGGDV**EF**LLEPHTHLVHQANVLLALQL<br>LLEDREFVFLQKYPHVEPHTHLVHQANVLL<br>ALQLLLEDREFVFLQKYPHVEPHTHLVHQA<br>NVLLALQLLLEDREFVFLQKYPHVEPHTHL<br>VHQANVLLALQLLLEDREFVFLQKYPHVEP<br>HTHLVHQANVLLALQLLLEDREFVFLQKYP<br>HVEPHTHLVHQANVLLALQLLLEDREFVFL<br>QKYPHVEPHTHLVHQANVLLALQLLLEDRE<br>FVFLQKYPHVEPHTHLVHQANVLLALQLLL<br>EDREFVFLQKYPHV**E**HHHHHH* |
| 35 | PE-GP317 | MGSSHHHHHHSSGLVPRGSHMAEEAFDLW<br>NECAKACVLDLKDGVRSSRMSVDPAIADTN<br>GQGVLHYSMVLEGGNDALKLAIDNALSITS<br>DGLTIRLEGGVEPNKPVRYSYTRQARGSWS<br>LNWLVPIGHEKPSNIKVFIHELNAGNQLSHM<br>SPIYTIEMGDELLAKLARDATFFVRAHESNE<br>MQPTLAISHAGVSVVMAQTQPRREKRWSE<br>WASGKVLCLLDPLDGVYNYLAQQRCNLDD<br>TWEGKIYRVLAGNPAKHDLDIKPTVISHRLH<br>FPEGGSLAALTAHQACHLPLETFTRHRQPRG<br>WEQLEQCGYPVQRLVALYLAARLSWNQVD<br>QVIRNALASPGSGGDLGEAIREQPEQARLAL<br>TLAAAESERFVRQGTGNDEAGAANADVVS<br>LTCPVAAGECAGPADSGDALLERNYPTGAE<br>FLGDGGDVSFSTRGTQNWTVERLLQA**EF**VS<br>FSTGGSQNWTVERLLQAEFCSTSQAARQRL<br>ETGRNCSTGQAARQRLEPGRNLVLCLTSQA<br>AQQRLEPGGNCQTSQAAHQRLEPGRNCRTS<br>QAASQRLEPGRNCRTSQAAHQRLEPGRNCS<br>TRQAAQQRLEPGRNLLCPTSQAAHQRRLEP<br>GRNCSTSQAAYQRLEPGRNCPTSRAARQRL<br>EPGRNLLCSTSQAALQRLEPGRNLCPTSQA<br>AKQRLEPGRNLVVCLTSQAARQRLEPGRNC<br>STSQAASQRLEPGRNCPTSQAARQRLEPGR<br>NVLLLCLTSQAAHQRLEPGRN**LE**HHHHHH* |
| 36 | PE-GP417 | MGSSHHHHHHSSGLVPRGSHMAEEAFDLW<br>NECAKACVLDLKDGVRSSRMSVDPAIADTN<br>GQGVLHYSMVLEGGNDALKLAIDNALSITS<br>DGLTIRLEGGVEPNKPVRYSYTRQARGSWS<br>LNWLVPIGHEKPSNIKVFIHELNAGNQLSHM<br>SPIYTIEMGDELLAKLARDATFFVRAHESNE<br>MQPTLAISHAGVSVVMAQTQPRREKRWSE<br>WASGKVLCLLDPLDGVYNYLAQQRCNLDD<br>TWEGKIYRVLAGNPAKHDLDIKPTVISHRLH<br>FPEGGSLAALTAHQACHLPLETFTRHRQPRG<br>WEQLEQCGYPVQRLVALYLAARLSWNQVD<br>QVIRNALASPGSGGDLGEAIREQPEQARLAL<br>TLAAAESERFVRQGTGNDEAGAANADVVS<br>LTCPVAAGECAGPADSGDALLERNYPTGAE<br>FLGDGGDVSFSTRGTQNWTVERLLQA**EF**G<br>VSAAQEKISFGLLGVPTAQETTSIREVLEVST |

TABLE 17-continued

TABLE 17-continued

The examples of the PE-based recombinant chimeric antigens

| | | |
|---|---|---|
| | | AQENSPFMLGASAFEEKTSLRLGASTTQETS<br>FGKCLRPHGVSAAQGTTPFRGVSTTQENTS<br>FGRVPTAQENVSFGLHGVPAAQKTNSFGGV<br>PTAQENISFKEVSATQREIPFRCLRPHGVSTA<br>QETPFRGVSTAQETIPFRGVSATHENISFGCL<br>RPHGVSAAQESIPIRLGASAAQENTSFRGTP<br>AAQEKIP**LE**HHHHHH* |
| 37 | PE-GP437 | MGSSHHHHHHSSGLVPRGSHMAEEAFDLW<br>NECAKACVLDLKDGVRSSRMSVDPAIADTN<br>GQGVLHYSMVLEGGNDALKLAIDNALSITS<br>DGLTIRLEGGVEPNKPVRYSYTRQARGSWS<br>LNWLVPIGHEKPSNIKVFIHELNAGNQLSHM<br>SPIYTIEMGDELLAKLARDATFFVRAHESNE<br>MQPTLAISHAGVSVVMAQTQPRREKRWSE<br>WASGKVLCLLDPLDGVYNYLAQQRCNLDD<br>TWEGKIYRVLAGNPAKHDLDIKPTVISHRLH<br>FPEGGSLAALTAHQACHLPLETFTRHRQPRG<br>WEQLEQCGYPVQRLVALYLAARLSWNQVD<br>QVIRNALASPGSGGDLGEAIREQPEQARLAL<br>TLAAAESERFVRQGTGNDEAGAANADVVS<br>LTCPVAAGECAGPADSGDALLERNYPTGAE<br>FLGDGGDVSFSTRGTQNWTVERLLQA**EF**LG<br>VSAAQERIPIREVSADKEVSAEKKEISFGVST<br>AQGNISFGLGVSTAQEAIPFLALGVSTAQETI<br>PFGLLGVSTAQGIISFGGVSTAQENISFGGVS<br>TAQETISFGLLGVSTAQENISFGCLRTHEVSA<br>AQEKISFGGVSEAQKISFGVSAAGVSAAQEE<br>IPFGCLRPHGLPAAQEKTSFGGVSAAQEKTS<br>FGGVSAAQEEFSFGCLRPHRVSAAQEKISFE<br>VSALEVSAAQEKISFGVSAALGVSAAQEKN<br>SFGCLRPHGVSAAQEKTSFGGVSAAQKKISF<br>G**LE**HHHHHH* |

7-2. PE-Based HPV Fusion Polypeptides

To develop a PE-based HPV fusion protein as a vaccine, a reverse genetic engineering method was employed to construct a highly efficient, viral fusion protein expression vector. Through injection administration, the PE-based HPV vaccine can deliver the viral polypeptides into cells including antigen presenting cells (APCs) to elicit a strong immune response (Liao; Cancer research 2005). Thus, the strategy for developing a PE-based fusion polypeptide was also to fuse the C-terminus of the PE fragment with a viral protein Th1 epitope such as E601 and E701 polypeptides from HPV type 16 as shown in Table 6. However, any other types of HPV (e.g., type 18, type 35 and any other HPV types) can also be used as the HPV antigenic epitope.

Four DNA fragments (E601, E622, E701, and E713) of HPV antigens Th1-epitope were respectively ligated into EcoR1 and XhoI restriction enzymes digested pPE425 plasmids (pET23a and PE toxoid vector derivative plasmids) so that the fusion protein was added at the PE(ΔIII) fragment C-terminal. Plasmids containing inserts were respectively transformed into *E. coli* and clones selected for by ampicillin resistance.

All synthesized and/or subcloning nucleotide fragments were analyzed by restriction enzyme cutting and electrophoresis to check if they were of the expected sizes and right cutting sites. Once a sample had been obtained, DNA sequences were produced automatically by machine and the result displayed on computer. Sequence analysis performed to identify the sequence of nucleotides in a nucleic acid, or amino acids in a polypeptide.

7-3. PE-Based Myostatin Epitopes Fused Polypeptides Construct

The strategy of developing a PE-based fusion protein was to fuse the C-terminus of the PE fragment with a myostatin protein binding epitope (M14) to elicit anti-Myostatin antibodies for blocking the activity of myostatin.

Two DNA fragments (M27, M14) of Myostatin binding epitope were respectively ligated into EcoR1 and XhoI restriction enzymes digested pPE407 plasmids (pET23a and PE toxoid vector derivative plasmids) so that the fusion protein was added at the PE(ΔIII) fragment C-terminal. Plasmids containing inserts were respectively transformed into *E. coli* and clones selected for by ampicillin resistance. Once a sample had been obtained, DNA sequences were produced automatically by machine and the result displayed on computer. Sequence analysis performed to identify the sequence of nucleotides in a nucleic acid, or amino acids in a polypeptide.

7-4. PE-Based GP3 and GP4 Fused Polypeptides Construct

The strategy of developing a PE-based fusion protein was to fuse the C-terminus of the PE fragment with virus serum neutralization epitopes (GP3 and GP4) to elicit antibodies against PRRSV infection.

The DNA fragments (GP317, GP417, and GP437) were respectively ligated into EcoR1 and XhoI restriction enzymes digested pPE425 plasmids (pET23a and PE toxoid vector derivative plasmids) so that the fusion protein was added at the PE(ΔIII) fragment C-terminal. Plasmids containing inserts were respectively transformed into *E. coli* and clones selected for by ampicillin resistance. Once a sample had been obtained, DNA sequences were produced automatically by machine and the result displayed on computer. Sequence analysis performed to identify the sequence of nucleotides in a nucleic acid, or amino acids in a polypeptide.

8. Plasmid Construction of the PE-Based Mucosal Targeting Fused Peptides

All the constructed plasmids, as shown in Table 18, are belonged to the fusion biogenic polypeptides, which can serve an immune enhance functions through the mucosal targeting and Th1 immuno-proteasome processing.

The larger DNA fragment containing DQ2 epitope was cleaved from pP49-3-DQ2 plasmid with HindIII and Pst1, followed by respectively ligating into various DNA fragments, which containing PE and Th1 epitope plasmids, such as pPE-E713, pPE-E622, pPE-M14, pPE-M37, pPE-GP317, pPE-GP417 and pPE-GP437. Those new plasmids containing DQ2 epitope were cleaved with Mfe1 and HindIII and then exchanged other two DNA fragments (P493-CO1, and RV3). The larger DNA fragment containing HPV epithelial cell targeting epitope was cleaved from pP49-3-L2-200 plasmid with HindIII and Pst1, followed by ligating with HindIII and Pst1 restriction enzymes digested pPE-E713 or pPE-E622 plasmid which containing PE with HPV Th1 epitope.

TABLE 18

The examples of the fusion biogenic polypeptides for immune enhance functions

| Group | Name of immune enhancer |
|---|---|
| HPV E6 and E7 Th1-epiopes: E622, E713 | CO1-PE-E622, CO1-PE-E713<br>DQ2-PE-E622, DQ2-13E-E713<br>RV3-PE-E622, IW3-PE-E713<br>L2-200-PE-E662, L2-200-PE-E713 |

TABLE 18-continued

The examples of the fusion biogenic polypeptides for immune enhance functions

| | |
|---|---|
| Myostatin-like polypeptide: M27, M14 | CO1-PE-M27, CO1-PE-M14 DQ2-PE-M27, DQ2-PE-M14 RV3-PE-M27, RV3-PE-M14 |
| PRRSV VN-epitopes: GP417, GP437, GP317 | DQ2-PE-GP417, DQ2-PE-GP437 DQ2-PE-GP317 |

| SEQ ID NO. | Name of peptide | amino acid codon |
|---|---|---|
| 38 | CO1-PE-E622 | MAEQLVDLWNECAKACVLDLKDCWRSSRMSVDPAIADTNGQGVLHYCMEFSFHQLPARSPAPLQLEHMAEEAFDLWNECAKACVLDLKDGVRSSRMSVDPAIADTNGQGVLHYSMVLEGGNDALKLAIDNALSITSDGLTIRLEGGVEPNKPVRYSYTRQARGSWSLNWLVPIGHEKPSNIKVFIHELNAGNQLSHMSPIYTIEMGDELLAKLARDATFFVRAHESNEMQPTLAISHAGVSVVMAQTQPRREKRWSEWASGKVLCLLDPLDGVYNYLAQQRCNLDDTWEGKIYRVLAGNPAKHDLDIKPTVISHRLHFPEGGSLAALTAHQACHLPLETFTRHRQPRGWEQLEQCGYPVQRLVALYLAARLSWNQVDQVIRNALASPGSGGDLGEAIREQPEQARLALTLAAAESERFVRQGTGNDEAGAANADVVSLTCPVAAGECAGPADSGDALLERNYPTGAEFLGDGGDVSFSTRGTQNWTVERLLQA*EFVD*KDEL**REVYNFAFLLVLRREVYDK**DELLLLLEDR**QLLRREVFCGFRDL**LEDR**VYDFAFSDLKLPQLCTELKLPQLCTEL**KDELKDELVLLL*LE*HHHHHH* |
| 39 | DQ2-PE-E622 | MAEQLVDLWNECAKACVLDLKDGVRSSRMSVDPAIADTNGQGVLHYCMEFSSFHLFHHLPARAPLAPSELQPLEHMAEEAFDLWNECAKACVLDLKDGVRSSRMSVDPAIADTNGQGVLHYSMVLEGGNDALKLAIDNALSITSDGLTIRLEGGVEPNKPVRYSYTRQARGSWSLNWLVPIGHEKPSNIKVFIHELNAGNQLSHMSPIYTIEMGDELLAKLARDATFFVRAHESNEMQPTLAISHAGVSVVMAQTQPRREKRWSEWASGKVLCLLDPLDGVYNYLAQQRCNLDDTWEGKIYRVLAGNPAKHDLDIKPTVISHRLHFPEGGSLAALTAHQACHLPLETFTRHRQPRGWEQLEQCGYPVQRLVALYLAARLSWNQVDQVIRNALASPGSGGDLGEAIREQPEQARLALTLAAAESERFVRQGTGNDEAGAANADVVSLTCPVAAGECAGPADSGDALLERNYPTGAEFLGDGGDVSFSTRGTQNWTVERLLQA*EFVD*KDEL**REVYNFAFLLVLRREVYDK**DELLLLLEDR**QLLRREVFCGFRDL**LEDR**VYDFAFSDLKLPQLCTELKLPQLCTEL**KDELKDELVLLL*LE*HHHHHH* |
| 40 | RV3-PE-E622 | MAEQLVDLWNECAKACVLDLKDGVRSSRMSVDPAIADTNGQGVLHYCMEFSTPFHPLPARKPLPLVPLEHMAEEAFDLWNECAKACVLDLKDGVRSSRMSVDPAIADTNGQGVLHYSMVLEGGNDALKLAIDNALSITSDGLTIRLEGGVEPNKPVRYSYTRQARGSWSLNWLVPIGHEKPSNIKVFIHELNAGNQLSHMSPIYTIEMGDELLAKLARDATFFVRAHESNEMQPTLAISHAGVSVVMAQTQPRREKRWSEWASGKVLCLLDPLDGVYNYLAQQRCNLDDTWEGKIYRVLAGNPAKHDLDIKPTVISHRLHFPEGGSLAALTAHQACHLPLETFTRHRQPRGWEQLEQCGYPVQRLVALYLAARLSWNQVDQVIRNALASPGSGGDLGEAIREQPEQARLALTLAAAESERFVRQGTGNDEAGAANADVVSLTCPVAAGECAGPADSGDALLERNYPTGAEFLGDGGDVSFSTRGTQNWTVERLLQA*EFVD*KDEL**REVYNFAFLLVLRREVYDK**DELLLLLEDR**QLLRREVFCGFRDL**LEDR**VYDFAFSDLKLPQLCTELKLPQLCTEL**KDELKDELVLLL*LE*HHHHHH* |
| 41 | L2-200-PE-E662 | **MAEQLVDLWNECAKACVIDLKDGVRSSRMSVDPAIADTNGQGVLHYCMEF***HM***VD**GMSIRAKRRKRASATQLYKTCKQAGTCPPDIIPKVEGKTIAEQILQYGSMGVFFGGLGIGTGSGTGGRTGYIPLGTRPPTATDTLAPVRPPLTVDPVGPSDPSIVSLVEETSFIDAGAPTSVPSIPPDVSGFSITTSTDTTPAILDINNNTVTTVTTHNNPTFTDPSVLQPPTPAETGGHFTLSSSTISTHNYEEIPMDTKDELLEHMAEEAFDLWNECAKACVLDLKDGVRSSRMSVDPAIADTNGQGVLHYSMVLEGGNDALKLAIDNALSITSDGLTIRLEGGVEPNKPVRYSYTRQARGSWSLNWLVPIGHEKPSNIKVFIHELNAGNQLSHMSPIYTIEMGDELLAKLARDATFFVRAHESNEMQPTLAISHAGVSVVMAQTQPRREKRWSEWASGKVLCLLDPLDGVYNYLAQQRCNLDDTWEGKIYRVLAGNPAKHDLDIKPTVISHRLHFPEGGSLAALTAHQACHLPLETFTRHRQPRGWEQLEQCGYPVQRLVALYLAARLSWNQVDQVIRNALASPGSGGDLGEAIREQPEQARLALTLAAAESERFVRQGTGNDEAGAANADVVSLTCPVAAGECAGPADSGDALLERNYPTGAEFLGDGGDVSFSTRGTQNWTVERLLQA*EFVD*KDEL**REVYNFAFLLVLRREVYDK**DELLLLLEDR**QLLRREVFCGFRDL**LEDR**VYDFAFSDLKLPQLCTELKLPQLCTEL**KDELKDELVLLL*LE*HHHHHH* |
| 42 | CO1-PE-E713 | MAEQLVDLWNECAKACVLDLKDGVRSSRMSVDPAIADTNGQGVIEYCMEFSFHQLPARSPAPLQLEHMAEEAFDLWNECAKACVLDLKDGVRSSRMSVDPAIADTNGQGVLHYSMVLEGGNDALKLAIDNALSITSDGLTIRLEGGVEPNKPVRYSYTRQARGSWSLNWLVPIGHEKPSNIKVFIHELNAGNQLSHMSPIYTIEMGDELLAKLARDATFFVRAHESNEMQPTLAISHAGVSVVMAQTQPRREKRWSEWASGKVLCLLDPLDGVYNYLAQQRCNLDDTWEGKIYRVLAGNPAKHDLDIKPTVISHRLHFPEGGSLAALTAHQACHLPLETFTRHRQPRGWEQLEQCGYPVQRLVALYLAARLSWNQVDQVIRNALASPGSGGDLGEAIREQPEQARLALTLAAAESERFVRQGTGNDEAGAANADVVSLTCPVAAGECAGPADSGDALLERNYPTGAEFLGDGGDVSFSTRGTQNWTVERLLQA*EFVD***QAEPDQAEPDRDELVLRARAHYNIRARAHYNIL**EDRLLVL**RAHYNIVIFRAHYNIVIF**KDELLV*LE*HHHHHH* |
| 43 | DQ2-PE-E713 | MAEQLVDLWNECAKACVLDLKDGVRSSRMSVDPAIADTNGQGVLHYCMEFSSFHLFHHLPARAPLAPSELQPLEHMAEEAFDLWNECAKACVLDLKDGVRSSRMSVDPAIADTNGQGVLHYSMVLEGGNDALKLAIDNALSITSDGLTIRLEGGVEPNKPVRYSYTRQARGSWSLNWLVPIGHEKPSNIKVFIHELNAGNQLSHMSPIYTIEMGDELLAKLARDATFFVRAHESNEMQPTLAISHAGVSVVMAQTQPRREKRWSEWASGKVLCLLDPLDGVYNYLAQQRCNLDDTWEGKIYRVLAGNPAKHDLDIKPTVISHRLHFPEGGSLAALTAHQACHLPLETFTRHRQPRGWEQLEQCGYPVQRLVALYLAARLSWNQVDQVIRNALASPGSGGDLGEAIREQPEQARLALTLAAAESERFVRQGTGNDEAGAANADVVSLTCPVAAGECAGPADSGDALLERNYPTGAEFLGDGGDVSFSTRGTQNWTVERLLQA*EFVD***Q** |

TABLE 18-continued

The examples of the fusion biogenic polypeptides for immune enhance functions

| | | |
|---|---|---|
| | | AEPDQAEPDRDELVLRARAHYNIRARAHYNILEDRLLVLRAHYNIVIFRAHYNIVIFKDELLVLEHHHHHH* |
| 44 | RV-3-PE-E713 | MAEQLVDLWNECAKACVLDLKDGVRSSRMSVDPAIADTNGQGVLHYCMEFSTPFHPLPARKPLPLVPLEHMAEEAFDLWNECAKACVLDLKDGVRSSRMSVDPAIADTNGQGVLHYSMVLEGGNDALKLAIDNALSITSDGLTIRLEGGVEPNKPVRYSYTRQARGSWSLNWLVPIGHEKPSNIKVFIHELNAGNQLSHMSPIYTIEMGDELLAKLARDATFFVRAHESNEMQPTLAISHAGVSVVMAQTQPRREKRWSEWASGKVLCLLDPLDGVYNYLAQQRCNLDDTWEGKIYRVLAGNPAKHDLDIKPTVISHRLHFPEGGSLAALTAHQACHLPLETFRHRQPRGWEQLEQCGYPVQRLVALYLAARLSWNQVDQVIRNALASPGSGGDLGEAIREQPEQARLALTLAAAESERFVRQGTGNDEAGAANADVVSLTCPVAAGECAGPADSGDALLERNYPTGAEFLGDGGDVSFSTRGTQNWTVERLLQAEFVDQAEPDQAEPDRDELVLRARAHYNIRARAHYNILEDRLLVLRAHYNIVIFRAHYNIVIFKDELLVLEHHHHHH* |
| 45 | L2-200-PE-E713 | MAEQLVDLWNECAKACVLDLKDGVRSSRMSVDPAIADTNGQGVLHYCMEFHMVDGMSIRAKRRKRASATQLYKTCKQAGTCPPDIIPKVEGKTIAEQILQYGSMGVFFGGLGIGTGSGTGGRTGYIPLGTRPPTATDTLAPVRPPLIVDPVGPSDPSIVSLVEETSFIDAGAPTSVPSIPPDVSGFSITTSTDTTPAILDINNNTVTTVTTHNNPTFTDPSVLQPPTPAETGGHFTLSSSTISTHNYEEIPMDTKDELLEHMAEEAFDLWNECAKACVLDLKDGVRSSRMSVDPAIADTNGQGVLHYSMVLEGGNDALKLAIDNALSITSDGLTIRLEGGVEPNKPVRYSYTRQARGSWSLNWLVPIGHEKPSNIKVFIHELNAGNQLSHMSPIYTIEMGDELLAKLARDATFFVRAHESNEMQPTLAISHAGVSVVMAQTQPRREKRWSEWASGKVLCLLDPLDGVYNYLAQQRCNLDDTWEGKIYRVLAGNPAKHDLDIKPTVISHRLHFPEGGSLAALTAHQACHLPLETFTRHRQPRGWEQLEQCGYPVQRLVALYLAARLSWNQVDQVIRNALASPGSGGDLGEMIREQPEQARLALTLAAAESERFVRQGTGNDEAGAANADVVSLTCPVAAGECAGPADSGDALLERNYPTGAEFLGDGGDVSFSTRGTQNWTVERLLQAEFVDQAEPDQAEPDRDELVLRARAHYNIRARAHYNILEDRLLVLRAHYNIVIFRAHYNIVIFKDELLVLEHHHHHH* |
| 46 | CO1-PE-M14 | MAEQLVDLWNECAKACVLDLKDGVRSSRMSVDPAIADTNGQGVLHYCMEFSFHQLPARSPAPLQLEHMAEEAFDLWNECAKACVLDLKDGVRSSRMSVDPAIADTNGQGVLHYSMVLEGGNDALKLAIDNALSITSDGLTIRLEGGVEPNKPVRYSYTRQARGSWSLNWLVPIGHEKPSNIKVFIHELNAGNQLSHMSPIYTIEMGDELLAKLARDATFFVRAHESNEMQPTLAISHAGVSVVMAQTQPRREKRWSEWASGKVLCLLDPLDGVYNYLAQQRCNLDDTWEGKIYRVLAGNPAKHDLDIKPTVISHRLHFPEGGSLAALTAHQACHLPLETFTRHRQPRGWEQLEQCGYPVQRLVALYLAARLSWNQVDQVIRNALASPGSGGDLGEAIREQPEQARLALTLAAAESERFVRQGTGNDEAGAANADVVSLTCPVAAGECAGPADSGDALLERNYPTGAEFLGDGGDVEFVDVFLQKYPHTHLVHQALDVFLQKYPHTHLVHQALDVFLQKYPHTHLVHQALDVFLQKYPHTHLVHQALEHHHHHH* |
| 47 | DQ2-PE-M14 | MAEQLVDLWNECAKACVLDLKDGVRSSRMSVDPAIADTNGQGVLHYCMEFSSFHLFHHLPARAPLAPSELQPLEHMAEEAFDLWNECAKACVLDLKDGVRSSRMSVDPAIADTNGQGVLHYSMVLEGGNDALKLAIDNALSITSDGLTIRLEGGVEPNKPVRYSYTRQARGSWSLNWLVPIGHEKPSNIKVFIHELNAGNQLSHMSPIYTIEMGDELLAKLARDATFFVRAHESNEMQPTLAISHAGVSVVMAQTQPRREKRWSEWASGKVLCLLDPLDGVYNYLAQQRCNLDDTWEGKIYRVLAGNPAKHDLDIKPTVISHRLHFPEGGSLAALTAHQACHLPLETFTRHRQPRGWEQLEQCGYPVQRLVALYLAARLSWNQVDQVIRNALASPGSGGDLGEAIREQPEQARLALTLAAAESERFVRQGTGNDEAGAANADVVSLTCPVAAGECAGPADSGDALLERNYPTGAEFLGDGGDVEFVDVFLQKYPHTHLVHQALDVFLQKYPHTHLVHQALDVFLQKYPHTHLVHQALDVFLQKYPHTHLVHQALEHHHHHH* |
| 48 | RV-3-PE-M14 | MAEQLVDLWNECAKACVLDLKDGVRSSRMSVDPAIADTNGQGVLHYCMEFSTPFHPLPARKPLPLVPLEHMAEEAFDLWNECAKACVLDLKDGVRSSRMSVDPAIADTNGQGVLHYSMVLEGGNDALKLAIDNALSITSDGLTIRLEGGVEPNKPVRYSYTRQARGSWSLNWLVPIGHEKPSNIKVFIHELNAGNQLSHMSPIYTIEMGDELLAKLARDATFFVRAHESNEMPTLAISHAGVSVVMAQTQPRREKRWSEWASGKVLCLLDPLDGVYNYLAQQRCNLDDTWEGKIYRVLAGNPAKHDLDIKPTVISHRLHFPEGGSLAALTAHQACHLPLETFTRHRQPRGWEQLEQCGYPVQRLVALYLAARLSWNQVDQVIRNALASPGSGGDLGEAIREQPEQARLALTLAAAESERFVRQGTGNDEAGAANADVVSLTCPVAAGECAGPADSGDALLERNYPTGAEFLGDGGDVEFVDVFLQKYPHTHLVHQALDVFLQKYPHTHLVHQALDVFLQKYPHTHLVHQALDVFLQKYPHTHLVHQALEHHHHHH* |
| 49 | CO1-PE-M27 | MAEQLVDLWNECAKACVLDLKDGVRSSRMSVDPAIADTNGQGVLHYCMEFSFHQLPARSPAPLQLEHMAEEAFDLWNECAKACVLDLKDGVRSSRMSVDPAIADTNGQGVLHYSMVLEGGNDALKLAIDNALSITSDGLTIRLEGGVEPNKPVRYSYTRQARGSWSLNWLVPIGHEKPSNIKVFIHELNAGNQLSHMSPIYTIEMGDELLAKLARDATFFVRAHESNEMQPTLAISHAGVSVVMAQTQPRREKRWSEWASGKVLCLLDPLDGVYNYLAQQRCNLDDTWEGKIYRVLAGNPAKHDLDIKPTVISHRLHFPEGGSLAALTAHQACHLPLETFTRHRQPRGWEQLEQCGYPVQRLVALYLAARLSWNQVDQVIRNALASPGSGGDLGEAIREQPEQARLALTLAAAESERFVRQGTGNDEAGAANADVVSLTCPVAAGECAGPADSGDALLERNYPTGAEFLGDGGDVEFLLEPHTHLVHQANVLLALQLLLEDREFVFLQKYPHVEPHTHLVHQANVLLALQLLLEDREFVFLQKYPHVEPHTHLVHQANVLLALQLLLEDREFVFLQKYPHVEPHTHLVHQANVLLALQLLLEDREFVFLQKYPHVEPHTHLVHQANVLLALQLLLEDREFVFLQKYPHVEPHTHLVHQANVLLALQLLLEDREFVFLQKYPHVEPHTHLVHQANVLLALQLLLEDREFVFLQKYPHVEHHHHHH* |
| 50 | DQ2-PE-M27 | MAEQLVDLWNECAKACVLDLKDGVRSSRMSVDPAIADTNGQGVLHYCMEFSSFHLFHHLPARAPLAPSELQPLEHMAEEAFDLWNECAKACVLDLKDGVRSSRMSVD |

TABLE 18-continued

The examples of the fusion biogenic polypeptides for immune enhance functions

| | | |
|---|---|---|
| | | PAIADTNGQGVLHYSMVLEGGNDALKL<br>AIDNALSITSDGLTIRLEGGVEPNKPVRYS<br>YTRQARGSWSLNWLVPIGHEKPSNIKVFI<br>HELNAGNQLSHMSPIYTIEMGDELLAKL<br>ARDATFFVRAHESNEMQPTLAISHAGVS<br>VVMAQTQPRREKRWSEWASGKVLCLLD<br>PLDGVYNYLAQQRCNLDDTWEGKIYRV<br>LAGNPAKHDLDIKPTVISHRLHFPEGGSL<br>AALTAHQACHLPLETFTRHRQPRGWEQL<br>EQCGYPVQRLVALYLAARLSWNQVDQVI<br>RNALASPGSGGDLGEAIREQPEQARLALT<br>LAAAESERFVRQGTGNDEAGAANADVV<br>SLTCPVAAGECAGPADSGDALLERNYPTG<br>AEFLGDGGDV*EF*LLEPHTHLVHQANVLL<br>ALQLLLEDREFVFLQKYPHVEPHTHLVH<br>QANVLLALQLLLEDREFVFLQKYPHVEP<br>HTHLVHQANVLLALQLLLEDREFVFLQK<br>YPHVEPHTHLVHQANVLLALQLLLEDRE<br>FVFLQKYPHVEPHTHLVHQANVLLALQL<br>LLEDREFVFLQKYPHVEPHTHLVHQANV<br>LLALQLLLEDREFVFLQKYPHVEPHTHLV<br>HQANVLLALQLLLEDREFVFLQKYPHVE<br>PHTHLVHQANVLLALQLLLEDREFVFLQ<br>KYPHV*E*HHHHHH* |
| 51 | RV3-<br>PE-<br>M27 | **MAEQLVDLWNECAKACVLDLKDGVRS**<br>**SRMSVDPAIADTNGQGVLHYCMEFSTP**<br>**FHPLPARKPLPLVPLEHMAEEA**FDLWN<br>ECAKACVLDLKDGVRSSRMSVDPAIADT<br>NGQGVLHYSMVLEGGNDALKLAIDNAL<br>SITSDGLTIRLEGGVEPNKPVRYSYTRQA<br>RGSWSLNWLVPIGHEKPSNIKVFIHELNA<br>GNQLSHMSPIYTIEMGDELLAKLARDATF<br>FVRAHESNEMQPTLAISHAGNSVVMAQT<br>QPRREKRWSEWASGKVLCLLDPLDGVY<br>NYLAQQRCNLDDTWEGKIYRVLAGNPA<br>KHDLDIKPTVISHRLHFPEGGSLAALTAH<br>QACHLPLETFTRHRQPRGWEQLEQCGYP<br>VQRLVALYLAARLSWNQVDQVIRNALAS<br>PGSGGDLGEAIREQPEQARLALTLAAAES<br>ERFVRQGTGNDEAGAANADVVSLTCPVA<br>AGECAGPADSGDALLERNYPTGAEFLGD<br>GGDV*EF*LLEPHTHLVHQANVLLALQLLL<br>EDREFVFLQKYPHVEPHTHLVHQANVLL<br>ALQLLLEDREFVFLQKYPHVEPHTHLVH<br>QANVLLALQLLLEDREFVFLQKYPHVEP<br>HTHLVHQANVLLALQLLLEDREFVFLQK<br>YPHVEPHTHLVHQANVLLALQLLLEDRE<br>FVFLQKYPHVEPHTHLVHQANVLLALQL<br>LLEDREFVFLQKYPHVEPHTHLVHQANV<br>LLALQLLLEDREFVFLQKYPHVEPHTHLV<br>HQANVLLALQLLLEDREFVFLQKYPHV*E*<br>HHHHHH* |
| 52 | DQ2-<br>PE-<br>GP317 | **MAEQLVDLWNECAKACVLDLKDGVRS**<br>**SRMSVDPAIADTNGQGVLHYCMEFSSF**<br>**HLFHHLPARAPLAPSELQPLEHMAEEA**<br>FDLWNECAKACVLDLKDGVRSSRMSVD<br>PAIADTNGQGVLHYSMVLEGGNDALKL<br>AIDNALSITSDGLTIRLEGGVEPNKPVRYS<br>YTRQARGSWSLNWLVPIGHEKPSNIKVFI<br>HELNAGNQLSHMSPIYTIEMGDELLAKL<br>ARDATFFVRAHESNEMQPTLAISHAGVS<br>VVMAQTQPRREKRWSEWASGKVLCLLD<br>PLDGVYNYLAQQRCNLDDTWEGKIYRV<br>LAGNPAKHDLDIKPTVISHRLHFPEGGSL<br>AALTAHQACHLPLETFTRHRQPRGWEQL<br>EQCGYPVQRLVALYLAARLSWNQVDQVI<br>RNALASPGSGGDLGEAIREQPEQARLALT<br>LAAAESERFVRQGTGNDEAGAANADVV<br>SLTCPVAAGECAGPADSGDALLERNYPTG<br>AEFLGDGGDVSFSTRGTQNWTVERLLQA<br>*EF*VSFSTGGSQNWTVERLLQAEFCSTSQ<br>AARQRLETGRNCSTGQAARQRLEPGRNL<br>VLCLTSQAAQQRLEPGGNCQTSQAAHQR<br>LEPGRNCRTSQAASQRLEPGRNCRTSQA<br>AHQRLEPGRNCSTRQAAQQRLEPGRNLL<br>CPTSQAAHQRRLEPGRNCSTSQAAYQRL<br>EPGRNCPTSRAARQRLEPGRNLLCSTSQA<br>ALQRLEPGRNLCPTSQAAKQRLEPGRNL<br>VVCLTSQAARQRLEPGRNCSTSQAASQR<br>LEPGRNCPTSQAARQRLEPGRNVLLLCLT<br>SQAAHQRLEPGRN*LE*HHHHHH* |
| 53 | DQ2-<br>PE-<br>GP417 | MAEQLVDLWNECAKACVLDLKDGVRSS<br>RMSVDPAIADTNGQGVLHYCMEFSSFHL<br>FHHLPARAPLAPSELQPLEHMAEEAFDL<br>WNECAKACVLDLKDGVRSSRMSVDPAI<br>ADTNGQGVLHYSMVLEGGNDALKLAID<br>NALSITSDGLTIRLEGGVEPNKPVRYSYTR<br>QARGSWSLNWLVPIGHEKPSNIKVFIHEL<br>NAGNQLSHMSPIYTIEMGDELLAKLARD<br>ATFFVRAHESNEMQPTLAISHAGVSVVM<br>AQTQPRREKRWSEWASGKVLCLLDPLDG<br>VYNYLAQQRCNLDDTWEGKIYRVLAGN<br>PAKHDLDIKPTVISHRLHFPEGGSLAALTA<br>HQACHLPLETFTRHRQPRGWEQLEQCGY<br>PVQRLVALYLAARLSWNQVDQVIRNALA<br>SPGSGGDLGEAIREQPEQARLALTLAAAE<br>SERFVRQGTGNDEAGAANADVVSLTCPV<br>AAGECAGPADSGDALLERNYPTGAEFLG<br>DGGDVSFSTRGTQNWTVERLLQA*EF*GVS<br>AAQEKISFGLLGVPTAQETTSIREVLEVST<br>AQENSPFMLGASATEEKTSLRLGASTTQE<br>TSFGKCLRPHGVSAAQGTTPFRGVSTTQE<br>NTSFGRVPTAQENVSFGLHGVPAAQKTN<br>SFGGVPTAQENISFKEVSATQREIPFRCLR<br>PHGVSTAQETPFRGVSTAQETIPFRGVSAT<br>HENISFGCLRPHGVSAAQESIPIRLGASAA<br>QENTSFRGTPAAQEKIP*LE*HHHHHH* |
| 54 | DQ2-<br>PE-<br>GP437 | MAEQLVDLWNECAKACVLDLKDGVRSS<br>RMSVDPAIADTNGQGVLHYCMEFSSFHL<br>FHHLPARAPLAPSELQPLEHMAEEAFDL<br>WNECAKACVLDLKDGVRSSRMSVDPAI<br>ADTNGQGVLHYSMVLEGGNDALKLAID<br>NALSITSDGLTIRLEGGVEPNKPVRYSYTR<br>QARGSWSLNWLVPIGHEKPSNIKVFIHEL<br>NAGNQLSHMSPIYTIEMGDELLAKLARD<br>ATFFVRAHESNEMQPTLAISHAGVSVVM<br>AQTQPRREKRWSEWASGKVLCLLDPLDG<br>VYNYLAQQRCNLDDTWEGKIYRVLAGN<br>PAKHDLDIKPTVISHRLHFPEGGSLAALTA<br>HQACHLPLETFTRHRQPRGWEQLEQCGY<br>PVQRLVALYLAARLSWNQVDQVIRNALA<br>SPGSGGDLGEAIREQPEQARLALTLAAAE<br>SERFVRQGTGNDEAGAANADVVSLTCPV<br>AAGECAGPADSGDALLERNYPTGAEFLG<br>DGGDVSFSTRGTQNWTVERLLQA*EF*LGV<br>SAAQERIPIREVSADKEVSAEKKEISFGVS<br>TAQGNISFGLGVSTAQEMIPFLALGVSTAQ<br>ETIPFGLLGVSTAQGIISFGGVSTAQENISF<br>GGVSTAQETISFGLLGVSTAQENISFGCLR<br>THEVSAAQEKISFGGVSEAQKISFGVSAA<br>GVSAAQEEIPFGCLRPHGLPAAQEKTSFG<br>GVSAAQEKTSFGGVSAAQEEFSFGCLRP<br>HRVSAAQEKISFEVSALEVSAAQEKISFG<br>VSAALGVSAAQEKNSFGCLRPHGVSAAQ<br>EKTSFGGVSAAQKKISFG*LE*HHHHHH* |

Among the fusion polypeptides shown in Table 18, the mucosa targeting polypeptide is located at an N-terminal of the fusion polypeptide, the antigenic epitope is located at a C-terminal of the fusion polypeptide, and the translocation peptide is located between the mucosa targeting polypeptide and the antigenic epitope. However, the present disclosure is not limited thereto. In other embodiments of the present disclosure, the translocating peptide is located at an N-terminal of the fusion polypeptide, the antigenic epitope is located at a C-terminal of the fusion polypeptide, and the mucosa targeting polypeptide is located between the translocating peptide and the antigenic epitope.

9. Fusion Polypeptide Expression and Purification

The plasmids, under the control of T7 promoter, were transformed into *E. coli* BL21 (DE3) for expression. After the induced expression of the recombinant polypeptides, the inclusion bodies in the lysates were recovered; inclusion granules were harvested from the insoluble fraction by differential centrifugation (1,450×g, 10 min). The pellet was then homogenized in TNE buffer (10 mM Tris-HCl pH7.5, 1 mM EDTA, 50 mM NaCl) containing 100 mM PMSF and 1 mg/ml DOC, and a further 1,450×g supernatant was collected. After three harvests, the pellets were collected from the combined supernatants by centrifugation (27,000×g, 20 min). Urea soluble contaminants were removed by re-suspending in three washes of 0.1 M Tris-HCl, pH 8.5 containing 1 M urea followed by centrifugation (27,000×g, 20 min). The final granule preparation was solubilized in 20 volumes of 8 M Urea in TNE, with gentle stirring for overnight at room temperature. The proteins were then purified by S200 gel filtration chromatography in denatured and reduced condition (10 mM DTT) with 6 M urea in TNE buffer. Protein elution fractions were renatured by dialysis against TNE buffers containing from 4 M to 0 M urea in a Pellicon device (Millipore, Billerica, Mass., USA).

The clones were grown up from 2 ml of glycerol storage stocks by inoculation into 500 ml flask containing 200 ml of LB with 500 μg/ml Ampicillin. The flasks were shaken at 150 rpm and 37° C., until the cultures had an $OD_{600}$ of 1.0±0.3. Aliquots of 50 ml were inoculated in each one of eight sterilized 3000 ml flasks containing 1250 ml LB fortified with 500 μg/ml of Ampicillin and 50 ml 10% glucose, incubated in a 37° C. rotating incubator and shaken at 150 rpm for 2-3 hours. IPTG was then added to a final concentration of 50 ppm, and the culture was incubated at 37° C. with shaking for another 2 hours to complete the protein induction. The chimeric peptides were quantified by densitometry of Coomassie Blue stained SDS-PAGE. 0.03±0.003 mg of chimeric polypeptides was used for high-dose administration, and 0.01±0.0001 mg was used for low-dose administration in the mice animal test. For each 10 liters of bacterial culture about 300-400 mg of polypeptides was obtained, which was sufficient for 3000-9000 administrations.

10. Preparation of Microspheres of Chimeric Antigens and Immune Enhancers for Oral Administration The Recombinant Polypeptides of Chimeric Antigens and Immune Enhancer Preparations The polypeptides production and sample preparation performed in a class 100 laminar flow. Each recombinant polypeptide solution was equivalent to 300 mg protein content. It was transferred in 3 L volumetric flask and then added 70-80 ml of 8M urea with powder carriers as described in Table 19.

Table 19 presents the microsphere formulations. Microsphere powders were prepared with a co-spray drying procedure using a Model L-8 device (Ohkawara Kakohki) as described in Liao et al. (2001). The spray drying process was set based on several manufacturing factors: atomizer speed at 30,000 rpm, feeding rate at 1 mL/min, hot air inlet temperature of 50° C., exhaust temperature of 35° C., and cyclone pressure of ~110 to 120 mm $H_2O$. Microspheres were stored at 4° C. (Liao et al., 2001).

TABLE 19

| The formulation of microsphere powder preparation | |
|---|---|
| 300 mg recombinant polypeptide solution in 8M urea | 80 ml |
| Sterile water | 1920 ml |
| HPMC-AS | 10 gram |
| Ethyl-cellulose N20 | 35 gram |
| Talc | 50 gram |
| Sodium alginate | 5 gram |

To test the stability of microsphere formulation, the size and surface structure of microspheres and an in vitro protein-release study were analyzed after the formulations were stored at various temperatures for at least 3 months. The dissolution test of the enteric-coated microspheres was conducted according to the pH-changing method of USP-XXII A (United States Pharmacopoeia, 1990). Microspheres with a total weight of 3 g were placed in a jacketed beaker containing 500 mL of 0.02 N HCl solution (pH 1.5) at 37° C. and rotated at 100 rpm. 5 mL of 0.2 M tri-sodium phosphate buffer were added to adjust the pH to 7 for further dissolution experiments, and each test was performed in triplicate. During dissolution testing, 1.5 mL of the samples were taken out at 30-min intervals, which were replaced by 1.5 mL of buffer solution to maintain the volume in the dissolution vessel. Samples were centrifuged at 15,000 g for 5 min, and the supernatants were aspirated and stored at −20° C.

Finally, the quantity of protein released was determined by using a Coomassie protein assay.

11. Experiment: Oral Administration of M-Cell Ligand Chimeric Polypeptides Enhancing the Mice Antibody Titers Against Specific Antigens 11-1. To Demonstrate that Immune Enhancement Effect of the Fusion Biogenic Polypeptides, Vaccination Program in Mouse Tests Through Orally Administration of Recombinant Antigens Male ICR mice were obtained at age 4 weeks, quarantined for 1 week before the study, and maintained throughout the study on libitum with pelleted food and water. Growth curve analysis were marked at 4th weeks and weighed twice a week up to 10 weeks. Males and females were separated at 4 weeks and littermates of the same sex placed in the same cage in order to keep the same environment for the different treatment during the rest of the experiment. The animals were assigned randomly to groups, which received combinations of oral dosing fusion antigen with bio-peptide enhancers as shown in Table 20. For each treatment, at least four mice were analyzed. Weights were plotted on growth curves and Anova statistical analysis using Stat View software was performed.

Used for oral immunization of PE-based vaccines and/or mucosal targeting bio-peptide enhancers were 2 different dosing schedules (3 mg low dose and 6 mg high dose of recombinant antigen formulation, i.e., equal to 10 mcg and 20 mcg protein concentrations). Mice were orally administered with one dose/one time/per week and 4 times with this microsphere solution using a blunt-tipped feeding needle inserted into their stomachs. The positive control group was immunized by subcutaneous injection with 0.25 mL PE-based vaccine that included 20 mcg (H dose) protein antigens at 2-week intervals for a total of four times immunizations.

Two weeks after each immunization, three mice were exsanguinated and blood was collected by puncturing their retroorbital plexuses. From the results in serum and intestinal specific antibodies titers against the fusion antigen was examined. Serum was obtained by coagulation at 4° C. for 12 h followed by centrifugation. Intestine lavage samples done at necropsy were collected by instilling 1 mL of washing buffer (PBS containing 100 g/mL soybean trypsin inhibitor, 50 mM EDTA, 1 mM PMSF, 0.5% gelatin, and 0.05% $NaN_3$) into the intestine. The lavage was collected and stored at −20° C., and lung samples after necropsy were gathered by homogenizing one-half of the lung with 0.5 mL of washing buffer. Finally, the supernatant of a lung-homogenized sample was collected and stored at −20° C. following centrifugation. Blood samples were taken and the serum assayed in an ELISA for the titer of anti-E7 or anti-E6 or anti-M14 or anti-GP3 or anti-GP4 specific antibodies using serial ten-fold dilutions. The specific IgA or IgG or IgG1 or IgG2a antibody titer was detected after the second round of immunization. The PRRS virus neutralization assay was examined with PE-GP417, 437 &317 by oral and injection vaccine groups.

The very high dose (VH) (100 mcg protein) and high-dose injections (H) (20 mcg protein) induced similar titers after the third round immunization and reached a plateau after the fourth round. The low dose of injection induced a lower titer, but was still detectable at a 1:3250 dilution after the fourth round immunization.

11-2. Experimental Tables

TABLE 20

The vaccination program and examination of immune enhancement effect of the fusion biogenic polypeptides in mouse tests Table 20-1 Experiment No. 1

| Vaccine groups one dose/1 time/per week and 4 times orally | | Immune enhancer L dose/1 time/per weelk and 4 times orally | |
|---|---|---|---|
| 1. Blank | 0 dose | — | 0 dose |
| 2. PE-E6 | L dose | PE-E622 | L dose |
| 3. PE-E6 | L dose | DQ2-PE-E622 | L dose |
| 4. PE-E601 | L dose | — | 0 dose |
| 5. PE-E6 | L dose | — | 0 dose |
| 6. Positive control through subcutaneous injection PE-E6* or PE-E106 (4 times injection with H dose) PE-E6 or PE-E106 monovalent vaccine H dose (20 meg total protein/dose) | | | |

*: PE-E6 vaccine published in Cheng WF et al., PLoS One. 2013 Sep 13; 8(9): e71216.

Table 20-2 Experiment No. 2

| Vaccine groups one dose/1 time/per week and 4 times orally | | Immune enhancer L dose/1 time/per week and 4 times orally | |
|---|---|---|---|
| 7. Blank | 0 dose | — | 0 dose |
| 8. PE-E601 | 2 L-doses | — | 0 dose |
| 9. PE-E601 | L dose | L2-200-PE-E622 | L dose |
| 10. PE-E601 | L dose | CO1-PE-E622 | L dose |
| 11. PE-E601 | L dose | DQ2-PE-E622 | L dose |
| 12. PE-E601 | L dose | RV3-PE-E6222 | L dose |

TABLE 20-continued

The vaccination program and examination of immune enhancement effect of the fusion biogenic polypeptides in mouse tests Table 20-3 Experiment No. 3

| Vaccine groups one dose/1 time/per week and 4 times orally | | Immune enhancer L dose/1 time/per week and 4 times orally | |
|---|---|---|---|
| 13. Blank | 0 dose | — | 0 dose |
| 14. PE-E601 | 2 L-doses | — | — |
| 15. PE-E601 | L dose | CO1-PE-E601 | L dose |
| 16. PE-E601 | L dose | DQ2-PE-E601 | L dose |
| 17. PE-E601 | L dose | RV3-PE-E601 | L dose |
| 18. PE-E601 | L dose | L2-200-PE-E601 | — |

Table 20-4 Experiment No. 4

| Vaccine groups one dose/1 time/per week and 4 times orally | | Immune enhancer L dose/1 time/per week and 4 times orally | |
|---|---|---|---|
| 19. Blank | — | — | — |
| 20. PE-E7 | L dose | PE425-E713 | L dose |
| 21. PE-E7 | L dose | DQ2-PE425-E713 | L dose |
| 22. PE-E701 | L dose | — | — |
| 23. PE-E7 | L dose | — | — |
| 24. Positive connol through subcutaneous injection PE-E701 (4 times injection with H dose) PE-E7 monovalent vaccine H dose (20 mcg total protein/dose | | | |

Table 20-5 Experiment No. 5

| Vaccine groups one dose/1 time/per week and 4 times orally | | Immune enhancer L dose/1 time/per week and 4 times orally | |
|---|---|---|---|
| 25. Blank | — | — | 0 dose |
| 26. PE-E701 | L dose | PE-E713 | L dose |
| 27. PE-E701 | L dose | L2-200-PE-E713 | L dose |
| 28. PE-E701 | L dose | CO1-PE-E713 | L dose |
| 29. PE-E701 | L dose | DQ2-PE-E713 | L dose |
| 30. PE-E701 | L dose | RV3-PE-E713 | L dose |

Table 20-6 Experiment No. 6

| Vaccine groups one dose/1 time/per week and 4 times orally | | Immune enhancer L dose/1 time/per week and 4 times orally | |
|---|---|---|---|
| 31. PE-M14 | 2 L-doses | — | — |
| 32. PE-M14 | L dose | CO1-PE-M14 | L dose |
| 33. PE-M14 | L dose | DQ2-PE-M14 | L dose |
| 34. PE-M14 | L dose | RV3-PE-M14 | L dose |
| 35. PE-M14 | L dose | PE-M27 | L dose |
| 36. PE-M14 | L dose | CO1-PEM27 | L dose |
| 37. PE-M14 | L dose | DQ2-PE-M27 | L dose |
| 38. PE-M14 | L dose | RV3-PE-M27 | L dose |
| 39. Blank | L dose | — | 0 dose |

Table 20-7 Experiment No. 7

| Vaccine groups one dose/1 time/per week and 4 times orally | | Immune enhancer L dose/1 time/per week and 4 times orally | |
|---|---|---|---|
| 40. Blank | — | — | — |
| 41. PE-GP417 | L dose | CO1 PE-GP417 | L dose |
| 42. PE-GP417 | L dose | DQ2-PE-GP417 | L dose |
| 43. PE-GP417 | L dose | RV3-PE-GP417 | L dose |
| 44. PE-GP417 | 2 L-doses | — | — |
| 45. PE-GP437 | L dose | CO1-PE-GP437 | L dose |
| 46. PE-GP437 | L dose | DQ2-PE-GP437 | L dose |
| 47. PE-GP437 | L dose | RV3-PE-GP437 | L dose |

TABLE 20-continued

| The vaccination program and examination of immune enhancement effect of the fusion biogenic polypeptides in mouse tests | | | |
|---|---|---|---|
| 48. PE-GP437 | 2 L-doses | — | — |
| 49. Positive control through subcutaneous injection PE-GP417&437 (4 times injection with H dose) PE-GP417&437 bivalent vaccine H dose (20 mcg total protein/dose) | | | |

Table 20-8 Experiment No. 8

| Vaccine groups one dose/1 time/per week and 4 times orally | | Immune enhancer L dose/1 time/per week and 4 times orally | |
|---|---|---|---|
| 50. Blank | — | — | — |
| 51. PE-GP317 | L dose | CO1-PE-GP317 | L dose |
| 52. PE-GP317 | L dose | DQ2-PE-GP317 | L dose |
| 53. PE-GP317 | L dose | RV3-PE-GP317 | L dose |
| 54. PE-GP317 | 2 L-doses | — | — |

11-3. Oral Immunization Experiment in Pig Model: Oral Administration of M-Cell Ligand Chimeric Polypeptides Enhancing the Swine Antibodies Titer Against Specific Antigens In the pig model, each 24 piglets were selected respectively from six sows source in a healthy pig farming. Three piglets from each sow were assigned and marked with ear-number randomly to the vaccinated and control groups as listed in Table 21. The oral vaccine group totally contained nine piglets, which received orally L dose (3 mg) or H dose (6 mg) suspended in a 2% acetate solution at the ages 4, 6, 7, 9, 12, 14, 16, 18, 21, 24, 26 and 28-day. The intramuscular administration group contained another three piglets that received a VH dose (100 mcg for each antigen) of PE-GPs trivalent with two times injection. These were immunized at ages 14 and 28-day by intramuscular injection with 1 mL of vaccine that included 0.5 mL of formalin-inactive broth (300 mcg total protein of GP417, 437, and 317 antigens) and 0.5 mL aluminum gel. These last 3 piglets served as controls. After accomplishment of the oral and injection administration program, all the experiment piglets, age 29-30-day, were moved and kept in groups of ten in straw-bedded pens 3.8 m×4.5 m (17 $m^2$). Air temperature and humidity were recorded twice a day throughout the testing period. Animals were fed the same complete feed mixture.

TABLE 21

| The vaccination program and examination of immune enhancement effect of the mucosal targeting polypeptides in piglet tests | | | |
|---|---|---|---|
| Vaccine groups (N = 3) L dose/3 time/per week and 12 times orally/4 weeks | | Immune enhancer (N = 3) L dose/3 time/per week and 12 times orally/4 weeks | |
| Blank | 0 dose | — | 0 dose |
| PE-M14 | L dose | DQ2-PE-M14 | L dose |
| PE-M14 | L dose | DQ2-PE-M27 | L dose |
| PE-M14 | H dose | — | — |
| PE-GP417, 437, 317 | L dose | DQ2-PE-GP417 | L dose |
| PE-GP417, 437, 317 | L dose, additional with PE-GP417 | | L dose |
| PE-GP417, 437, 317 | H dose | — | — |
| Positive control through intramuscular injection (N = 3) twice at ages 14 and 28-day | | | |
| PE-GP417, 437, 317 trivalent vaccine | | VH dose (300 mcg total protein/dose) | |

The observation and monitored for grow performance and health was preceded by a 2-day period during which the piglets were adapted to the new environment. The data was subjected to analysis of variance (ANOVA) to obtain the effect of post-weaning age on weight gain and linear measurements.

Two weeks after finishing immunization program, piglet blood was collected by puncturing their retroorbital plexuses. From the results in serum and intestinal specific antibodies titers against the fusion antigen was examined. Serum was obtained by coagulation at 4° C. for 12 h followed by centrifugation. Blood samples were taken and the serum assayed in an ELISA for the titer of anti-Myo14 or anti-GP317 or anti-GP417&437 specific antibodies using serial 2.5-fold dilutions. The specific IgA or IgG or IgG1 or IgG2a antibody titer was detected after the second round of immunization. The PRRS virus neutralization assay was examined PE-GP417, 437 &317 oral and injection vaccine groups.

11-4. Measurement of Antibody Responses by ELISA

Polystyrene microdilution plates (Costar) were coated with antigens. The plates were coated with 100 µl per well with this antigen at a concentration of 2 µg/mL protein in coating buffer (carbonate-bicarbonate buffer at pH 9.6). Binding antibody titers induced the six proteins (E7, E6, Myo14, Myo27, GP3, GP4) were analyzed using ELISA tests. Following overnight adsorption each protein antigens at 4° C., in-directed ELISA was performed as described (Liao 2003). Horse radish peroxidase (HRP)-conjugated secondary antibodies (goat anti-Mouse IgG, IgA, IgG2, IgG1) were diluted at the optimal concentration (×1000 fold) in blocking buffer immediately before use. Note that a positive reference sample with a high antibody titer should be used to determine the titers of antibodies. This reference sample was made into aliquots and preserved in the lyophilized state. The serum sample was diluted 500×, 2500×, 12500×, and 62500×, respectively. The intestinal and lung samples were diluted 10-fold times for routine work. To interpret the results accurately, ELISA (E) value was determined by the following formula: E value=D× (S−N)/(P−N), where the OD value of injection vaccine sample=positive control serum or lavage, N=negative control serum or lavage, S=test sample, and D=sample dilution fold.

11-5. PRRSV Serum Neutralization Test by Indirect Immunofluorescence

PRRS virus neutralization test by indirect immunofluorescence assay. All filtered oral fluid and serum samples (0.2-µm filter) used in the NA assay were treated with UV light (254 nm) at a distance of two inches from the samples in plates for 45 min and were then heat inactivated for 30 min at 56° C. Each test sample was 2-fold serially diluted (1:2 to 1:128) in serum-free DMEM (100 µl per well) and incubated with an equal volume of 100 TCID50 of one of the PRRSV strains (PRRSV TC-01) for 1 h at 37° C. After incubation, 100 µl of the supernatant was transferred into a 96-well microtiter plate containing a confluent monolayer of Alveolar macrophage 3D4/31 (ATCC CRL-2844; Alveolar macrophage; immortalized with SV40 large T antigen); each sample was run in duplicate. After 1 h of incubation, 100 µl of DMEM containing 2% horse serum and an antibiotic-antimycotic mixture was added, and the plate was incubated for 48 h at 37° C. in a $CO_2$ incubator. Cells were fixed using an acetone/Milli-Q water (8:2) mixture for 10 min at room temperature (~20° C.), and plates were dried completely before being immunostained as described previously. Cells were treated with anti-PRRSV nucleocapsid protein-specific monoclonal antibody (SDOW17) (Rural Technologies, Inc., SD) (1:5,000) for 2 h at 37° C., followed by treatment with Alexa Fluor 488 conjugated goat anti-mouse IgG(H+L) (Invitrogen, CA) secondary antibody (1:3,000). The plate was examined under a fluorescence microscope after mounting with glycerol-phosphate-buffered saline (PBS) (6:4). The virus-neutralizing antibody (NA) titer was determined to be the reciprocal dilution ratio of the sample at which >90% inhibition in the PRRSV-induced immunofluorescence was observed.

12. Result of Experiments

12-1. The Efficacy of Fusion Polypeptides as Immune Enhancers on the PE-Based E6 Oral Vaccine The high-risk human papillomavirus E6 (hrHPV E6) protein has been widely studied due to its implication in the process of malignant transformation of human cells. HPV 16 E6 oncoprotein could affect the IL-18 induced IFN-γ production in human PBMCs to elucidate the possible immune escape mechanisms of HPV infected cervical lesion including cervical cancer. The E6 oncoprotein of HPV-16 and HPV-18 inhibit immune response by interacting with host IRF3 and TYK2 (Li S et al., *Oncogene.* 1999 Oct. 14; 18(42):5727-37; Masaud Shah et al., *Scientific Reports* 5, Article number: 13446 (2015); Cheng W F et al., *PLoS One.* 2013 Sep. 13; 8(9):e71216; Cho Y S et al., *FEBS Lett.* 2001 Jul. 20; 501(2-3):139-45). In our previous research, the E6-specific immune responses generated by the PE-E6 vaccine were weaker than the E7-specific immune responses of the PE-E7 through injection mice model. In this disclosure, we evaluated the efficacy of PE-E6 oral vaccine on immune response through oral administration in mice model. In the experiments, we demonstrated that the mucosal targeting epitopes, including DQ2 and RV3 had something enhancement activity of E6-specific immune response from fallowing data analysis.

In Table 22, oral administrations of PE-E6 or PE-E601 demonstrated weak immune response against E6 or E601 antigen according to the mice serum antibodies activity data of the group no. 4 and 5 by ELISA test. However, the serum IgA and IgG antibodies activity of PE-E6 vaccine with additional PE-E622 or DQ2-PE-E622 immune enhancer, group no. 2 and 3, could be enhanced. From the E6-specific IgG activity in serum dilution 500-fold samples, the data of the group No. 3 was significantly higher than other oral vaccine groups without enhancer additional (p<0.05).

TABLE 22

Serum levels of IgG and IgA against HPV-16 E6 in the mice groups by ELISA test

| Group no. (n = 3) | Vaccine | Enhancer | dilx 200 Average | dilx 200 Stdev | dilx 500 Average | dilx 500 Stdev | dilx 1250 Average | dilx 1250 Stdev |
|---|---|---|---|---|---|---|---|---|
| | Serum anti-E6 IgG activity in ELISA-Test | | | | | | | |
| 1 | Blank | — | 0.35 | 0.10 | 0.27 | 0.03 | 0.22 | 0.02 |
| 2 | PE-E6 | PE-E622 | 0.70 | 0.11 | 0.45 | 0.06 | 0.19 | 0.06 |

TABLE 22-continued

Serum levels of IgG and IgA against HPV-16 E6 in the mice groups by ELISA test

| Group no. (n = 3) | Vaccine | Enhancer | dilx 200 Average | dilx 200 Stdev | dilx 500 Average | dilx 500 Stdev | dilx 1250 Average | dilx 1250 Stdev |
|---|---|---|---|---|---|---|---|---|
| 3 | PE-E6 | DQ2-PE-E622 | 0.77 | 0.08 | 0.59 | 0.08 | 0.25 | 0.08 |
| 4 | PE-E601 | — | 0.39 | 0.05 | 0.22 | 0.05 | 0.18 | 0.05 |
| 5 | PE-E6 | — | 0.55 | 0.14 | 0.34 | 0.10 | 0.22 | 0.10 |
| 6 | Inject (H dose) | — | 0.90 | 0.05 | 0.71 | 0.07 | 0.35 | 0.07 |
| | Serum anti-E6 IgA activity in ELISA-Test | | | | | | | |
| 1 | Blank | — | 0.15 | 0.08 | 0.18 | 0.03 | 0.18 | 0.03 |
| 2 | PE-E6 | PE-E622 | 0.40 | 0.14 | 0.30 | 0.11 | 0.25 | 0.06 |
| 3 | PE-E6 | DQ2-PE-E622 | 0.43 | 0.10 | 0.33 | 0.08 | 0.24 | 0.08 |
| 4 | PE-E601 | — | 0.27 | 0.05 | 0.20 | 0.05 | 0.18 | 0.05 |
| 5 | PE-E6 | — | 0.38 | 0.14 | 0.26 | 0.10 | 0.19 | 0.10 |
| 6 | Inject (H dose) | — | 0.45 | 0.05 | 0.37 | 0.07 | 0.22 | 0.07 |

In the table 23, E6 or E601-specific serum IgG1 and IgG2a responses were assayed by ELISA, 2-3 weeks after oral administration of vaccine and/or additional immune enhancers. From the data of the group No. 3, oral administration of PE-E6 vaccine with additional DQ2-PE-E622 immune enhancer could elicit a good Th1 pathway according to the high ratio of IgG2a/IgG1. The IgG2a/IgG1 ratio was 1.4-1.5 in the group no. 3 (PE-E6 oral vaccine with additional DQ2-PE-E622 enhancer). It was significantly higher than other groups without enhancer additional (p<0.05). The IgG2a/IgG1 ratio of the E6-specific antibodies in group no. 2 (PE-E6 oral vaccine with additional PE-E622 enhancer) was 1.13, that was not strong significantly compared with other groups which without enhancer additional (p>0.05).

TABLE 23

Serum activity of IgGs anti-E6 or anti-E601 and its IgG2a/IgG1 ratio

| Group no. (n = 3) | Vaccine | Enhancer | IgG1 Average | IgG1 Stdev | IgG2 Average | IgG2 Stdev | IgG2a/IgG1 |
|---|---|---|---|---|---|---|---|
| | Anti-E6 activity in ELISA-Test | | | | | | |
| 1 | Blank | — | 0.17 | 0.10 | 0.09 | 0.03 | |
| 2 | PE-E6 | PE-E622 | 0.36 | 0.11 | 0.45 | 0.06 | 1.24 |
| 3 | PE-E6 | DQ2-PE-E622 | 0.42 | 0.08 | 0.59 | 0.08 | 1.41 |
| 4 | PE-E601 | — | 0.19 | 0.05 | 0.18 | 0.05 | 0.96 |
| 5 | PE-E6 | — | 0.38 | 0.14 | 0.24 | 0.10 | 0.63 |
| 6 | Inject (H dose) | — | 0.48 | 0.05 | 0.42 | 0.07 | 0.08 |
| | Anti-E601 activity in ELISA-Test | | | | | | |
| 1 | Blank | — | 0.15 | 0.08 | 0.18 | 0.03 | |
| 2 | PE-E6 | PE-E622 | 0.40 | 0.14 | 0.45 | 0.11 | 1.13 |
| 3 | PE-E6 | DQ2-PE-E622 | 0.43 | 0.10 | 0.65 | 0.08 | 1.51 |
| 4 | PE-E601 | — | 0.29 | 0.05 | 0.27 | 0.05 | 0.94 |

TABLE 23-continued

Serum activity of IgGs anti-E6 or anti-E601 and its IgG2a/IgG1 ratio

| Group no. (n = 3) | Vaccine | Enhancer | IgG1 Average | IgG1 Stdev | IgG2 Average | IgG2 Stdev | IgG2a/IgG1 |
|---|---|---|---|---|---|---|---|
| 5 | PE-E6 | — | 0.32 | 0.14 | 0.24 | 0.10 | 0.75 |
| 6 | Inject (H dose) | — | 0.33 | 0.05 | 0.22 | 0.07 | 0.67 |

In Table 24, five groups of mice were oral administration of PE-E601 vaccine additional with various enhancers including PE-E601, L2-L200-PE-E622, CO1-PE-E622, DQ2-PE-E622 and RV3-PE-E622, respectively.

The immune responses of those groups of mice against E601 antigen were examined according to mice serum IgG1, IgG2a antibodies activity by ELISA test. Through the IgG2a/IgG1 ratio data, the Th1 or Th2 immune pathway could be prospected. The IgG2a/IgG1 ratio was 1.56 or 1.46 in the group no. 11 or 12 (PE-E601 oral vaccine with additional DQ2-PE-E622 or RV3-PE-E622 enhancer), but those of the group 8 or 9 or 10 (PE-E601 oral vaccine additional with PE-E601 or L2-200-PE-E622 or CO1-PE-E622 enhancer) was lower than 1.05. According to the high ratio of E601-specific IgGs and IgG2a/IgG1 data in mice experiments, the DQ2-PE-E622 and RV3-PE-E622 enhancers could strongly elicit a good Th1 immunity when PE-based E601 oral vaccine administration with additional the enhancers. The Th1 immunity enhancing efficacy of DQ2-PE-E622 and RV3-PE-E622 were significantly different from other groups ($P<0.05$).

TABLE 24

| Group no. (n = 3) | Anti-E601 activity in ELISA-Test Vaccine | Enhancer | IgG1 Average | IgG1 Stdev | IgG2 Average | IgG2 Stdev | IgG2a/IgG1 |
|---|---|---|---|---|---|---|---|
| 7 | Blank | — | 0.15 | 0.08 | 0.18 | 0.03 | |
| 8 | PE-E601 | 2 L-doses | 0.33 | 0.04 | 0.28 | 0.07 | 0.83 |
| 9 | PE-E601 | L2-200-PE-E622 | 0.40 | 0.03 | 0.38 | 0.03 | 0.94 |
| 10 | PE-E601 | CO1-PE-E622 | 0.42 | 0.03 | 0.44 | 0.03 | 1.04 |
| 11 | PE-E601 | DQ2-PE-E622 | 0.29 | 0.04 | 0.45 | 0.05 | 1.56 |
| 12 | PE-E601 | RV3-PE-E6222 | 0.31 | 0.03 | 0.45 | 0.04 | 1.46 |

In Table 25, five groups of mice are oral administration of PE-E601 vaccine additional with various enhancers including PE-E601, L2-200-PE-E601, CO1-PE-E601, DQ2-PE-E601 and RV3-PE-E601, respectively.

The immune response of those groups of mice against E601 antigen examined according to mice serum IgG1, IgG2a antibodies activity by ELISA test. Through the IgG2a/IgG1 ratio data, the Th1 or Th2 pathway could be prospected. The IgG2a/IgG1 ratio is 1.24 or 1.28 in the group no. 16 or 17 (PE-E601 oral vaccine additional with DQ2-PE-E622 or RV3-PE-E622 enhancer), but those of the group 14 or 15 or 18 (PE-E601 oral vaccine additional with PE-E601 or CO1-PE-E622 or L2-200-PE-E622) was lower than 1.05. According to the high ratio of IgG2a/IgG1 data in mice experiments, the DQ2-PE-E622 and RV3-PE-E622 enhancers can elicit a good Th1 pathway when PE-based E016 oral vaccine administration additional with the enhancers ($p<0.05$).

TABLE 25

| Group no. (n = 3) | Anti-E601 activity in ELISA-Test Vaccine | Enhancer | IgG1 Average | IgG1 Stdev | IgG2 Average | IgG2 Stdev | IgG2a/IgG1 |
|---|---|---|---|---|---|---|---|
| 13 | Blank | — | 0.15 | 0.08 | 0.18 | 0.03 | |
| 14 | PE-E601 | 2 L-doses | 0.33 | 0.05 | 0.28 | 0.07 | 0.83 |
| 15 | PE-E601 | CO1-PE-E601 | 0.34 | 0.05 | 0.34 | 0.03 | 1.00 |
| 16 | PE-E601 | DQ2-PE-E601 | 0.35 | 0.05 | 0.44 | 0.03 | 1.24 |
| 17 | PE-E601 | RV3-PE-E601 | 0.35 | 0.04 | 0.45 | 0.05 | 1.28 |
| 18 | PE-E601 | L2-200-PE-E601 | 0.33 | 0.05 | 0.31 | 0.04 | 0.94 |

12-2. The Effect of Fusion Biogenic Polypeptides Enhancers on the PE-Based E7 Oral Vaccine Our previous studies indicated that a based E7 fusion protein vaccine enhanced MHC class I and II presentation of E7, leading to dramatic increases in the number of E7-specific CD8+ and CD4+ T-cell precursors and markedly raised titers of E7-specific antibodies. These results indicated that retrograde-fusion protein via the delivery domains of exotoxins with an antigen greatly enhances in vivo antigen-specific immunologic responses and represents a novel strategy to improve cancer injection vaccine potency (Ebrahimpoor S et al., *Iran J Allergy Asthma Immunol.* 2013 Aug. 28; 12(4):361-7.). In the present disclosure, we try to evaluate the efficacy of PE-E7 oral vaccine on immune response of mice test through oral administration. We performed a study on the oral administration experiments of PE-E7 in mice immunization test that we got similar results that were found in PE-E6 study. Orally administrations of PE-E7 or PE-E701 demonstrated weak immune response against E7 or E701 antigen. In the present disclosure, we demonstrated that the mucosal targeting epitopes, including DQ2 and RV3 had something enhancement activity of E6-specific antibodies from fallowing data analysis.

In Table 26, oral administrations of PE-E7 or PE-E701 demonstrated weak immune response against E7 or E701 antigen according to the mice serum antibodies activity data of the group no. 22 and 23 by ELISA test.

TABLE 26

| Group no. (n = 3) | Vaccine | Enhancer | dilx 200 Average | dilx 200 Stdev | dilx 500 Average | dilx 500 Stdev | dilx 1250 Average | dilx 1250 Stdev |
|---|---|---|---|---|---|---|---|---|
| | Serum anti-E7 IgG activity in ELISA-Test | | | | | | | |
| 19 | Blank | — | 0.30 | 0.10 | 0.24 | 0.03 | 0.18 | 0.04 |
| 20 | PE-E7 | PE-E713 | 0.72 | 0.15 | 0.43 | 0.10 | 0.30 | 0.07 |
| 21 | PE-E7 | DQ2-PE-E713 | 0.93 | 0.05 | 0.55 | 0.06 | 0.39 | 0.05 |
| 22 | PE-E701 | — | 0.44 | 0.07 | 0.22 | 0.06 | 0.19 | 0.05 |
| 23 | PE-E7 | — | 0.68 | 0.14 | 0.34 | 0.10 | 0.22 | 0.10 |
| 24 | Inject (H dose) | — | 1.50 | 0.15 | 0.75 | 0.07 | 0.48 | 0.07 |

TABLE 26-continued

| Group no. (n = 3) | Vaccine | Enhancer | dlix 200 Average | dlix 200 Stdev | dilx 500 Average | dilx 500 Stdev | dilx 1250 Average | dilx 1250 Stdev |
|---|---|---|---|---|---|---|---|---|
| | Serum anti-E7 IgA activity in ELISA-Test | | | | | | | |
| 19 | Blank | — | 0.21 | 0.08 | 0.18 | 0.03 | 0.18 | 0.03 |
| 20 | PE-E7 | PE-E713 | 0.50 | 0.16 | 0.30 | 0.10 | 0.25 | 0.06 |
| 21 | PE-E7 | DQ2-PE-E713 | 0.60 | 0.12 | 0.33 | 0.05 | 0.24 | 0.08 |
| 22 | PE-E701 | — | 0.21 | 0.15 | 0.20 | 0.07 | 0.18 | 0.05 |
| 23 | PE-E7 | — | 0.43 | 0.20 | 0.26 | 0.07 | 0.19 | 0.10 |
| 24 | Inject (H dose) | — | 0.60 | 0.15 | 0.37 | 0.07 | 0.22 | 0.07 |

However, the serum IgA and IgG antibodies activity of PE-E7 vaccine group with additional PE-E622 or DQ2-PE-E622, group no. 20 and 21, could be enhanced. From the E7-specific IgG activity in serum dilution 200-fold samples, the data of the group No. 21 was significantly higher than other oral vaccine groups without enhancer additional ($p<0.05$).

In Table 27, five groups of mice were oral administration of PE-E701 vaccine additional with various enhancers including PE-E713, L2-L200-PE-E713, CO1-PE-E713, DQ2-PE-E713 and RV3-PE-E713, respectively.

TABLE 27

| Group no. (n = 3) | Serum anti-E701 IgGs activity in ELISA-Test: Vaccine | Enhancer | IgG1 Average | IgG1 Stdev | IgG2 Average | IgG2 Stdev | IgG2a/IgG1 |
|---|---|---|---|---|---|---|---|
| 25 | Blank | — | 0.18 | 0.09 | 0.19 | 0.05 | |
| 26 | PE-E701 | PE-E713 | 0.36 | 0.06 | 0.37 | 0.10 | 1.03 |
| 27 | PE-E701 | L2-200-PE-E713 | 0.42 | 0.06 | 0.65 | 0.05 | 1.55 |
| 28 | PE-E701 | CO1-PE-E713 | 0.47 | 0.06 | 0.63 | 0.07 | 1.34 |
| 29 | PE-E701 | DQ2-PE-E713 | 0.47 | 0.08 | 0.67 | 0.09 | 1.43 |
| 30 | PE-E701 | RV3-PE-E713 | 0.48 | 0.06 | 0.69 | 0.05 | 1.44 |

The immune responses of those groups of mice against E701 antigen were examined according to mice serum IgG1, IgG2a antibodies activity by ELISA test. Through the IgG2a/IgG1 ratios data, the Th1 or Th2 immune pathway could be prospected. The IgG2a/IgG1 ratios were 1.55, 1.34, 1.43 and 1.44 in the group no. 27, no. 28, no. 29 and no. 30 which were PE-E701 oral vaccine with additional L2-200-PE-713, CO1-PE-E713, DQ2-PE-E713, RV3-PE-E713 enhancers, respectively. The IgG2a/IgG1 ratios of group 26 (PE-E701 oral vaccine additional with PE-E713 enhancer) was lower than 1.05. According to the high activity of E701-specific IgG2a and high IgG2a/IgG1 ratios data, the L2-200-PE-713, CO1-PE-E713, DQ2-PE-E622 and RV3-PE-E622 enhancers could strongly elicit a good Th1 immunity when PE-based E713 oral vaccine administration with additional these enhancers in mice immunization model. The immunity enhancing efficacy of E701-specific IgG2a showed that L2-200-PE-713, CO1-PE-E713, DQ2-PE-E713 and RV3-PE-E713 groups had significantly different from PE-E713 enhancer groups ($P<0.05$).

12-3. The Efficacy of Fusion Polypeptides as Immune Enhancers on the PE-Based Myostatin Oral Vaccine Recombinant myostatin can induce immune responses to myostatin by oral route, resulting in increasing body weight in mice. It is an important step towards transforming cells into edible vaccine to improve meat production in farm animals and combat muscle-waste genetic diseases in human (Zhang T et al., *BMC Biotechnol.* 2012 Dec. 19; 12:97; Aravind S et al., *J Virol Methods.* 2012 November; 185(2): 234-8).

We have established a PE-based myostatin fused oral vaccine for animal use. There were several fusion biogenic polypeptide enhancers were developed for PE-based myostatin fused oral vaccine formulation. In the present disclosure, we demonstrated that the mucosal targeting epitopes, including CO1, DQ2 and RV3 had something enhancement activity of myostatin epitope-specific antibodies from fallowing data analysis.

In Tables 28 and 29, the M14-specific serum IgG and IgA activities of ELISA in serial serum dilutions (1:200-1:1250) were examined in various serum samples.

TABLE 28

| Group no. (n = 3) | Serum anti-M14 IgG activity in ELISA-Test: Vaccine | Enhancer | dilx 200 Average | dilx 200 Stdev | dilx 500 Average | dilx 500 Stdev | dilx 1250 Average | dilx 1250 Stdev |
|---|---|---|---|---|---|---|---|---|
| 31 | PE-M14 | 2 L-doses | 0.56 | 0.20 | 0.51 | 0.07 | 0.34 | 0.04 |
| 32 | PE-M14 | CO1-PE-M14 | 0.80 | 0.23 | 0.78 | 0.16 | 0.41 | 0.04 |
| 33 | PE-M14 | DQ2-PE-M14 | 0.81 | 0.16 | 0.66 | 0.06 | 0.44 | 0.04 |
| 34 | PE-M14 | RV3-PE-M14 | 0.95 | 0.24 | 0.74 | 0.17 | 0.36 | 0.06 |
| 39 | Blank | — | 0.30 | 0.10 | 0.27 | 0.03 | 0.22 | 0.02 |

TABLE 29

| Group no. (n = 3) | Serum anti-M14 IgA activity in ELISA-Test: Vaccine | Enhancer | dilx 200 Average | dilx 200 Stdev | dilx 500 Average | dilx 500 Stdev | dilx 1250 Average | dilx 1250 Stdev |
|---|---|---|---|---|---|---|---|---|
| 35 | PE-M14 | PE-M27 | 0.58 | 0.24 | 0.45 | 0.01 | 0.29 | 0.09 |
| 36 | PE-M14 | CO1-PE-M27 | 0.75 | 0.12 | 0.69 | 0.16 | 0.35 | 0.05 |
| 37 | PE-M14 | DQ2-PE-M27 | 0.75 | 0.06 | 0.64 | 0.07 | 0.33 | 0.03 |
| 38 | PE-M14 | RV3-PE-M27 | 0.79 | 0.13 | 0.66 | 0.16 | 0.29 | 0.05 |
| 39 | Blank | — | 0.27 | 0.02 | 0.25 | 0.03 | 0.23 | 0.03 |

According to serial dilutions ELISA data of the group no. 31 (PE-M14 vaccine group), it demonstrated that oral administration of PE-M14 vaccine elicited a good M14-specific IgG and IgA serum titers in the 1:200 to 1:1250 fold serum dilutions. Furthermore, the serum IgA and IgG antibodies activities of the groups of PE-M14 vaccine with additional CO1-PE-M14, DQ2-PE-M14 and RV3-PE-M14, CO1-PE-M27, DQ2-PE-M27 and RV3-PE-M27, corresponded to the group no. 32, 33 34, 36, 37 and 38 could be extremely enhanced. From the M14-specific IgG activity in serum dilution 500-fold samples, the data of the group No.

32, No. 33 and No. 34 were significantly higher than other oral vaccine groups (p<0.05).

In Table 30, the data demonstrated that PE-based M14 fused oral vaccines could be enhanced by the mucosal targeting ligands, CO1, DQ2 and RV3. The serum specific-M14 antibodies activities (with serum 500 dilutions-ELISA) of IgG and IgA of the groups no. 32, 33 and 34, which treated with additional CO1-PE-M14, DQ2-PE-M14 and RV3-PE-M14 enhancer respectively, were slightly higher than that of activities of the group No. 31 (p>0.1). Furthermore, the activities of groups no. 36, 37, 38 presented very high level than that of groups no. 31 or no. 35, without Mucosal targeting ligands additional. Specifically, the IgG and IgA levels of group no. 37 and 38 were significantly higher (p<0.05) when compared with the control group (such as group no. 31 or 35).

TABLE 30

| Group no. | Serum anti-M14 IgA activity in ELIS A-Test | | Value of OD405 by ELISA (the level of IgG antibody) | | Value of OD405 by ELISA (the level of IgA antibody) | |
|---|---|---|---|---|---|---|
| (n = 3) | Vaccine | Enhancer | Average | Stdev | Average | Stdev |
| 31 | PE-M14 2 L-doses | | 0.48 | 0.07 | 0.40 | 0.05 |
| 32 | PE-M14 | CO1-PE-M14 | 0.62 | 0.10 | 0.53 | 0.10 |
| 33 | PE-M14 | DQ2-PE-M14 | 0.60 | 0.16 | 0.55 | 0.08 |
| 34 | PE-M14 | RV3-PE-M14 | 0.65 | 0.13 | 0.57 | 0.05 |
| 35 | PE-M14 | PE-M27 | 0.51 | 0.07 | 0.45 | 0.08 |
| 36 | PE-M14 | CO1-PE-M27 | 0.78 | 0.22 | 0.69 | 0.16 |
| 37 | PE-M14 | DQ2-PE-M27 | 0.68 | 0.05 | 0.64 | 0.07 |
| 38 | PE-M14 | RV3-PE-M27 | 0.75 | 0.10 | 0.66 | 0.06 |
| 39 | Blank | — | 0.30 | 0.10 | 0.27 | 0.1 |

12-4. The Efficacy of Fusion Polypeptides as Immune Enhancers on the PE-Based PRRS GP3-GP4 Epitopes Oral Vaccine Porcine reproductive and respiratory syndrome (PRRS) causes devastating economic losses due to late-term reproductive failure and severe pneumonia in neonatal pigs. PRRS disease is a high-consequence animal disease with current vaccines providing limited protection from infection due to the high degree of genetic variation of field PRRS virus. Serum neutralizing antibodies (NAs) considered being an important correlate of protective immunity against PRRSV. The role that NA have in protection against infection with PRRSV had been demonstrated by Lopez et al (2007). His results identified certain threshold of serum virus neutralization (SVN) titer (≥1:8) at which the dissemination of PRRSV in the serum of a young pig would be blocked, as well as a higher threshold (≥1:32) that could imply complete protection of the animal from PRRSV infection. We had been developed a PE-based PRRSV subunit vaccine. However, the subunit vaccine has to be improved about SVN titer eliciting against PRRS disease control. In the present disclosure, the fallowing experimental result could show that the efficacy of fusion polypeptides as oral immune enhancers could elicit SVN.

In Table 31, the data demonstrated that PE-based GPs fused oral vaccines could be enhanced by the mucosal targeting ligands, CO1, DQ2 and RV3.

According to serial dilutions ELISA data of the group no. 44 and 48 (PE-GP417 and PE-GP437 vaccine groups), it showed that oral administration of PE-GP417 and PE-GP437 elicited a good GP417 and GP437-specific IgG serum titers in the 1:200 to 1:1250 fold serum dilutions. The serum IgG antibodies activities of PE-GP417 or PE-GP437 vaccine with additional CO1-PE-GP417 or CO1-PE-GP437, DQ2-PE-GP417 or DQ2-PE-GP437 and RV3-PE-GP417 or RV3-PE-GP437 immune enhancers, corresponded to the group no. 41 or 45, 42 or 46 and 43 or 47, could increase the antibodies activity. From the GP417-specific IgG activity in serum dilution 500-fold samples, the data of the group No. 41, No. 42 and No. 43 were significantly higher than other oral vaccine groups (p<0.02). From the GP-437-specific IgG activity in that dilution fold samples of the group No. 46 and 47, it showed good immune enhancing effect, but No. 45 group was not. From the result, the mucosal targeting epitopes including CO1, DQ2 and RV3 had good enhancement activity in GP417 epitope-specific antibodies, and DQ2 and RV3 had good enhancement activity in the GP437 antibodies.

TABLE 31

| Group no. | Serum anti-GP417 & 437 IgG activity in ELISA-Test | | dilx 200 | | dilx 500 | | dilx 1250 | | dilx 3125 | |
|---|---|---|---|---|---|---|---|---|---|---|
| (n = 3) | Vaccine | Enhancer | Average | Stdev | Average | Stdev | Average | Stdev | Average | Stdev |
| 40 | Blank | — | 0.31 | 0.10 | 0.23 | 0.08 | 0.22 | 0.05 | 0.27 | 0.08 |
| 41 | PE-GP417 | CO1-PE-GP417 | 0.60 | 0.11 | 0.49 | 0.06 | 0.28 | 0.06 | 0.22 | 0.06 |
| 42 | PE-GP417 | DQ2-PE-GP417 | 0.77 | 0.08 | 0.59 | 0.08 | 0.39 | 0.08 | 0.22 | 0.03 |
| 43 | PE-GP417 | RV3-PE-GP417 | 0.69 | 0.11 | 0.52 | 0.05 | 0.38 | 0.05 | 0.25 | 0.05 |
| 44 | PE-GP417 2 L-doses | | 0.52 | 0.13 | 0.34 | 0.10 | 0.25 | 0.11 | 0.28 | 0.05 |
| 45 | PE-GP437 | CO1-PE-GP437 | 0.64 | 0.11 | 0.51 | 0.11 | 0.26 | 0.08 | 0.24 | 0.05 |
| 46 | PE-GP437 | DQ2-PE-GP437 | 0.85 | 0.12 | 0.63 | 0.08 | 0.44 | 0.09 | 0.32 | 0.03 |
| 47 | PE-GP437 | RV3-PE-GP437 | 0.75 | 0.10 | 0.54 | 0.10 | 0.38 | 0.10 | 0.28 | 0.05 |
| 48 | PE-GP437 2 L-doses | | 0.58 | 0.14 | 0.34 | 0.10 | 0.22 | 0.10 | 0.25 | 0.06 |
| 49 | Inject (H dose) | — | 1.50 | 0.20 | 0.10 | 0.30 | 0.58 | 0.20 | 0.25 | 0.06 |

TABLE 32

| Group no. (n = 3) | Serum anti-GP417 & 437 IgA activity in ELISA-Test Vaccine | Enhancer | dilx 200 Average | Stdev | dilx 500 Average | Stdev | dilx 1250 Average | Stdev | dilx 3125 Average | Stdev |
|---|---|---|---|---|---|---|---|---|---|---|
| 40 | Blank | — | 0.28 | 0.10 | 0.27 | 0.03 | 0.21 | 0.08 | 0.21 | 0.03 |
| 41 | PE-GP417 | CO1-PE-GP417 | 0.65 | 0.12 | 0.38 | 0.08 | 0.29 | 0.05 | 0.24 | 0.04 |
| 42 | PE-GP417 | DQ2-PE-GP417 | 0.70 | 0.10 | 0.45 | 0.05 | 0.28 | 0.05 | 0.26 | 0.10 |
| 43 | PE-GP417 | RV3-PE-GP417 | 0.60 | 0.12 | 0.38 | 0.06 | 0.27 | 0.06 | 0.28 | 0.10 |
| 44 | PE-GP417 2 L-dose | | 0.50 | 0.11 | 0.31 | 0.13 | 0.25 | 0.10 | 0.22 | 0.10 |
| 45 | PE-GP437 | CO1-PE-GP437 | 0.59 | 0.15 | 0.39 | 0.09 | 0.28 | 0.03 | 0.22 | 0.06 |
| 46 | PE-GP437 | DQ2-PE-GP437 | 0.81 | 0.11 | 0.45 | 0.10 | 0.31 | 0.05 | 0.27 | 0.07 |
| 47 | PE-GP437 | RV3-PE-GP437 | 0.72 | 0.14 | 0.48 | 0.11 | 0.34 | 0.05 | 0.27 | 0.05 |
| 48 | PE-GP437 2 L-doses | | 0.53 | 0.10 | 0.29 | 0.13 | 0.26 | 0.05 | 0.22 | 0.09 |
| 49 | Inject (H dose) | — | 0.80 | 0.20 | 0.50 | 0.15 | 0.30 | 0.08 | 0.23 | 0.04 |

From the results shown in Table 32, the GP417 and GP437-specific IgA activity in PE-GP417 and PE-GP437 vaccine were slightly enhanced by the mucosal targeting epitopes, including CO1, DQ2 and RV3 (p>0.02).

In Tables 33 and 34, the data showed that serum virus-neutralization (VN) antibodies has increased when PE-based GP417&437 and GP317 fused oral vaccines additional with the mucosal targeting ligands, CO1, DQ2 and RV3.

TABLE 33

Serum titers of the oral vaccine immunization in the experiment group in mice model

| Group no. (n = 3) | Group treatment Oral vaccine | Enhancer | IgG-ELISA titers (S/P) coating antigen GP417 & 437 | PRRSV TC-01 in Alveolar macrophage 3D4/31 VN titers |
|---|---|---|---|---|
| 40 | Blank | — | 0 | 0 |
| 41 | PE-GP417 | CO1-PE-GP417 | 149 | 16 |
| 42 | PE-GP417 | DQ2-PE-GP417 | 207 | 32 |
| 43 | PE-GP417 | RV3-PE-GP417 | 167 | 16 |
| 44 | PE-GP417 2 L-doses | | 63 | 8 |
| 45 | PE-GP437 | CO1-PE-GP437 | 161 | 16 |
| 46 | PE-GP437 | DQ2-PE-GP437 | 230 | 32 |
| 47 | PE-GP437 | RV3-PE-GP437 | 178 | 16 |
| 48 | PE-GP437 2 L-doses | | 64 | 8 |
| 49 | Inject (H dose) | — | 500 | 64 |

TABLE 34

| Group no. (n = 3) | Serum anti-GP317 IgG activity in ELISA-Test Vaccine | Enhancer | dilx 200 Average | Stdev | dilx 500 Average | Stdev |
|---|---|---|---|---|---|---|
| 50 | Blank | — | 0.28 | 0.10 | 0.22 | 0.08 |
| 51 | PE-GP317 | CO1-PE-G-P317 | 0.50 | 0.10 | 0.35 | 0.06 |

TABLE 34-continued

| | | | | | | |
|---|---|---|---|---|---|---|
| 52 | PE-GP317 | DQ2-PE-GP317 | 0.62 | 0.10 | 0.51 | 0.07 |
| 53 | PE-GP317 | RV3-PE-GP317 | 0.58 | 0.10 | 0.44 | 0.07 |
| 54 | PE-GP317 2 L-doses | | 0.52 | 0.10 | 0.46 | 0.11 |
| 55 | Inject (H dose) | — | 0.88 | 0.12 | 0.68 | 0.10 |

| Group no. (n = 3) | Serum anti-GP317 IgG activity in ELISA-Test Oral vaccine | Enhancer | IgG-ELISA titers (S/P) GP317 | PRRSV TC-01 in Alveolar VN titers |
|---|---|---|---|---|
| 50 | Blank | — | 0 | 0 |
| 51 | PE-GP317 | CO1-PE-GP317 | 141 | 8 |
| 52 | PE-GP317 | DQ2-PE-GP317 | 315 | 32 |
| 53 | PE-GP317 | RV3-PE-GP317 | 239 | 8 |
| 54 | PE-GP317 2 L-doses | | 261 | 8 |
| 55 | Inject (H dose) | — | 500 | 32 |

From the results shown in Tables 31 and 32, only the group of No. 42, 46, 52 had the highest level of VN titers. The oral administration of PE-GP317, PE-GP414 and PE-GP437 vaccine without the immune enhancer, such as the group no. 44, 48 and 54, all showed a lower VN titers and only 8 score. However, the DQ2 fused polypeptide, which proposed a good mucosal targeting ligand, demonstrated a good immune enhancing efficacy when it added into vaccine groups such as the group No. 42, 46 and 52.

13. Pigs Experiment: Oral Administration of M-Cell Ligand Chimeric Polypeptides Enhancing the Swine Antibody Titer Against Specific Antigen The vaccination program and examination of immune enhancement effect of the fusion biogenic polypeptides in swine tests is shown in Table 21.

In pig oral vaccine experiment of PE-M14 H-dose group without enhancer, there were no interaction effects of age x dietary program on growth performance from weaning to 10 weeks of age. The PE-M14 H-dose group did not affect growth performance from weaning to 10 weeks of age. It had no effect (P>0.05) on pig weight at 10 weeks of age. However, preweaning ADG (0.172 kg/day for ≤0.104 kg birth weight to 0.27 kg/day for ≥1.99 kg birth weight), weaning weight (5.26 kg to 8.85 kg), weaning BCS (2.69 to 2.93), and preweaning mortality (24.2% to 4.6%) were improved for pigs of heavier birth weight categories.

Over the entire 5-wk postweaning phase, PE-M14 H-dose oral vaccine additional with DQ2-PE-M14 or DQ2-PE-M27 enhancer group, the piglets had a 23-24% higher weight gain (P<0.05) and showed more play behavior (4.0±0.3 vs. 2.8±0.3 freq/h, P<0.05) than that of placebo group.

TABLE 35

| Vaccine group (N = 3) L dose/3 times/per week and 12 times orally/4 weeks | | Immune enhancer (N = 3) L dose/3 times/per week and 12 times orally/4 weeks | | IgG-ELISA titers (S/P) coating antigens: GP417, GP437 and GP 317 | PRRSV TC-01 in Alveolar macrophage 3D4/31 VN titers |
|---|---|---|---|---|---|
| Blank | 0 dose | — | 0 dose | 1 | 0 |
| PE-GP417, 437, 317 | L dose | DQ2-PE-GP417 | L dose | 320 | 32 |
| PE-GP417, 437, 317 and PE-GP-417 | L dose<br>L dose | | | 160 | 16 |
| PE-GP417, 437, 317 | H dose | — | — | 160 | 8 |
| Positive control through intramuscular injection (N = 3) | | | | 640 | 128 |

From the data shown in Table 33, the IgG-ELISA and VN titers in oral vaccine groups were lower than that of injection groups. VN titers could increase the score when the oral vaccine additional with DQ2-PE-GP417. It showed that DQ2 fused polypeptide, which proposed a good mucosal targeting ligand, demonstrated a good immune enhancer for PE-based PRRSV-NT oral vaccine.

In conclusion, when the vaccine is used with a fusion polypeptide of the present disclosure, good immune response can be achieved when the composition is orally administered. Especially, when the fusion polypeptide of the present disclosure comprises a mucosa targeting polypeptide, the immune response is significantly increased.

Although the present disclosure has been explained in relation to its embodiment, it is to be understood that many other possible modifications and variations can be made without departing from the spirit and scope of the disclosure as hereinafter claimed.

What is claimed is:

1. A fusion polypeptide, comprising:

(a) a mucosa targeting polypeptide, wherein the mucosa targeting polypeptide comprises an amino acid sequence selected from SEQ ID NOs: 1 to 4;

(b) a first translocating peptide for translocation; and (c) a first epitope-containing peptide.

2. The fusion polypeptide of claim 1, wherein the mucosa targeting polypeptide is located at an N-terminal of the fusion polypeptide, the first epitope-containing peptide is located at a C-terminal of the fusion polypeptide, and the first translocation peptide is located between the mucosa targeting polypeptide and the first epitope-containing peptide.

3. The fusion polypeptide of claim 1, wherein the first translocating peptide is from *pseudomonas* exotoxin.

4. The fusion polypeptide of claim 1, wherein the first translocating peptide comprises a *pseudomonas* exotoxin A fragment deleted of only domain III.

5. The fusion polypeptide of claim 1, wherein the first epitope-containing peptide is a Th1 antigenic epitope.

6. The fusion polypeptide of claim 1, wherein the first epitope-containing peptide is an HPV antigenic epitope, a Myostatin epitope, or a PRRS V antigenic epitope.

7. The fusion polypeptide of claim 6, wherein the HPV antigenic epitope is an E7 peptide sequence or an E6 peptide sequence of human papillomavirus type 16.

8. The fusion polypeptide of claim 1, wherein the first epitope-containing peptide is selected from SEQ ID NOs: 10, 12, 17, 18, 21, 22 and 23.

9. A method for enhancing a stimulation of an immune response, comprising:

administering a composition to a subject in need, wherein the composition comprises a vaccine and a fusion polypeptide, and the fusion polypeptide comprises:

(a) a mucosa targeting polypeptide, wherein the mucosa targeting polypeptide comprises an amino acid sequence selected from SEQ ID NOs: 1 to 4;

(b) a first translocating peptide for translocation; and (c) a first epitope-containing peptide.

10. The method of claim 9, wherein the mucosa targeting polypeptide is located at an N-terminal of the fusion polypeptide, the first epitope-containing peptide is located at a C-terminal of the fusion polypeptide, and the first translocation peptide is located between the mucosa targeting polypeptide and the first epitope-containing peptide.

11. The method of claim 9, wherein the first translocating peptide is from *pseudomonas* exotoxin.

12. The method of claim 9, wherein the first translocating peptide comprises a *pseudomonas* exotoxin A fragment deleted of only domain III.

13. The method of claim 9, wherein the first epitope-containing peptide is a Th1 antigenic epitope.

14. The method of claim 9, wherein the first epitope-containing peptide is an HPV antigenic epitope, a Myostatin epitope, or a PRRSV antigenic epitope.

15. The method of claim 14, wherein the HPV antigenic epitope is an E7 peptide sequence or an E6 peptide sequence of human papillomavirus type 16.

16. The method of claim 9, wherein the first epitope-containing peptide is selected from SEQ ID NOs: 10, 12, 17, 18, 21, 22 and 23.

17. The method of claim 9, wherein the composition is orally administered to the subject in need.

18. The method of claim 9, wherein the vaccine comprises: a second translocation peptide for translocation and a second antigenic epitope.

19. The method of claim 18, wherein the second translocating peptide is from *pseudomonas* exotoxin.

20. The method of claim 18, wherein the second translocating peptide comprises a *pseudomonas* exotoxin A fragment deleted of only domain III.

21. The method of claim 18, wherein the second antigenic epitope is a Th1 antigenic epitope.

22. The method of claim 18, wherein the second antigenic epitope is an HPV antigenic epitope, a Myostatin epitope, or a PRRSV antigenic epitope.

23. The method of claim 9, wherein the vaccine is an anti-HPV vaccine, an anti-Myostatin vaccine or an anti-PRRSV vaccine.

24. A fusion polypeptide, comprising:

(b) a first translocating peptide for translocation; and (c) a first antigenic epitope selected from SEQ ID NOs: 10 and 12.

25. The fusion polypeptide of claim 24, wherein the first translocating peptide is from *pseudomonas* exotoxin.

26. The fusion polypeptide of claim 24, wherein the first translocating peptide comprises a *pseudomonas* exotoxin A fragment deleted of only domain III.

27. A method for treating or preventing HPV, comprising:

administering a composition to a subject in need, wherein the composition comprises an anti-HPV vaccine and a fusion polypeptide, and the fusion polypeptide comprises:

(b) a first translocating peptide for translocation; and (c) a first antigenic epitope selected from SEQ ID NOs: 10 and 12.

28. The method of claim 27, wherein the first translocating peptide is from *pseudomonas* exotoxin.

29. The method of claim 27, wherein the first translocating peptide comprises a *pseudomonas* exotoxin A fragment deleted of only domain III.

30. The method of claim 27, wherein the composition is orally administered to the subject in need.

31. The method of claim 27, wherein the vaccine comprises: a second translocation peptide for translocation and a HPV antigenic epitope.

32. The method of claim 31, wherein the second translocating peptide is from *pseudomonas* exotoxin.

33. The method of claim 31, wherein the second translocating peptide comprises a *pseudomonas* exotoxin A fragment deleted of only domain III.

* * * * *

SEQUENCE LISTING

<160> NUMBER OF SEQ ID NOS: 82

<210> SEQ ID NO 1
<211> LENGTH: 14
<212> TYPE: PRT
<213> ORGANISM: Homo sapiens

<400> SEQUENCE: 1

Ser Phe His Gln Leu Pro Ala Arg Ser Pro Ala Pro Leu Gln
1 5 10

<210> SEQ ID NO 2
<211> LENGTH: 22
<212> TYPE: PRT
<213> ORGANISM: Daedalea quercina Fr.

<400> SEQUENCE: 2

Ser Ser Phe His Leu Phe His His Leu Pro Ala Arg Ala Pro Leu Ala
1 5 10 15

Pro Ser Glu Leu Gln Pro
20

```
<210> SEQ ID NO 3
<211> LENGTH: 17
<212> TYPE: PRT
<213> ORGANISM: Dasypus novemcinctus

<400> SEQUENCE: 3

Ser Thr Pro Phe His Pro Leu Pro Ala Arg Lys Pro Leu Pro Leu Gln
1               5                   10                  15

Pro

<210> SEQ ID NO 4
<211> LENGTH: 212
<212> TYPE: PRT
<213> ORGANISM: Human papillomavirus

<400> SEQUENCE: 4

Glu Phe His Met Val Asp Gly Met Ser Ile Arg Ala Lys Arg Arg Lys
1               5                   10                  15

Arg Ala Ser Ala Thr Gln Leu Tyr Lys Thr Cys Lys Gln Ala Gly Thr
                20                  25                  30

Cys Pro Pro Asp Ile Ile Pro Lys Val Glu Gly Lys Thr Ile Ala Glu
            35                  40                  45

Gln Ile Leu Gln Tyr Gly Ser Met Gly Val Phe Phe Gly Gly Leu Gly
    50                  55                  60

Ile Gly Thr Gly Ser Gly Thr Gly Gly Arg Thr Gly Tyr Ile Pro Leu
65                  70                  75                  80

Gly Thr Arg Pro Pro Thr Ala Thr Asp Thr Leu Ala Pro Val Arg Pro
                85                  90                  95

Pro Leu Thr Val Asp Pro Val Gly Pro Ser Asp Pro Ser Ile Val Ser
            100                 105                 110

Leu Val Glu Glu Thr Ser Phe Ile Asp Ala Gly Ala Pro Thr Ser Val
        115                 120                 125

Pro Ser Ile Pro Pro Asp Val Ser Gly Phe Ser Ile Thr Thr Ser Thr
    130                 135                 140

Asp Thr Thr Pro Ala Ile Leu Asp Ile Asn Asn Asn Thr Val Thr Thr
145                 150                 155                 160

Val Thr Thr His Asn Asn Pro Thr Phe Thr Asp Pro Ser Val Leu Gln
                165                 170                 175

Pro Pro Thr Pro Ala Glu Thr Gly Gly His Phe Thr Leu Ser Ser Ser
            180                 185                 190

Thr Ile Ser Thr His Asn Tyr Glu Glu Ile Pro Met Asp Thr Lys Asp
        195                 200                 205

Glu Leu Leu Glu
    210

<210> SEQ ID NO 5
<211> LENGTH: 78
<212> TYPE: DNA
<213> ORGANISM: Artificial sequence
<220> FEATURE:
<223> OTHER INFORMATION: CO-1 DNA sequence

<400> SEQUENCE: 5

gaattcagca gctttcatct gttccaccat ctgccagcgc gtgcgccatt agcgccttct    60

gaattacagc ccctcgag                                                 78
```

<210> SEQ ID NO 6
<211> LENGTH: 78
<212> TYPE: DNA
<213> ORGANISM: Artificial sequence
<220> FEATURE:
<223> OTHER INFORMATION: DQ-2 DNA sequence

<400> SEQUENCE: 6
gaattcagca gctttcatct gttccaccat ctgccagcgc gtgcgccatt agcgccttct 60
gaattacagc ccctcgag 78

<210> SEQ ID NO 7
<211> LENGTH: 63
<212> TYPE: DNA
<213> ORGANISM: Artificial sequence
<220> FEATURE:
<223> OTHER INFORMATION: RV-3 DNA sequence

<400> SEQUENCE: 7
gaattctcta ctcctttcca cccattgcct gcccgcaaac cattgcctct ggtgcccctc 60
gag 63

<210> SEQ ID NO 8
<211> LENGTH: 636
<212> TYPE: DNA
<213> ORGANISM: Human papillomavirus

<400> SEQUENCE: 8
gaattccata tggtcgacgg tatgtccatc cgtgctaaac gtcgtaaacg tgcttccgct 60
acccagctgt acaaaacctg caaacaggct ggtacctgcc cgccggacat catcccgaaa 120
gttgaaggta aaaccatcgc tgaacagatc ctgcaatacg gttctatggg tgttttcttc 180
ggcggtctgg gcatcggtac cggttccggt actggcggtc gtaccggtta catcccgctg 240
ggtacccgtc cgccgaccgc taccgacacc ctggctccgg ttcgtccgcc gctgaccgtt 300
gacccggttg gtccgtccga cccgtccatc gtttccctgg ttgaagaaac ctccttcatc 360
gacgctggtg ctccgacctc cgttccgtcc atcccgccgg acgtttccgg tttctccatc 420
accacctcca ccgacactac cccggctatc ctggacatca acaacaacac cgttactacc 480
gtaaccactc acaacaaccc gaccttcacc gacccgtccg ttctgcaacc gccgaccccg 540
gctgaaaccg gtggtcactt caccctgtcc tcttccacca tctccaccca caactacgaa 600
gaaatcccga tggacaccaa agacgaactg ctcgag 636

<210> SEQ ID NO 9
<211> LENGTH: 47
<212> TYPE: PRT
<213> ORGANISM: Artificial sequence
<220> FEATURE:
<223> OTHER INFORMATION: fused peptide

<400> SEQUENCE: 9

Glu Phe Val Asp Gln Leu Leu Arg Arg Glu Val Phe Cys Gly Phe Arg
1               5                   10                  15

Asp Leu Val Tyr Asp Phe Ala Phe Ser Asp Leu Lys Leu Pro Gln Leu
            20                  25                  30

Cys Thr Glu Leu Lys Leu Pro Gln Leu Cys Thr Glu Leu Leu Glu
        35                  40                  45

<210> SEQ ID NO 10
<211> LENGTH: 96

<212> TYPE: PRT
<213> ORGANISM: Artificial sequence
<220> FEATURE:
<223> OTHER INFORMATION: fused peptide

<400> SEQUENCE: 10

```
Glu Phe Val Asp Lys Asp Glu Leu Arg Glu Val Tyr Asn Phe Ala Phe
1               5                   10                  15

Leu Leu Val Leu Arg Arg Glu Val Tyr Asp Lys Asp Glu Leu Leu Leu
            20                  25                  30

Leu Leu Glu Asp Arg Gln Leu Leu Arg Arg Glu Val Phe Cys Gly Phe
        35                  40                  45

Arg Asp Leu Leu Glu Asp Arg Val Tyr Asp Phe Ala Phe Ser Asp Leu
    50                  55                  60

Lys Leu Pro Gln Leu Cys Thr Glu Leu Lys Leu Pro Gln Leu Cys Thr
65                  70                  75                  80

Glu Leu Lys Asp Glu Leu Lys Asp Glu Leu Val Leu Leu Leu Leu Glu
                85                  90                  95
```

<210> SEQ ID NO 11
<211> LENGTH: 51
<212> TYPE: PRT
<213> ORGANISM: Artificial sequence
<220> FEATURE:
<223> OTHER INFORMATION: fused peptide

<400> SEQUENCE: 11

```
Glu Phe Val Asp Gln Ala Glu Pro Asp Gln Ala Glu Pro Asp Arg Ala
1               5                   10                  15

Arg Ala His Tyr Asn Ile Arg Ala Arg Ala His Tyr Asn Ile Leu Arg
            20                  25                  30

Ala His Tyr Asn Ile Val Ile Phe Arg Ala His Tyr Asn Ile Val Ile
        35                  40                  45

Phe Leu Glu
    50
```

<210> SEQ ID NO 12
<211> LENGTH: 70
<212> TYPE: PRT
<213> ORGANISM: Artificial sequence
<220> FEATURE:
<223> OTHER INFORMATION: fused peptide

<400> SEQUENCE: 12

```
Glu Phe Val Asp Gln Ala Glu Pro Asp Gln Ala Glu Pro Asp Arg Asp
1               5                   10                  15

Glu Leu Val Leu Arg Ala Arg Ala His Tyr Asn Ile Arg Ala Arg Ala
            20                  25                  30

His Tyr Asn Ile Leu Glu Asp Arg Leu Leu Val Leu Arg Ala His Tyr
        35                  40                  45

Asn Ile Val Ile Phe Arg Ala His Tyr Asn Ile Val Ile Phe Lys Asp
    50                  55                  60

Glu Leu Leu Val Leu Glu
65                  70
```

<210> SEQ ID NO 13
<211> LENGTH: 153
<212> TYPE: DNA
<213> ORGANISM: Artificial sequence
<220> FEATURE:
<223> OTHER INFORMATION: E601 DNA sequence

<400> SEQUENCE: 13
gaattcgtcg accaactgtt gcgtcgtgaa gttttctgtg gctttcgtga tctggtctat 60
gacttcgcct ttagtgattt gaagctgcca caattgtgta cggaactgaa actgcctcaa 120
ctgtgtacag aactgaagga tgagctgctc gag 153

<210> SEQ ID NO 14
<211> LENGTH: 288
<212> TYPE: DNA
<213> ORGANISM: Artificial sequence
<220> FEATURE:
<223> OTHER INFORMATION: E622 DNA sequence

<400> SEQUENCE: 14
gaattcgtcg acaaagatga actgcgtgag gtgtataact ttgcgttcct gttagtgtta 60
cgccgtgagg tttatgacaa ggacgagttg ttactgctgt tagaagatcg ccaactgttg 120
cgtcgtgaag ttttctgtgg ctttcgtgat ctgttagaag accgcgtcta tgacttcgcc 180
tttagtgatt tgaagctgcc acaattgtgt acggaactga aactgcctca actgtgtaca 240
gaactgaagg atgagctgaa agatgaatta gtgctgttat tgctcgag 288

<210> SEQ ID NO 15
<211> LENGTH: 150
<212> TYPE: DNA
<213> ORGANISM: Artificial sequence
<220> FEATURE:
<223> OTHER INFORMATION: E701 DNA sequence

<400> SEQUENCE: 15
gaattcgtcg accaggcgga accagatcaa gcggaacctg accgtgcccg cgcacattat 60
aacattcgcg cacgtgcaca ctataatctg gaggcgcatt ataacattgt catcttccgc 120
gcacattata acatcgtcat tttcctcgag 150

<210> SEQ ID NO 16
<211> LENGTH: 207
<212> TYPE: DNA
<213> ORGANISM: Artificial sequence
<220> FEATURE:
<223> OTHER INFORMATION: E713 DNA sequence

<400> SEQUENCE: 16
gaattcgtcg accaggcgga accagatcaa gcggaacctg accgtgacga gctggtgtta 60
cgcgcccgcg cacattataa cattcgcgca cgtgcacact ataatctgga ggatcgttta 120
ctggtcttgc gtgcgcatta taacattgtc atcttccgcg cacattataa catcgtcatt 180
ttcaaagatg agttgctggt tctcgag 207

<210> SEQ ID NO 17
<211> LENGTH: 72
<212> TYPE: PRT
<213> ORGANISM: Artificial sequence
<220> FEATURE:
<223> OTHER INFORMATION: fused peptide

<400> SEQUENCE: 17

Glu Phe Val Asp Val Phe Leu Gln Lys Tyr Pro His Thr His Leu Val
1               5                   10                  15

His Gln Ala Leu Asp Val Phe Leu Gln Lys Tyr Pro His Thr His Leu
            20                  25                  30

Val His Gln Ala Leu Asp Val Phe Leu Gln Lys Tyr Pro His Thr His
        35                  40                  45

Leu Val His Gln Ala Leu Asp Val Phe Leu Gln Lys Tyr Pro His Thr
    50                  55                  60

His Leu Val His Gln Ala Leu Glu
65                  70

<210> SEQ ID NO 18
<211> LENGTH: 277
<212> TYPE: PRT
<213> ORGANISM: Artificial sequence
<220> FEATURE:
<223> OTHER INFORMATION: fused peptide

<400> SEQUENCE: 18

Glu Phe Leu Leu Glu Pro His Thr His Leu Val His Gln Ala Asn Val
1               5                   10                  15

Leu Leu Ala Leu Gln Leu Leu Leu Glu Asp Arg Glu Phe Val Phe Leu
            20                  25                  30

Gln Lys Tyr Pro His Val Glu Pro His Thr His Leu Val His Gln Ala
        35                  40                  45

Asn Val Leu Leu Ala Leu Gln Leu Leu Leu Glu Asp Arg Glu Phe Val
    50                  55                  60

Phe Leu Gln Lys Tyr Pro His Val Glu Pro His Thr His Leu Val His
65                  70                  75                  80

Gln Ala Asn Val Leu Leu Ala Leu Gln Leu Leu Leu Glu Asp Arg Glu
                85                  90                  95

Phe Val Phe Leu Gln Lys Tyr Pro His Val Glu Pro His Thr His Leu
            100                 105                 110

Val His Gln Ala Asn Val Leu Leu Ala Leu Gln Leu Leu Leu Glu Asp
        115                 120                 125

Arg Glu Phe Val Phe Leu Gln Lys Tyr Pro His Val Glu Pro His Thr
    130                 135                 140

His Leu Val His Gln Ala Asn Val Leu Leu Ala Leu Gln Leu Leu Leu
145                 150                 155                 160

Glu Asp Arg Glu Phe Val Phe Leu Gln Lys Tyr Pro His Val Glu Pro
                165                 170                 175

His Thr His Leu Val His Gln Ala Asn Val Leu Leu Ala Leu Gln Leu
            180                 185                 190

Leu Leu Glu Asp Arg Glu Phe Val Phe Leu Gln Lys Tyr Pro His Val
        195                 200                 205

Glu Pro His Thr His Leu Val His Gln Ala Asn Val Leu Leu Ala Leu
    210                 215                 220

Gln Leu Leu Leu Glu Asp Arg Glu Phe Val Phe Leu Gln Lys Tyr Pro
225                 230                 235                 240

His Val Glu Pro His Thr His Leu Val His Gln Ala Asn Val Leu Leu
                245                 250                 255

Ala Leu Gln Leu Leu Leu Glu Asp Arg Glu Phe Val Phe Leu Gln Lys
            260                 265                 270

Tyr Pro His Val Asp
        275

<210> SEQ ID NO 19
<211> LENGTH: 216
<212> TYPE: DNA
<213> ORGANISM: Artificial sequence
<220> FEATURE:

-continued

<223> OTHER INFORMATION: M14 DNA sequence

<400> SEQUENCE: 19
gaattcgtcg acgtgttttt acaaaaatat cctcatacgc acctggtcca tcaggcgctc 60
gacgtgtttt tacaaaaata tcctcatacg cacctggtcc atcaggcgct cgacgtgttt 120
ttacaaaaat atcctcatac gcacctggtc catcaggcgc tcgacgtgtt tttacaaaaa 180
tatcctcata cgcacctggt ccatcaggcg ctcgag 216

<210> SEQ ID NO 20
<211> LENGTH: 831
<212> TYPE: DNA
<213> ORGANISM: Artificial sequence
<220> FEATURE:
<223> OTHER INFORMATION: M27 DNA sequence

<400> SEQUENCE: 20
gaattcctcc tcgagccaca tacgcactta gtgcatcaag cgaacgtttt gctggcactg 60
caattattat tagaagatcg tgaatttgtc ttcttgcaaa aatatccaca cgtcgagcca 120
catacgcact tagtgcatca agcgaacgtt ttgctggcac tgcaattatt attagaagat 180
cgtgaatttg tcttcttgca aaaatatcca cacgtcgagc cacatacgca cttagtgcat 240
caagcgaacg ttttgctggc actgcaatta ttattagaag atcgtgaatt tgtcttcttg 300
caaaaatatc cacacgtcga gccacatacg cacttagtgc atcaagcgaa cgttttgctg 360
gcactgcaat tattattaga agatcgtgaa tttgtcttct tgcaaaaata tccacacgtc 420
gagccacata cgcacttagt gcatcaagcg aacgttttgc tggcactgca attattatta 480
gaagatcgtg aatttgtctt cttgcaaaaa tatccacacg tcgagccaca tacgcactta 540
gtgcatcaag cgaacgtttt gctggcactg caattattat tagaagatcg tgaatttgtc 600
ttcttgcaaa aatatccaca cgtcgagcca catacgcact tagtgcatca agcgaacgtt 660
ttgctggcac tgcaattatt attagaagat cgtgaatttg tcttcttgca aaaatatcca 720
cacgtcgagc cacatacgca cttagtgcat caagcgaacg ttttgctggc actgcaatta 780
ttattagaag atcgtgaatt tgtcttcttg caaaaatatc cacacgtcga c 831

<210> SEQ ID NO 21
<211> LENGTH: 297
<212> TYPE: PRT
<213> ORGANISM: Porcine reproductive and respiratory syndrome virus

<400> SEQUENCE: 21

Glu Phe Val Ser Phe Ser Thr Gly Gly Ser Gln Asn Trp Thr Val Glu
1 5 10 15

Arg Leu Leu Gln Ala Glu Phe Cys Ser Thr Ser Gln Ala Ala Arg Gln
20 25 30

Arg Leu Glu Thr Gly Arg Asn Cys Ser Thr Gly Gln Ala Ala Arg Gln
35 40 45

Arg Leu Glu Pro Gly Arg Asn Leu Val Leu Cys Leu Thr Ser Gln Ala
50 55 60

Ala Gln Gln Arg Leu Glu Pro Gly Gly Asn Cys Gln Thr Ser Gln Ala
65 70 75 80

Ala His Gln Arg Leu Glu Pro Gly Arg Asn Cys Arg Thr Ser Gln Ala
85 90 95

Ala Ser Gln Arg Leu Glu Pro Gly Arg Asn Cys Arg Thr Ser Gln Ala
100 105 110

-continued

```
Ala His Gln Arg Leu Glu Pro Gly Arg Asn Cys Ser Thr Arg Gln Ala
        115                 120                 125

Ala Gln Gln Arg Leu Glu Pro Gly Arg Asn Leu Leu Cys Pro Thr Ser
    130                 135                 140

Gln Ala Ala His Gln Arg Arg Leu Glu Pro Gly Arg Asn Cys Ser Thr
145                 150                 155                 160

Ser Gln Ala Ala Tyr Gln Arg Leu Glu Pro Gly Arg Asn Cys Pro Thr
                165                 170                 175

Ser Arg Ala Ala Arg Gln Arg Leu Glu Pro Gly Arg Asn Leu Leu Cys
            180                 185                 190

Ser Thr Ser Gln Ala Ala Leu Gln Arg Leu Glu Pro Gly Arg Asn Leu
        195                 200                 205

Cys Pro Thr Ser Gln Ala Ala Lys Gln Arg Leu Glu Pro Gly Arg Asn
    210                 215                 220

Leu Val Val Cys Leu Thr Ser Gln Ala Ala Arg Gln Arg Leu Glu Pro
225                 230                 235                 240

Gly Arg Asn Cys Ser Thr Ser Gln Ala Ala Ser Gln Arg Leu Glu Pro
                245                 250                 255

Gly Arg Asn Cys Pro Thr Ser Gln Ala Ala Arg Gln Arg Leu Glu Pro
            260                 265                 270

Gly Arg Asn Val Leu Leu Leu Cys Leu Thr Ser Gln Ala Ala His Gln
        275                 280                 285

Arg Leu Glu Pro Gly Arg Asn Leu Glu
    290                 295


<210> SEQ ID NO 22
<211> LENGTH: 230
<212> TYPE: PRT
<213> ORGANISM: Porcine reproductive and respiratory syndrome virus

<400> SEQUENCE: 22

Glu Phe Gly Val Ser Ala Ala Gln Glu Lys Ile Ser Phe Gly Leu Leu
1               5                   10                  15

Gly Val Pro Thr Ala Gln Glu Thr Thr Ser Ile Arg Glu Val Leu Glu
            20                  25                  30

Val Ser Thr Ala Gln Glu Asn Ser Pro Phe Met Leu Gly Ala Ser Ala
        35                  40                  45

Thr Glu Glu Lys Thr Ser Leu Arg Leu Gly Ala Ser Thr Thr Gln Glu
    50                  55                  60

Thr Ser Phe Gly Lys Cys Leu Arg Pro His Gly Val Ser Ala Ala Gln
65                  70                  75                  80

Gly Thr Thr Pro Phe Arg Gly Val Ser Thr Thr Gln Glu Asn Thr Ser
                85                  90                  95

Phe Gly Arg Val Pro Thr Ala Gln Glu Asn Val Ser Phe Gly Leu His
            100                 105                 110

Gly Val Pro Ala Ala Gln Lys Thr Asn Ser Phe Gly Gly Val Pro Thr
        115                 120                 125

Ala Gln Glu Asn Ile Ser Phe Lys Glu Val Ser Ala Thr Gln Arg Glu
    130                 135                 140

Ile Pro Phe Arg Cys Leu Arg Pro His Gly Val Ser Thr Ala Gln Glu
145                 150                 155                 160

Thr Pro Phe Arg Gly Val Ser Thr Ala Gln Glu Thr Ile Pro Phe Arg
                165                 170                 175

Gly Val Ser Ala Thr His Glu Asn Ile Ser Phe Gly Cys Leu Arg Pro
            180                 185                 190
```

-continued

```
His Gly Val Ser Ala Ala Gln Glu Ser Ile Pro Ile Arg Leu Gly Ala
        195                 200                 205

Ser Ala Ala Gln Glu Asn Thr Ser Phe Arg Gly Thr Pro Ala Ala Gln
    210                 215                 220

Glu Lys Ile Pro Leu Glu
225                 230


<210> SEQ ID NO 23
<211> LENGTH: 289
<212> TYPE: PRT
<213> ORGANISM: Porcine reproductive and respiratory syndrome virus

<400> SEQUENCE: 23

Glu Phe Leu Gly Val Ser Ala Ala Gln Glu Arg Ile Pro Ile Arg Glu
1               5                   10                  15

Val Ser Ala Asp Lys Glu Val Ser Ala Glu Lys Lys Glu Ile Ser Phe
            20                  25                  30

Gly Val Ser Thr Ala Gln Gly Asn Ile Ser Phe Gly Leu Gly Val Ser
        35                  40                  45

Thr Ala Gln Glu Ala Ile Pro Phe Leu Ala Leu Gly Val Ser Thr Ala
    50                  55                  60

Gln Glu Thr Ile Pro Phe Gly Leu Leu Gly Val Ser Thr Ala Gln Gly
65                  70                  75                  80

Ile Ile Ser Phe Gly Gly Val Ser Thr Ala Gln Glu Asn Ile Ser Phe
                85                  90                  95

Gly Gly Val Ser Thr Ala Gln Glu Thr Ile Ser Phe Gly Leu Leu Gly
            100                 105                 110

Val Ser Thr Ala Gln Glu Asn Ile Ser Phe Gly Cys Leu Arg Thr His
        115                 120                 125

Glu Val Ser Ala Ala Gln Glu Lys Ile Ser Phe Gly Gly Val Ser Glu
    130                 135                 140

Ala Gln Lys Ile Ser Phe Gly Val Ser Ala Ala Gly Val Ser Ala Ala
145                 150                 155                 160

Gln Glu Glu Ile Pro Phe Gly Cys Leu Arg Pro His Gly Leu Pro Ala
                165                 170                 175

Ala Gln Glu Lys Thr Ser Phe Gly Gly Val Ser Ala Ala Gln Glu Lys
            180                 185                 190

Thr Ser Phe Gly Gly Val Ser Ala Ala Gln Glu Glu Phe Ser Phe Gly
        195                 200                 205

Cys Leu Arg Pro His Arg Val Ser Ala Ala Gln Glu Lys Ile Ser Phe
    210                 215                 220

Glu Val Ser Ala Leu Glu Val Ser Ala Ala Gln Glu Lys Ile Ser Phe
225                 230                 235                 240

Gly Val Ser Ala Ala Leu Gly Val Ser Ala Ala Gln Glu Lys Asn Ser
                245                 250                 255

Phe Gly Cys Leu Arg Pro His Gly Val Ser Ala Ala Gln Glu Lys Thr
            260                 265                 270

Ser Phe Gly Gly Val Ser Ala Ala Gln Lys Lys Ile Ser Phe Gly Leu
        275                 280                 285

Glu


<210> SEQ ID NO 24
<211> LENGTH: 892
<212> TYPE: DNA
<213> ORGANISM: Porcine reproductive and respiratory syndrome virus
```

<400> SEQUENCE: 24

```
ggaattcgtg agctttagca cgggtggcag ccagaactgg acggtggaac gtctgctgca     60
agccgagttc tgtagtactt ctcaggcggc gcgccagcgt ctggaaccag ggcgtaattg    120
ttctacaggc caggccgcac gtcaacgttt agagccaggt cgcaatttag ttttgtgtct    180
gacgagccag gccgcacagc agcgcttgga accaggcggt aactgtcaaa cttctcaagc    240
ggcccatcaa cgcctggaac caggtcgcaa ctgtcgcact agccaagccg ccagccaacg    300
tttagagcca ggccgcaact gtcgcacgag tcaggcggcg caccaacgtc tggaaccagg    360
ccgtaattgt agtacgcgcc aagcagccca gcaacgctta gaaccagggc gcaacctgtt    420
atgtccaact tctcaggcgg cccatcaacg ccgcttagaa ccagggcgta attgtagcac    480
gtctcaagca gcatatcaac gtctggaacc aggccgcaac tgtccaactt ctcgtgcggc    540
acgccagcgc ttagaaccag gtcgtaattt attatgttct actagccaag ccgcattaca    600
gcgtttagag ccagggcgta acctgtgtcc aactagccaa gcagcaaaac aacgcctgga    660
gccaggtcgt aatttagtgg tctgtttaac gagccaagcg gcgcgtcaac gcttagaacc    720
aggtcgcaat tgttctacta gccaagcggc cagtcaacgt ttagaaccag ggcgcaactg    780
tccaacgagc caagcggcgc gccaacgttt agagccaggg cgcaacgttt tattgttgtg    840
tctgacgagt caagccgccc atcaacgtct ggaaccaggt cgcaatctcg ag            892
```

<210> SEQ ID NO 25
<211> LENGTH: 696
<212> TYPE: DNA
<213> ORGANISM: Porcine reproductive and respiratory syndrome virus

<400> SEQUENCE: 25

```
gaattcggcg tgagcgcggc ccaggaaaag atcagtttcg gcctgttagg tgtgccaacg     60
gcccaagaga ctacaagtat tcgcgaggtt ttggaagtca gtactgcaca agaaaacagt    120
ccatttatgt taggcgcgag tgccacggag gaaaaaacgt ctttgcgcct gggggcaagc    180
acaacgcagg agacgagttt tggcaagtgt ttacgtccac atggggtttc tgcagcccaa    240
gggacgactc catttcgcgg tgtcagtaca acgcaagaaa acacgagttt tggtcgtgtc    300
ccaacggcac aagagaacgt gtcttttggc ctgcatggtg ttccagcagc gcaaaagacg    360
aacagcttcg gtggcgttcc aacggcacaa gaaaacatta gttttaagga ggttagtgcc    420
acgcaacgtg aaatcccatt ccgttgttta cgcccacacg ggttagcac agcccaggag    480
actccatttc gcggggtgag tactgcccag gagacgatcc cattccgtgg ggtttctgca    540
acgcatgaaa acatcagttt tgggtgtttg cgtccacatg gtgtcagcgc cgcacaggaa    600
tctattccaa tccgtctggg cgcgagcgca gcccaagaga ataccagttt tcgcgggaca    660
ccagcggcac aggagaaaat cccattggaa ctcgag                              696
```

<210> SEQ ID NO 26
<211> LENGTH: 870
<212> TYPE: DNA
<213> ORGANISM: Porcine reproductive and respiratory syndrome virus

<400> SEQUENCE: 26

```
gaattcctgg gcgtgagcgc agcccaagag cgcatcccaa ttcgcgaggt gagcgccgac     60
aaagaggtga gtgccgagaa gaaagagatc tctttcgggg tgagcaccgc gcagggtaat    120
atcagttttg gtttgggcgt cagcaccgca caggaggcaa ttccattctt ggcactgggg    180
```

gtcagtaccg cccaggaaac tattccattt ggcttgctgg gggttagcac tgcacaaggt 240
atcattagtt tcggcggggt ctctactgcg caggagaata tcagctttgg cggggttagt 300
actgcgcaag agaccattag ttttggtttg ctgggcgttt ctaccgccca ggagaatatt 360
agctttggtt gtttacgcac tcatgaagtt agtgccgcac aagagaaaat tagcttcggc 420
ggcgttagtg aagcgcaaga gaagattagt ttcggggtct ctgcagcagg cgtcagcgcc 480
gcccaagagg agattccatt tgggtgtctg cgcccacacg gcctgccagc ggcgcaggag 540
aaaaccagct tcggcggcgt tagtgccgcc caggaaaaga cctctttcgg tggtgtcagc 600
gcagcacaag aagagttctc ttttggttgt ttgcgcccac atcgtgttag tgccgcacag 660
gaaaagatca gctttgaagt tagcgcgctg gaagtcagtg ccgcgcaaga gaagattagt 720
tttggcgtta gcgcggcatt gggtgtcagc gcagcacaag aaaagaactc tttcggttgt 780
ttacgcccac acggtgttag cgccgcgcaa gagaaaacca gcttcggggg tgttagtgcc 840
gcacaaaaaa agatcagctt tgggctcgag 870

<210> SEQ ID NO 27
<211> LENGTH: 359
<212> TYPE: DNA
<213> ORGANISM: Artificial sequence
<220> FEATURE:
<223> OTHER INFORMATION: partial sequence of plasmid

<400> SEQUENCE: 27
gtttaacttt aagaaggaga tataccatgg ccgaacaatt ggtggacctc tggaacgaat 60
gcgccaaagc ctgcgtgctc gacctcaagg acggcgtgcg ttccagccgc atgagcgtcg 120
acccggccat cgccgacacc aacggccagg gcgtgctgca ctactgcatg gaattctctt 180
ttcatcagct gccagcgcgt tctccagccc cactgcagct cgagcatatg gccgaagaag 240
ctttcgacct ctggaacgaa tgcgccaaag cctgcgtgct cgacctcaag gacggcgtgc 300
gttccagccg catgagcgtc gagcaccacc accaccacca ctgagatccg gctgctaac 359

<210> SEQ ID NO 28
<211> LENGTH: 383
<212> TYPE: DNA
<213> ORGANISM: Artificial sequence
<220> FEATURE:
<223> OTHER INFORMATION: partial sequence of plasmid

<400> SEQUENCE: 28
gtttaacttt aagaaggaga tataccatgg ccgaacaatt ggtggacctc tggaacgaat 60
gcgccaaagc ctgcgtgctc gacctcaagg acggcgtgcg ttccagccgc atgagcgtcg 120
acccggccat cgccgacacc aacggccagg gcgtgctgca ctactgcatg gaattcagca 180
gctttcatct gttccaccat ctgccagcgc gtgcgccatt agcgccttct gaattacagc 240 cctcgagca tatggccgaa gaagctttcg acctctggaa cgaatgcgcc aaagcctgcg 300
tgctcgacct caaggacggc gtgcgttcca gccgcatgag cgtcgagcac caccaccacc 360
accactgaga tccggctgct aac 383

<210> SEQ ID NO 29
<211> LENGTH: 368
<212> TYPE: DNA
<213> ORGANISM: Artificial sequence
<220> FEATURE:
<223> OTHER INFORMATION: partial sequence of plasmid

<400> SEQUENCE: 29

-continued

```
gtttaacttt aagaaggaga tataccatgg ccgaacaatt ggtggacctc tggaacgaat     60

gcgccaaagc ctgcgtgctc gacctcaagg acggcgtgcg ttccagccgc atgagcgtcg    120

acccggccat cgccgacacc aacggccagg gcgtgctgca ctactgcatg gaattctcta    180

ctcctttcca cccattgcct gcccgcaaac cattgcctct ggtgcccctc gagcatatgg    240

ccgaagaagc tttcgacctc tggaacgaat gcgccaaagc ctgcgtgctc gacctcaagg    300

acggcgtgcg ttccagccgc atgagcgtcg agcaccacca ccaccaccac tgagatccgg    360

ctgctaac                                                             368
```

```
<210> SEQ ID NO 30
<211> LENGTH: 941
<212> TYPE: DNA
<213> ORGANISM: Artificial sequence
<220> FEATURE:
<223> OTHER INFORMATION: partial sequence of plasmid

<400> SEQUENCE: 30

gtttaacttt aagaaggaga tataccatgg ccgaacaatt ggtggacctc tggaacgaat     60

gcgccaaagc ctgcgtgctc gacctcaagg acggcgtgcg ttccagccgc atgagcgtcg    120

acccggccat cgccgacacc aacggccagg gcgtgctgca ctactgcatg gaattccata    180

tggtcgacgg tatgtccatc cgtgctaaac gtcgtaaacg tgcttccgct acccagctgt    240

acaaaaacctg caaacaggct ggtacctgcc cgccggacat catcccgaaa gttgaaggta    300

aaaccatcgc tgaacagatc ctgcaatacg gttctatggg tgttttcttc ggcggtctgg    360

gcatcggtac cggttccggt actggcggtc gtaccggtta catcccgctg ggtacccgtc    420

cgccgaccgc taccgacacc ctggctccgg ttcgtccgcc gctgaccgtt gacccggttg    480

gtccgtccga cccgtccatc gtttccctgg ttgaagaaac ctccttcatc gacgctggtg    540

ctccgacctc cgttccgtcc atcccgccgg acgtttccgg tttctccatc accacctcca    600

ccgacactac cccggctatc ctggacatca acaacaacac cgttactacc gtaaccactc    660

acaacaaccc gaccttcacc gacccgtccg ttctgcaacc gccgaccccg gctgaaaccg    720

gtggtcactt caccctgtcc tcttccacca tctccaccca caactacgaa gaaatcccga    780

tggacaccaa agacgaactg ctcgagcata tggccgaaga agctttcgac ctctggaacg    840

aatgcgccaa agcctgcgtg ctcgacctca aggacggcgt gcgttccagc cgcatgagcg    900

tcgagcacca ccaccaccac cactgagatc cggctgctaa c                        941
```

```
<210> SEQ ID NO 31
<211> LENGTH: 501
<212> TYPE: PRT
<213> ORGANISM: Artificial sequence
<220> FEATURE:
<223> OTHER INFORMATION: chimeric antigen

<400> SEQUENCE: 31

Met Gly Ser Ser His His His His His His Ser Ser Gly Leu Val Pro
1               5                   10                  15

Arg Gly Ser His Met Ala Glu Glu Ala Phe Asp Leu Trp Asn Glu Cys
            20                  25                  30

Ala Lys Ala Cys Val Leu Asp Leu Lys Asp Gly Val Arg Ser Ser Arg
        35                  40                  45

Met Ser Val Asp Pro Ala Ile Ala Asp Thr Asn Gly Gln Gly Val Leu
    50                  55                  60
```

```
His Tyr Ser Met Val Leu Glu Gly Gly Asn Asp Ala Leu Lys Leu Ala
65                  70                  75                  80

Ile Asp Asn Ala Leu Ser Ile Thr Ser Asp Gly Leu Thr Ile Arg Leu
                85                  90                  95

Glu Gly Gly Val Glu Pro Asn Lys Pro Val Arg Tyr Ser Tyr Thr Arg
            100                 105                 110

Gln Ala Arg Gly Ser Trp Ser Leu Asn Trp Leu Val Pro Ile Gly His
        115                 120                 125

Glu Lys Pro Ser Asn Ile Lys Val Phe Ile His Glu Leu Asn Ala Gly
    130                 135                 140

Asn Gln Leu Ser His Met Ser Pro Ile Tyr Thr Ile Glu Met Gly Asp
145                 150                 155                 160

Glu Leu Leu Ala Lys Leu Ala Arg Asp Ala Thr Phe Phe Val Arg Ala
                165                 170                 175

His Glu Ser Asn Glu Met Gln Pro Thr Leu Ala Ile Ser His Ala Gly
            180                 185                 190

Val Ser Val Val Met Ala Gln Thr Gln Pro Arg Arg Glu Lys Arg Trp
        195                 200                 205

Ser Glu Trp Ala Ser Gly Lys Val Leu Cys Leu Leu Asp Pro Leu Asp
    210                 215                 220

Gly Val Tyr Asn Tyr Leu Ala Gln Gln Arg Cys Asn Leu Asp Asp Thr
225                 230                 235                 240

Trp Glu Gly Lys Ile Tyr Arg Val Leu Ala Gly Asn Pro Ala Lys His
                245                 250                 255

Asp Leu Asp Ile Lys Pro Thr Val Ile Ser His Arg Leu His Phe Pro
            260                 265                 270

Glu Gly Gly Ser Leu Ala Ala Leu Thr Ala His Gln Ala Cys His Leu
        275                 280                 285

Pro Leu Glu Thr Phe Thr Arg His Arg Gln Pro Arg Gly Trp Glu Gln
    290                 295                 300

Leu Glu Gln Cys Gly Tyr Pro Val Gln Arg Leu Val Ala Leu Tyr Leu
305                 310                 315                 320

Ala Ala Arg Leu Ser Trp Asn Gln Val Asp Gln Val Ile Arg Asn Ala
                325                 330                 335

Leu Ala Ser Pro Gly Ser Gly Gly Asp Leu Gly Glu Ala Ile Arg Glu
            340                 345                 350

Gln Pro Glu Gln Ala Arg Leu Ala Leu Thr Leu Ala Ala Ala Glu Ser
        355                 360                 365

Glu Arg Phe Val Arg Gln Gly Thr Gly Asn Asp Glu Ala Gly Ala Ala
    370                 375                 380

Asn Ala Asp Val Val Ser Leu Thr Cys Pro Val Ala Ala Gly Glu Cys
385                 390                 395                 400

Ala Gly Pro Ala Asp Ser Gly Asp Ala Leu Leu Glu Arg Asn Tyr Pro
                405                 410                 415

Thr Gly Ala Glu Phe Leu Gly Asp Gly Gly Asp Val Ser Phe Ser Thr
            420                 425                 430

Arg Gly Thr Gln Asn Trp Thr Val Glu Arg Leu Leu Gln Ala Glu Phe
        435                 440                 445

Gln Leu Leu Arg Arg Glu Val Phe Cys Gly Phe Arg Asp Leu Val Tyr
    450                 455                 460

Asp Phe Ala Phe Ser Asp Leu Lys Leu Pro Gln Leu Cys Thr Glu Leu
465                 470                 475                 480

Lys Leu Pro Gln Leu Cys Thr Glu Leu Lys Asp Glu Leu Leu Glu His
```

```
                485                 490                 495

His His His His His
            500


<210> SEQ ID NO 32
<211> LENGTH: 500
<212> TYPE: PRT
<213> ORGANISM: Artificial sequence
<220> FEATURE:
<223> OTHER INFORMATION: chimeric antigen

<400> SEQUENCE: 32

Met Gly Ser Ser His His His His His His Ser Ser Gly Leu Val Pro
1               5                   10                  15

Arg Gly Ser His Met Ala Glu Glu Ala Phe Asp Leu Trp Asn Glu Cys
            20                  25                  30

Ala Lys Ala Cys Val Leu Asp Leu Lys Asp Gly Val Arg Ser Ser Arg
        35                  40                  45

Met Ser Val Asp Pro Ala Ile Ala Asp Thr Asn Gly Gln Gly Val Leu
    50                  55                  60

His Tyr Ser Met Val Leu Glu Gly Gly Asn Asp Ala Leu Lys Leu Ala
65                  70                  75                  80

Ile Asp Asn Ala Leu Ser Ile Thr Ser Asp Gly Leu Thr Ile Arg Leu
                85                  90                  95

Glu Gly Gly Val Glu Pro Asn Lys Pro Val Arg Tyr Ser Tyr Thr Arg
            100                 105                 110

Gln Ala Arg Gly Ser Trp Ser Leu Asn Trp Leu Val Pro Ile Gly His
        115                 120                 125

Glu Lys Pro Ser Asn Ile Lys Val Phe Ile His Glu Leu Asn Ala Gly
    130                 135                 140

Asn Gln Leu Ser His Met Ser Pro Ile Tyr Thr Ile Glu Met Gly Asp
145                 150                 155                 160

Glu Leu Leu Ala Lys Leu Ala Arg Asp Ala Thr Phe Phe Val Arg Ala
                165                 170                 175

His Glu Ser Asn Glu Met Gln Pro Thr Leu Ala Ile Ser His Ala Gly
            180                 185                 190

Val Ser Val Val Met Ala Gln Thr Gln Pro Arg Arg Glu Lys Arg Trp
        195                 200                 205

Ser Glu Trp Ala Ser Gly Lys Val Leu Cys Leu Leu Asp Pro Leu Asp
    210                 215                 220

Gly Val Tyr Asn Tyr Leu Ala Gln Gln Arg Cys Asn Leu Asp Asp Thr
225                 230                 235                 240

Trp Glu Gly Lys Ile Tyr Arg Val Leu Ala Gly Asn Pro Ala Lys His
                245                 250                 255

Asp Leu Asp Ile Lys Pro Thr Val Ile Ser His Arg Leu His Phe Pro
            260                 265                 270

Glu Gly Gly Ser Leu Ala Ala Leu Thr Ala His Gln Ala Cys His Leu
        275                 280                 285

Pro Leu Glu Thr Phe Thr Arg His Arg Gln Pro Arg Gly Trp Glu Gln
    290                 295                 300

Leu Glu Gln Cys Gly Tyr Pro Val Gln Arg Leu Val Ala Leu Tyr Leu
305                 310                 315                 320

Ala Ala Arg Leu Ser Trp Asn Gln Val Asp Gln Val Ile Arg Asn Ala
                325                 330                 335

Leu Ala Ser Pro Gly Ser Gly Gly Asp Leu Gly Glu Ala Ile Arg Glu
```

```
            340                 345                 350

Gln Pro Glu Gln Ala Arg Leu Ala Leu Thr Leu Ala Ala Ala Glu Ser
        355                 360                 365

Glu Arg Phe Val Arg Gln Gly Thr Gly Asn Asp Glu Ala Gly Ala Ala
    370                 375                 380

Asn Ala Asp Val Val Ser Leu Thr Cys Pro Val Ala Ala Gly Glu Cys
385                 390                 395                 400

Ala Gly Pro Ala Asp Ser Gly Asp Ala Leu Leu Glu Arg Asn Tyr Pro
                405                 410                 415

Thr Gly Ala Glu Phe Leu Gly Asp Gly Gly Asp Val Ser Phe Ser Thr
            420                 425                 430

Arg Gly Thr Gln Asn Trp Thr Val Glu Arg Leu Leu Gln Ala Glu Phe
        435                 440                 445

Gln Ala Glu Pro Asp Gln Ala Glu Pro Asp Arg Ala Arg Ala His Tyr
    450                 455                 460

Asn Ile Arg Ala Arg Ala His Tyr Asn Leu Glu Ala His Tyr Asn Ile
465                 470                 475                 480

Val Ile Phe Arg Ala His Tyr Asn Ile Val Ile Phe Leu Glu His His
                485                 490                 495

His His His His
            500
```

<210> SEQ ID NO 33
<211> LENGTH: 504
<212> TYPE: PRT
<213> ORGANISM: Artificial sequence
<220> FEATURE:
<223> OTHER INFORMATION: chimeric antigen

<400> SEQUENCE: 33

```
Met Gly Ser Ser His His His His His His Ser Ser Gly Leu Val Pro
1               5                   10                  15

Arg Gly Ser His Met Ala Glu Glu Ala Phe Asp Leu Trp Asn Glu Cys
            20                  25                  30

Ala Lys Ala Cys Val Leu Asp Leu Lys Asp Gly Val Arg Ser Ser Arg
        35                  40                  45

Met Ser Val Asp Pro Ala Ile Ala Asp Thr Asn Gly Gln Gly Val Leu
    50                  55                  60

His Tyr Ser Met Val Leu Glu Gly Gly Asn Asp Ala Leu Lys Leu Ala
65                  70                  75                  80

Ile Asp Asn Ala Leu Ser Ile Thr Ser Asp Gly Leu Thr Ile Arg Leu
                85                  90                  95

Glu Gly Gly Val Glu Pro Asn Lys Pro Val Arg Tyr Ser Tyr Thr Arg
            100                 105                 110

Gln Ala Arg Gly Ser Trp Ser Leu Asn Trp Leu Val Pro Ile Gly His
        115                 120                 125

Glu Lys Pro Ser Asn Ile Lys Val Phe Ile His Glu Leu Asn Ala Gly
    130                 135                 140

Asn Gln Leu Ser His Met Ser Pro Ile Tyr Thr Ile Glu Met Gly Asp
145                 150                 155                 160

Glu Leu Leu Ala Lys Leu Ala Arg Asp Ala Thr Phe Phe Val Arg Ala
                165                 170                 175

His Glu Ser Asn Glu Met Gln Pro Thr Leu Ala Ile Ser His Ala Gly
            180                 185                 190

Val Ser Val Val Met Ala Gln Thr Gln Pro Arg Arg Glu Lys Arg Trp
```

```
        195                 200                 205

Ser Glu Trp Ala Ser Gly Lys Val Leu Cys Leu Leu Asp Pro Leu Asp
    210                 215                 220

Gly Val Tyr Asn Tyr Leu Ala Gln Gln Arg Cys Asn Leu Asp Asp Thr
225                 230                 235                 240

Trp Glu Gly Lys Ile Tyr Arg Val Leu Ala Gly Asn Pro Ala Lys His
                245                 250                 255

Asp Leu Asp Ile Lys Pro Thr Val Ile Ser His Arg Leu His Phe Pro
            260                 265                 270

Glu Gly Gly Ser Leu Ala Ala Leu Thr Ala His Gln Ala Cys His Leu
        275                 280                 285

Pro Leu Glu Thr Phe Thr Arg His Arg Gln Pro Arg Gly Trp Glu Gln
    290                 295                 300

Leu Glu Gln Cys Gly Tyr Pro Val Gln Arg Leu Val Ala Leu Tyr Leu
305                 310                 315                 320

Ala Ala Arg Leu Ser Trp Asn Gln Val Asp Gln Val Ile Arg Asn Ala
                325                 330                 335

Leu Ala Ser Pro Gly Ser Gly Gly Asp Leu Gly Glu Ala Ile Arg Glu
            340                 345                 350

Gln Pro Glu Gln Ala Arg Leu Ala Leu Thr Leu Ala Ala Ala Glu Ser
        355                 360                 365

Glu Arg Phe Val Arg Gln Gly Thr Gly Asn Asp Glu Ala Gly Ala Ala
    370                 375                 380

Asn Ala Asp Val Val Ser Leu Thr Cys Pro Val Ala Ala Gly Glu Cys
385                 390                 395                 400

Ala Gly Pro Ala Asp Ser Gly Asp Ala Leu Leu Glu Arg Asn Tyr Pro
                405                 410                 415

Thr Gly Ala Glu Phe Leu Gly Asp Gly Gly Asp Val Glu Phe Val Phe
            420                 425                 430

Leu Gln Lys Tyr Pro His Thr His Leu Val His Gln Ala Leu Asp Val
        435                 440                 445

Phe Leu Gln Lys Tyr Pro His Thr His Leu Val His Gln Ala Leu Asp
    450                 455                 460

Val Phe Leu Gln Lys Tyr Pro His Thr His Leu Val His Gln Ala Leu
465                 470                 475                 480

Asp Val Phe Leu Gln Lys Tyr Pro His Thr His Leu Val His Gln Ala
                485                 490                 495

Leu Glu His His His His His His
            500


<210> SEQ ID NO 34
<211> LENGTH: 711
<212> TYPE: PRT
<213> ORGANISM: Artificial sequence
<220> FEATURE:
<223> OTHER INFORMATION: chimeric antigen

<400> SEQUENCE: 34

Met Gly Ser Ser His His His His His His Ser Ser Gly Leu Val Pro
1               5                   10                  15

Arg Gly Ser His Met Ala Glu Glu Ala Phe Asp Leu Trp Asn Glu Cys
            20                  25                  30

Ala Lys Ala Cys Val Leu Asp Leu Lys Asp Gly Val Arg Ser Ser Arg
        35                  40                  45

Met Ser Val Asp Pro Ala Ile Ala Asp Thr Asn Gly Gln Gly Val Leu
```

-continued

```
    50                  55                  60

His Tyr Ser Met Val Leu Glu Gly Gly Asn Asp Ala Leu Lys Leu Ala
65                  70                  75                  80

Ile Asp Asn Ala Leu Ser Ile Thr Ser Asp Gly Leu Thr Ile Arg Leu
                85                  90                  95

Glu Gly Gly Val Glu Pro Asn Lys Pro Val Arg Tyr Ser Tyr Thr Arg
            100                 105                 110

Gln Ala Arg Gly Ser Trp Ser Leu Asn Trp Leu Val Pro Ile Gly His
        115                 120                 125

Glu Lys Pro Ser Asn Ile Lys Val Phe Ile His Glu Leu Asn Ala Gly
    130                 135                 140

Asn Gln Leu Ser His Met Ser Pro Ile Tyr Thr Ile Glu Met Gly Asp
145                 150                 155                 160

Glu Leu Leu Ala Lys Leu Ala Arg Asp Ala Thr Phe Phe Val Arg Ala
                165                 170                 175

His Glu Ser Asn Glu Met Gln Pro Thr Leu Ala Ile Ser His Ala Gly
            180                 185                 190

Val Ser Val Val Met Ala Gln Thr Gln Pro Arg Arg Glu Lys Arg Trp
        195                 200                 205

Ser Glu Trp Ala Ser Gly Lys Val Leu Cys Leu Leu Asp Pro Leu Asp
    210                 215                 220

Gly Val Tyr Asn Tyr Leu Ala Gln Gln Arg Cys Asn Leu Asp Asp Thr
225                 230                 235                 240

Trp Glu Gly Lys Ile Tyr Arg Val Leu Ala Gly Asn Pro Ala Lys His
                245                 250                 255

Asp Leu Asp Ile Lys Pro Thr Val Ile Ser His Arg Leu His Phe Pro
            260                 265                 270

Glu Gly Gly Ser Leu Ala Ala Leu Thr Ala His Gln Ala Cys His Leu
        275                 280                 285

Pro Leu Glu Thr Phe Thr Arg His Arg Gln Pro Arg Gly Trp Glu Gln
    290                 295                 300

Leu Glu Gln Cys Gly Tyr Pro Val Gln Arg Leu Val Ala Leu Tyr Leu
305                 310                 315                 320

Ala Ala Arg Leu Ser Trp Asn Gln Val Asp Gln Val Ile Arg Asn Ala
                325                 330                 335

Leu Ala Ser Pro Gly Ser Gly Gly Asp Leu Gly Glu Ala Ile Arg Glu
            340                 345                 350

Gln Pro Glu Gln Ala Arg Leu Ala Leu Thr Leu Ala Ala Ala Glu Ser
        355                 360                 365

Glu Arg Phe Val Arg Gln Gly Thr Gly Asn Asp Glu Ala Gly Ala Ala
    370                 375                 380

Asn Ala Asp Val Val Ser Leu Thr Cys Pro Val Ala Ala Gly Glu Cys
385                 390                 395                 400

Ala Gly Pro Ala Asp Ser Gly Asp Ala Leu Leu Glu Arg Asn Tyr Pro
                405                 410                 415

Thr Gly Ala Glu Phe Leu Gly Asp Gly Gly Asp Val Glu Phe Leu Leu
            420                 425                 430

Glu Pro His Thr His Leu Val His Gln Ala Asn Val Leu Leu Ala Leu
        435                 440                 445

Gln Leu Leu Leu Glu Asp Arg Glu Phe Val Phe Leu Gln Lys Tyr Pro
    450                 455                 460

His Val Glu Pro His Thr His Leu Val His Gln Ala Asn Val Leu Leu
465                 470                 475                 480
```

Ala Leu Gln Leu Leu Leu Glu Asp Arg Glu Phe Val Phe Leu Gln Lys
485 490 495

Tyr Pro His Val Glu Pro His Thr His Leu Val His Gln Ala Asn Val
500 505 510

Leu Leu Ala Leu Gln Leu Leu Leu Glu Asp Arg Glu Phe Val Phe Leu
515 520 525

Gln Lys Tyr Pro His Val Glu Pro His Thr His Leu Val His Gln Ala
530 535 540

Asn Val Leu Leu Ala Leu Gln Leu Leu Leu Glu Asp Arg Glu Phe Val
545 550 555 560

Phe Leu Gln Lys Tyr Pro His Val Glu Pro His Thr His Leu Val His
565 570 575

Gln Ala Asn Val Leu Leu Ala Leu Gln Leu Leu Leu Glu Asp Arg Glu
580 585 590

Phe Val Phe Leu Gln Lys Tyr Pro His Val Glu Pro His Thr His Leu
595 600 605

Val His Gln Ala Asn Val Leu Leu Ala Leu Gln Leu Leu Leu Glu Asp
610 615 620

Arg Glu Phe Val Phe Leu Gln Lys Tyr Pro His Val Glu Pro His Thr
625 630 635 640

His Leu Val His Gln Ala Asn Val Leu Leu Ala Leu Gln Leu Leu Leu
645 650 655

Glu Asp Arg Glu Phe Val Phe Leu Gln Lys Tyr Pro His Val Glu Pro
660 665 670

His Thr His Leu Val His Gln Ala Asn Val Leu Leu Ala Leu Gln Leu
675 680 685

Leu Leu Glu Asp Arg Glu Phe Val Phe Leu Gln Lys Tyr Pro His Val
690 695 700

Glu His His His His His His
705 710

<210> SEQ ID NO 35
<211> LENGTH: 749
<212> TYPE: PRT
<213> ORGANISM: Artificial sequence
<220> FEATURE:
<223> OTHER INFORMATION: chimeric antigen

<400> SEQUENCE: 35

Met Gly Ser Ser His His His His His His Ser Ser Gly Leu Val Pro
1 5 10 15

Arg Gly Ser His Met Ala Glu Glu Ala Phe Asp Leu Trp Asn Glu Cys
20 25 30

Ala Lys Ala Cys Val Leu Asp Leu Lys Asp Gly Val Arg Ser Ser Arg
35 40 45

Met Ser Val Asp Pro Ala Ile Ala Asp Thr Asn Gly Gln Gly Val Leu
50 55 60

His Tyr Ser Met Val Leu Glu Gly Gly Asn Asp Ala Leu Lys Leu Ala
65 70 75 80

Ile Asp Asn Ala Leu Ser Ile Thr Ser Asp Gly Leu Thr Ile Arg Leu
85 90 95

Glu Gly Gly Val Glu Pro Asn Lys Pro Val Arg Tyr Ser Tyr Thr Arg
100 105 110

Gln Ala Arg Gly Ser Trp Ser Leu Asn Trp Leu Val Pro Ile Gly His
115 120 125

-continued

```
Glu Lys Pro Ser Asn Ile Lys Val Phe Ile His Glu Leu Asn Ala Gly
    130                 135                 140

Asn Gln Leu Ser His Met Ser Pro Ile Tyr Thr Ile Glu Met Gly Asp
145                 150                 155                 160

Glu Leu Leu Ala Lys Leu Ala Arg Asp Ala Thr Phe Phe Val Arg Ala
                165                 170                 175

His Glu Ser Asn Glu Met Gln Pro Thr Leu Ala Ile Ser His Ala Gly
            180                 185                 190

Val Ser Val Val Met Ala Gln Thr Gln Pro Arg Arg Glu Lys Arg Trp
        195                 200                 205

Ser Glu Trp Ala Ser Gly Lys Val Leu Cys Leu Leu Asp Pro Leu Asp
    210                 215                 220

Gly Val Tyr Asn Tyr Leu Ala Gln Gln Arg Cys Asn Leu Asp Asp Thr
225                 230                 235                 240

Trp Glu Gly Lys Ile Tyr Arg Val Leu Ala Gly Asn Pro Ala Lys His
                245                 250                 255

Asp Leu Asp Ile Lys Pro Thr Val Ile Ser His Arg Leu His Phe Pro
            260                 265                 270

Glu Gly Gly Ser Leu Ala Ala Leu Thr Ala His Gln Ala Cys His Leu
        275                 280                 285

Pro Leu Glu Thr Phe Thr Arg His Arg Gln Pro Arg Gly Trp Glu Gln
    290                 295                 300

Leu Glu Gln Cys Gly Tyr Pro Val Gln Arg Leu Val Ala Leu Tyr Leu
305                 310                 315                 320

Ala Ala Arg Leu Ser Trp Asn Gln Val Asp Gln Val Ile Arg Asn Ala
                325                 330                 335

Leu Ala Ser Pro Gly Ser Gly Gly Asp Leu Gly Glu Ala Ile Arg Glu
            340                 345                 350

Gln Pro Glu Gln Ala Arg Leu Ala Leu Thr Leu Ala Ala Ala Glu Ser
        355                 360                 365

Glu Arg Phe Val Arg Gln Gly Thr Gly Asn Asp Glu Ala Gly Ala Ala
    370                 375                 380

Asn Ala Asp Val Val Ser Leu Thr Cys Pro Val Ala Ala Gly Glu Cys
385                 390                 395                 400

Ala Gly Pro Ala Asp Ser Gly Asp Ala Leu Leu Glu Arg Asn Tyr Pro
                405                 410                 415

Thr Gly Ala Glu Phe Leu Gly Asp Gly Gly Asp Val Ser Phe Ser Thr
            420                 425                 430

Arg Gly Thr Gln Asn Trp Thr Val Glu Arg Leu Leu Gln Ala Glu Phe
        435                 440                 445

Val Ser Phe Ser Thr Gly Gly Ser Gln Asn Trp Thr Val Glu Arg Leu
    450                 455                 460

Leu Gln Ala Glu Phe Cys Ser Thr Ser Gln Ala Ala Arg Gln Arg Leu
465                 470                 475                 480

Glu Thr Gly Arg Asn Cys Ser Thr Gly Gln Ala Ala Arg Gln Arg Leu
                485                 490                 495

Glu Pro Gly Arg Asn Leu Val Leu Cys Leu Thr Ser Gln Ala Ala Gln
            500                 505                 510

Gln Arg Leu Glu Pro Gly Gly Asn Cys Gln Thr Ser Gln Ala Ala His
        515                 520                 525

Gln Arg Leu Glu Pro Gly Arg Asn Cys Arg Thr Ser Gln Ala Ala Ser
    530                 535                 540
```

```
Gln Arg Leu Glu Pro Gly Arg Asn Cys Arg Thr Ser Gln Ala Ala His
545                 550                 555                 560

Gln Arg Leu Glu Pro Gly Arg Asn Cys Ser Thr Arg Gln Ala Ala Gln
                565                 570                 575

Gln Arg Leu Glu Pro Gly Arg Asn Leu Leu Cys Pro Thr Ser Gln Ala
            580                 585                 590

Ala His Gln Arg Arg Leu Glu Pro Gly Arg Asn Cys Ser Thr Ser Gln
        595                 600                 605

Ala Ala Tyr Gln Arg Leu Glu Pro Gly Arg Asn Cys Pro Thr Ser Arg
    610                 615                 620

Ala Ala Arg Gln Arg Leu Glu Pro Gly Arg Asn Leu Leu Cys Ser Thr
625                 630                 635                 640

Ser Gln Ala Ala Leu Gln Arg Leu Glu Pro Gly Arg Asn Leu Cys Pro
                645                 650                 655

Thr Ser Gln Ala Ala Lys Gln Arg Leu Glu Pro Gly Arg Asn Leu Val
            660                 665                 670

Val Cys Leu Thr Ser Gln Ala Ala Arg Gln Arg Leu Glu Pro Gly Arg
        675                 680                 685

Asn Cys Ser Thr Ser Gln Ala Ala Ser Gln Arg Leu Glu Pro Gly Arg
    690                 695                 700

Asn Cys Pro Thr Ser Gln Ala Ala Arg Gln Arg Leu Glu Pro Gly Arg
705                 710                 715                 720

Asn Val Leu Leu Leu Cys Leu Thr Ser Gln Ala Ala His Gln Arg Leu
                725                 730                 735

Glu Pro Gly Arg Asn Leu Glu His His His His His His
            740                 745


<210> SEQ ID NO 36
<211> LENGTH: 682
<212> TYPE: PRT
<213> ORGANISM: Artificial sequence
<220> FEATURE:
<223> OTHER INFORMATION: chimeric antigen

<400> SEQUENCE: 36

Met Gly Ser Ser His His His His His His Ser Ser Gly Leu Val Pro
1               5                   10                  15

Arg Gly Ser His Met Ala Glu Glu Ala Phe Asp Leu Trp Asn Glu Cys
            20                  25                  30

Ala Lys Ala Cys Val Leu Asp Leu Lys Asp Gly Val Arg Ser Ser Arg
        35                  40                  45

Met Ser Val Asp Pro Ala Ile Ala Asp Thr Asn Gly Gln Gly Val Leu
    50                  55                  60

His Tyr Ser Met Val Leu Glu Gly Gly Asn Asp Ala Leu Lys Leu Ala
65                  70                  75                  80

Ile Asp Asn Ala Leu Ser Ile Thr Ser Asp Gly Leu Thr Ile Arg Leu
                85                  90                  95

Glu Gly Gly Val Glu Pro Asn Lys Pro Val Arg Tyr Ser Tyr Thr Arg
            100                 105                 110

Gln Ala Arg Gly Ser Trp Ser Leu Asn Trp Leu Val Pro Ile Gly His
        115                 120                 125

Glu Lys Pro Ser Asn Ile Lys Val Phe Ile His Glu Leu Asn Ala Gly
    130                 135                 140

Asn Gln Leu Ser His Met Ser Pro Ile Tyr Thr Ile Glu Met Gly Asp
145                 150                 155                 160
```

-continued

```
Glu Leu Leu Ala Lys Leu Ala Arg Asp Ala Thr Phe Phe Val Arg Ala
                165                 170                 175

His Glu Ser Asn Glu Met Gln Pro Thr Leu Ala Ile Ser His Ala Gly
            180                 185                 190

Val Ser Val Val Met Ala Gln Thr Gln Pro Arg Arg Glu Lys Arg Trp
        195                 200                 205

Ser Glu Trp Ala Ser Gly Lys Val Leu Cys Leu Leu Asp Pro Leu Asp
    210                 215                 220

Gly Val Tyr Asn Tyr Leu Ala Gln Gln Arg Cys Asn Leu Asp Asp Thr
225                 230                 235                 240

Trp Glu Gly Lys Ile Tyr Arg Val Leu Ala Gly Asn Pro Ala Lys His
                245                 250                 255

Asp Leu Asp Ile Lys Pro Thr Val Ile Ser His Arg Leu His Phe Pro
            260                 265                 270

Glu Gly Gly Ser Leu Ala Ala Leu Thr Ala His Gln Ala Cys His Leu
        275                 280                 285

Pro Leu Glu Thr Phe Thr Arg His Arg Gln Pro Arg Gly Trp Glu Gln
    290                 295                 300

Leu Glu Gln Cys Gly Tyr Pro Val Gln Arg Leu Val Ala Leu Tyr Leu
305                 310                 315                 320

Ala Ala Arg Leu Ser Trp Asn Gln Val Asp Gln Val Ile Arg Asn Ala
                325                 330                 335

Leu Ala Ser Pro Gly Ser Gly Gly Asp Leu Gly Glu Ala Ile Arg Glu
            340                 345                 350

Gln Pro Glu Gln Ala Arg Leu Ala Leu Thr Leu Ala Ala Ala Glu Ser
        355                 360                 365

Glu Arg Phe Val Arg Gln Gly Thr Gly Asn Asp Glu Ala Gly Ala Ala
    370                 375                 380

Asn Ala Asp Val Val Ser Leu Thr Cys Pro Val Ala Ala Gly Glu Cys
385                 390                 395                 400

Ala Gly Pro Ala Asp Ser Gly Asp Ala Leu Leu Glu Arg Asn Tyr Pro
                405                 410                 415

Thr Gly Ala Glu Phe Leu Gly Asp Gly Gly Asp Val Ser Phe Ser Thr
            420                 425                 430

Arg Gly Thr Gln Asn Trp Thr Val Glu Arg Leu Leu Gln Ala Glu Phe
        435                 440                 445

Gly Val Ser Ala Ala Gln Glu Lys Ile Ser Phe Gly Leu Leu Gly Val
    450                 455                 460

Pro Thr Ala Gln Glu Thr Thr Ser Ile Arg Glu Val Leu Glu Val Ser
465                 470                 475                 480

Thr Ala Gln Glu Asn Ser Pro Phe Met Leu Gly Ala Ser Ala Thr Glu
                485                 490                 495

Glu Lys Thr Ser Leu Arg Leu Gly Ala Ser Thr Thr Gln Glu Thr Ser
            500                 505                 510

Phe Gly Lys Cys Leu Arg Pro His Gly Val Ser Ala Ala Gln Gly Thr
        515                 520                 525

Thr Pro Phe Arg Gly Val Ser Thr Thr Gln Glu Asn Thr Ser Phe Gly
    530                 535                 540

Arg Val Pro Thr Ala Gln Glu Asn Val Ser Phe Gly Leu His Gly Val
545                 550                 555                 560

Pro Ala Ala Gln Lys Thr Asn Ser Phe Gly Gly Val Pro Thr Ala Gln
                565                 570                 575

Glu Asn Ile Ser Phe Lys Glu Val Ser Ala Thr Gln Arg Glu Ile Pro
```

```
            580                 585                 590

Phe Arg Cys Leu Arg Pro His Gly Val Ser Thr Ala Gln Glu Thr Pro
        595                 600                 605

Phe Arg Gly Val Ser Thr Ala Gln Glu Thr Ile Pro Phe Arg Gly Val
    610                 615                 620

Ser Ala Thr His Glu Asn Ile Ser Phe Gly Cys Leu Arg Pro His Gly
625                 630                 635                 640

Val Ser Ala Ala Gln Glu Ser Ile Pro Ile Arg Leu Gly Ala Ser Ala
                645                 650                 655

Ala Gln Glu Asn Thr Ser Phe Arg Gly Thr Pro Ala Ala Gln Glu Lys
            660                 665                 670

Ile Pro Leu Glu His His His His His His
        675                 680


<210> SEQ ID NO 37
<211> LENGTH: 741
<212> TYPE: PRT
<213> ORGANISM: Artificial sequence
<220> FEATURE:
<223> OTHER INFORMATION: chimeric antigen

<400> SEQUENCE: 37

Met Gly Ser Ser His His His His His His Ser Ser Gly Leu Val Pro
1               5                   10                  15

Arg Gly Ser His Met Ala Glu Glu Ala Phe Asp Leu Trp Asn Glu Cys
            20                  25                  30

Ala Lys Ala Cys Val Leu Asp Leu Lys Asp Gly Val Arg Ser Ser Arg
        35                  40                  45

Met Ser Val Asp Pro Ala Ile Ala Asp Thr Asn Gly Gln Gly Val Leu
    50                  55                  60

His Tyr Ser Met Val Leu Glu Gly Gly Asn Asp Ala Leu Lys Leu Ala
65                  70                  75                  80

Ile Asp Asn Ala Leu Ser Ile Thr Ser Asp Gly Leu Thr Ile Arg Leu
                85                  90                  95

Glu Gly Gly Val Glu Pro Asn Lys Pro Val Arg Tyr Ser Tyr Thr Arg
            100                 105                 110

Gln Ala Arg Gly Ser Trp Ser Leu Asn Trp Leu Val Pro Ile Gly His
        115                 120                 125

Glu Lys Pro Ser Asn Ile Lys Val Phe Ile His Glu Leu Asn Ala Gly
    130                 135                 140

Asn Gln Leu Ser His Met Ser Pro Ile Tyr Thr Ile Glu Met Gly Asp
145                 150                 155                 160

Glu Leu Leu Ala Lys Leu Ala Arg Asp Ala Thr Phe Phe Val Arg Ala
                165                 170                 175

His Glu Ser Asn Glu Met Gln Pro Thr Leu Ala Ile Ser His Ala Gly
            180                 185                 190

Val Ser Val Val Met Ala Gln Thr Gln Pro Arg Arg Glu Lys Arg Trp
        195                 200                 205

Ser Glu Trp Ala Ser Gly Lys Val Leu Cys Leu Leu Asp Pro Leu Asp
    210                 215                 220

Gly Val Tyr Asn Tyr Leu Ala Gln Gln Arg Cys Asn Leu Asp Asp Thr
225                 230                 235                 240

Trp Glu Gly Lys Ile Tyr Arg Val Leu Ala Gly Asn Pro Ala Lys His
                245                 250                 255

Asp Leu Asp Ile Lys Pro Thr Val Ile Ser His Arg Leu His Phe Pro
```

```
            260                 265                 270

Glu Gly Gly Ser Leu Ala Ala Leu Thr Ala His Gln Ala Cys His Leu
        275                 280                 285

Pro Leu Glu Thr Phe Thr Arg His Arg Gln Pro Arg Gly Trp Glu Gln
    290                 295                 300

Leu Glu Gln Cys Gly Tyr Pro Val Gln Arg Leu Val Ala Leu Tyr Leu
305                 310                 315                 320

Ala Ala Arg Leu Ser Trp Asn Gln Val Asp Gln Val Ile Arg Asn Ala
                325                 330                 335

Leu Ala Ser Pro Gly Ser Gly Gly Asp Leu Gly Glu Ala Ile Arg Glu
            340                 345                 350

Gln Pro Glu Gln Ala Arg Leu Ala Leu Thr Leu Ala Ala Ala Glu Ser
        355                 360                 365

Glu Arg Phe Val Arg Gln Gly Thr Gly Asn Asp Glu Ala Gly Ala Ala
    370                 375                 380

Asn Ala Asp Val Val Ser Leu Thr Cys Pro Val Ala Ala Gly Glu Cys
385                 390                 395                 400

Ala Gly Pro Ala Asp Ser Gly Asp Ala Leu Leu Glu Arg Asn Tyr Pro
                405                 410                 415

Thr Gly Ala Glu Phe Leu Gly Asp Gly Gly Asp Val Ser Phe Ser Thr
            420                 425                 430

Arg Gly Thr Gln Asn Trp Thr Val Glu Arg Leu Leu Gln Ala Glu Phe
        435                 440                 445

Leu Gly Val Ser Ala Ala Gln Glu Arg Ile Pro Ile Arg Glu Val Ser
    450                 455                 460

Ala Asp Lys Glu Val Ser Ala Glu Lys Lys Glu Ile Ser Phe Gly Val
465                 470                 475                 480

Ser Thr Ala Gln Gly Asn Ile Ser Phe Gly Leu Gly Val Ser Thr Ala
                485                 490                 495

Gln Glu Ala Ile Pro Phe Leu Ala Leu Gly Val Ser Thr Ala Gln Glu
            500                 505                 510

Thr Ile Pro Phe Gly Leu Leu Gly Val Ser Thr Ala Gln Gly Ile Ile
        515                 520                 525

Ser Phe Gly Gly Val Ser Thr Ala Gln Glu Asn Ile Ser Phe Gly Gly
    530                 535                 540

Val Ser Thr Ala Gln Glu Thr Ile Ser Phe Gly Leu Leu Gly Val Ser
545                 550                 555                 560

Thr Ala Gln Glu Asn Ile Ser Phe Gly Cys Leu Arg Thr His Glu Val
                565                 570                 575

Ser Ala Ala Gln Glu Lys Ile Ser Phe Gly Gly Val Ser Glu Ala Gln
            580                 585                 590

Lys Ile Ser Phe Gly Val Ser Ala Ala Gly Val Ser Ala Ala Gln Glu
        595                 600                 605

Glu Ile Pro Phe Gly Cys Leu Arg Pro His Gly Leu Pro Ala Ala Gln
    610                 615                 620

Glu Lys Thr Ser Phe Gly Gly Val Ser Ala Ala Gln Glu Lys Thr Ser
625                 630                 635                 640

Phe Gly Gly Val Ser Ala Ala Gln Glu Glu Phe Ser Phe Gly Cys Leu
                645                 650                 655

Arg Pro His Arg Val Ser Ala Ala Gln Glu Lys Ile Ser Phe Glu Val
            660                 665                 670

Ser Ala Leu Glu Val Ser Ala Ala Gln Glu Lys Ile Ser Phe Gly Val
        675                 680                 685
```

Ser Ala Ala Leu Gly Val Ser Ala Ala Gln Glu Lys Asn Ser Phe Gly
690 695 700

Cys Leu Arg Pro His Gly Val Ser Ala Ala Gln Glu Lys Thr Ser Phe
705 710 715 720

Gly Gly Val Ser Ala Ala Gln Lys Lys Ile Ser Phe Gly Leu Glu His
725 730 735

His His His His His
740

<210> SEQ ID NO 38
<211> LENGTH: 595
<212> TYPE: PRT
<213> ORGANISM: Artificial sequence
<220> FEATURE:
<223> OTHER INFORMATION: fusion biogenic polypeptide

<400> SEQUENCE: 38

Met Ala Glu Gln Leu Val Asp Leu Trp Asn Glu Cys Ala Lys Ala Cys
1 5 10 15

Val Leu Asp Leu Lys Asp Gly Val Arg Ser Ser Arg Met Ser Val Asp
20 25 30

Pro Ala Ile Ala Asp Thr Asn Gly Gln Gly Val Leu His Tyr Cys Met
35 40 45

Glu Phe Ser Phe His Gln Leu Pro Ala Arg Ser Pro Ala Pro Leu Gln
50 55 60

Leu Glu His Met Ala Glu Glu Ala Phe Asp Leu Trp Asn Glu Cys Ala
65 70 75 80

Lys Ala Cys Val Leu Asp Leu Lys Asp Gly Val Arg Ser Ser Arg Met
85 90 95

Ser Val Asp Pro Ala Ile Ala Asp Thr Asn Gly Gln Gly Val Leu His
100 105 110

Tyr Ser Met Val Leu Glu Gly Gly Asn Asp Ala Leu Lys Leu Ala Ile
115 120 125

Asp Asn Ala Leu Ser Ile Thr Ser Asp Gly Leu Thr Ile Arg Leu Glu
130 135 140

Gly Gly Val Glu Pro Asn Lys Pro Val Arg Tyr Ser Tyr Thr Arg Gln
145 150 155 160

Ala Arg Gly Ser Trp Ser Leu Asn Trp Leu Val Pro Ile Gly His Glu
165 170 175

Lys Pro Ser Asn Ile Lys Val Phe Ile His Glu Leu Asn Ala Gly Asn
180 185 190

Gln Leu Ser His Met Ser Pro Ile Tyr Thr Ile Glu Met Gly Asp Glu
195 200 205

Leu Leu Ala Lys Leu Ala Arg Asp Ala Thr Phe Phe Val Arg Ala His
210 215 220

Glu Ser Asn Glu Met Gln Pro Thr Leu Ala Ile Ser His Ala Gly Val
225 230 235 240

Ser Val Val Met Ala Gln Thr Gln Pro Arg Arg Glu Lys Arg Trp Ser
245 250 255

Glu Trp Ala Ser Gly Lys Val Leu Cys Leu Leu Asp Pro Leu Asp Gly
260 265 270

Val Tyr Asn Tyr Leu Ala Gln Gln Arg Cys Asn Leu Asp Asp Thr Trp
275 280 285

Glu Gly Lys Ile Tyr Arg Val Leu Ala Gly Asn Pro Ala Lys His Asp
290 295 300

Leu Asp Ile Lys Pro Thr Val Ile Ser His Arg Leu His Phe Pro Glu
305 310 315 320

Gly Gly Ser Leu Ala Ala Leu Thr Ala His Gln Ala Cys His Leu Pro
325 330 335

Leu Glu Thr Phe Thr Arg His Arg Gln Pro Arg Gly Trp Glu Gln Leu
340 345 350

Glu Gln Cys Gly Tyr Pro Val Gln Arg Leu Val Ala Leu Tyr Leu Ala
355 360 365

Ala Arg Leu Ser Trp Asn Gln Val Asp Gln Val Ile Arg Asn Ala Leu
370 375 380

Ala Ser Pro Gly Ser Gly Gly Asp Leu Gly Glu Ala Ile Arg Glu Gln
385 390 395 400

Pro Glu Gln Ala Arg Leu Ala Leu Thr Leu Ala Ala Ala Glu Ser Glu
405 410 415

Arg Phe Val Arg Gln Gly Thr Gly Asn Asp Glu Ala Gly Ala Ala Asn
420 425 430

Ala Asp Val Val Ser Leu Thr Cys Pro Val Ala Ala Gly Glu Cys Ala
435 440 445

Gly Pro Ala Asp Ser Gly Asp Ala Leu Leu Glu Arg Asn Tyr Pro Thr
450 455 460

Gly Ala Glu Phe Leu Gly Asp Gly Gly Asp Val Ser Phe Ser Thr Arg
465 470 475 480

Gly Thr Gln Asn Trp Thr Val Glu Arg Leu Leu Gln Ala Glu Phe Val
485 490 495

Asp Lys Asp Glu Leu Arg Glu Val Tyr Asn Phe Ala Phe Leu Leu Val
500 505 510

Leu Arg Arg Glu Val Tyr Asp Lys Asp Glu Leu Leu Leu Leu Leu Glu
515 520 525

Asp Arg Gln Leu Leu Arg Arg Glu Val Phe Cys Gly Phe Arg Asp Leu
530 535 540

Leu Glu Asp Arg Val Tyr Asp Phe Ala Phe Ser Asp Leu Lys Leu Pro
545 550 555 560

Gln Leu Cys Thr Glu Leu Lys Leu Pro Gln Leu Cys Thr Glu Leu Lys
565 570 575

Asp Glu Leu Lys Asp Glu Leu Val Leu Leu Leu Leu Glu His His His
580 585 590

His His His
595

<210> SEQ ID NO 39
<211> LENGTH: 603
<212> TYPE: PRT
<213> ORGANISM: Artificial sequence
<220> FEATURE:
<223> OTHER INFORMATION: fusion biogenic polypeptide

<400> SEQUENCE: 39

Met Ala Glu Gln Leu Val Asp Leu Trp Asn Glu Cys Ala Lys Ala Cys
1 5 10 15

Val Leu Asp Leu Lys Asp Gly Val Arg Ser Ser Arg Met Ser Val Asp
20 25 30

Pro Ala Ile Ala Asp Thr Asn Gly Gln Gly Val Leu His Tyr Cys Met
35 40 45

Glu Phe Ser Ser Phe His Leu Phe His His Leu Pro Ala Arg Ala Pro
50 55 60

-continued

```
Leu Ala Pro Ser Glu Leu Gln Pro Leu Glu His Met Ala Glu Glu Ala
65                  70                  75                  80

Phe Asp Leu Trp Asn Glu Cys Ala Lys Ala Cys Val Leu Asp Leu Lys
                85                  90                  95

Asp Gly Val Arg Ser Ser Arg Met Ser Val Asp Pro Ala Ile Ala Asp
            100                 105                 110

Thr Asn Gly Gln Gly Val Leu His Tyr Ser Met Val Leu Glu Gly Gly
        115                 120                 125

Asn Asp Ala Leu Lys Leu Ala Ile Asp Asn Ala Leu Ser Ile Thr Ser
    130                 135                 140

Asp Gly Leu Thr Ile Arg Leu Glu Gly Gly Val Glu Pro Asn Lys Pro
145                 150                 155                 160

Val Arg Tyr Ser Tyr Thr Arg Gln Ala Arg Gly Ser Trp Ser Leu Asn
                165                 170                 175

Trp Leu Val Pro Ile Gly His Glu Lys Pro Ser Asn Ile Lys Val Phe
            180                 185                 190

Ile His Glu Leu Asn Ala Gly Asn Gln Leu Ser His Met Ser Pro Ile
        195                 200                 205

Tyr Thr Ile Glu Met Gly Asp Glu Leu Leu Ala Lys Leu Ala Arg Asp
    210                 215                 220

Ala Thr Phe Phe Val Arg Ala His Glu Ser Asn Glu Met Gln Pro Thr
225                 230                 235                 240

Leu Ala Ile Ser His Ala Gly Val Ser Val Val Met Ala Gln Thr Gln
                245                 250                 255

Pro Arg Arg Glu Lys Arg Trp Ser Glu Trp Ala Ser Gly Lys Val Leu
            260                 265                 270

Cys Leu Leu Asp Pro Leu Asp Gly Val Tyr Asn Tyr Leu Ala Gln Gln
        275                 280                 285

Arg Cys Asn Leu Asp Asp Thr Trp Glu Gly Lys Ile Tyr Arg Val Leu
    290                 295                 300

Ala Gly Asn Pro Ala Lys His Asp Leu Asp Ile Lys Pro Thr Val Ile
305                 310                 315                 320

Ser His Arg Leu His Phe Pro Glu Gly Gly Ser Leu Ala Ala Leu Thr
                325                 330                 335

Ala His Gln Ala Cys His Leu Pro Leu Glu Thr Phe Thr Arg His Arg
            340                 345                 350

Gln Pro Arg Gly Trp Glu Gln Leu Glu Gln Cys Gly Tyr Pro Val Gln
        355                 360                 365

Arg Leu Val Ala Leu Tyr Leu Ala Ala Arg Leu Ser Trp Asn Gln Val
    370                 375                 380

Asp Gln Val Ile Arg Asn Ala Leu Ala Ser Pro Gly Ser Gly Gly Asp
385                 390                 395                 400

Leu Gly Glu Ala Ile Arg Glu Gln Pro Glu Gln Ala Arg Leu Ala Leu
                405                 410                 415

Thr Leu Ala Ala Ala Glu Ser Glu Arg Phe Val Arg Gln Gly Thr Gly
            420                 425                 430

Asn Asp Glu Ala Gly Ala Ala Asn Ala Asp Val Val Ser Leu Thr Cys
        435                 440                 445

Pro Val Ala Ala Gly Glu Cys Ala Gly Pro Ala Asp Ser Gly Asp Ala
    450                 455                 460

Leu Leu Glu Arg Asn Tyr Pro Thr Gly Ala Glu Phe Leu Gly Asp Gly
465                 470                 475                 480
```

Gly Asp Val Ser Phe Ser Thr Arg Gly Thr Gln Asn Trp Thr Val Glu
485 490 495

Arg Leu Leu Gln Ala Glu Phe Val Asp Lys Asp Glu Leu Arg Glu Val
500 505 510

Tyr Asn Phe Ala Phe Leu Leu Val Leu Arg Arg Glu Val Tyr Asp Lys
515 520 525

Asp Glu Leu Leu Leu Leu Leu Glu Asp Arg Gln Leu Leu Arg Arg Glu
530 535 540

Val Phe Cys Gly Phe Arg Asp Leu Leu Glu Asp Arg Val Tyr Asp Phe
545 550 555 560

Ala Phe Ser Asp Leu Lys Leu Pro Gln Leu Cys Thr Glu Leu Lys Leu
565 570 575

Pro Gln Leu Cys Thr Glu Leu Lys Asp Glu Leu Lys Asp Glu Leu Val
580 585 590

Leu Leu Leu Leu Glu His His His His His His
595 600

<210> SEQ ID NO 40
<211> LENGTH: 598
<212> TYPE: PRT
<213> ORGANISM: Artificial sequence
<220> FEATURE:
<223> OTHER INFORMATION: fusion biogenic polypeptide

<400> SEQUENCE: 40

Met Ala Glu Gln Leu Val Asp Leu Trp Asn Glu Cys Ala Lys Ala Cys
1 5 10 15

Val Leu Asp Leu Lys Asp Gly Val Arg Ser Ser Arg Met Ser Val Asp
20 25 30

Pro Ala Ile Ala Asp Thr Asn Gly Gln Gly Val Leu His Tyr Cys Met
35 40 45

Glu Phe Ser Thr Pro Phe His Pro Leu Pro Ala Arg Lys Pro Leu Pro
50 55 60

Leu Val Pro Leu Glu His Met Ala Glu Glu Ala Phe Asp Leu Trp Asn
65 70 75 80

Glu Cys Ala Lys Ala Cys Val Leu Asp Leu Lys Asp Gly Val Arg Ser
85 90 95

Ser Arg Met Ser Val Asp Pro Ala Ile Ala Asp Thr Asn Gly Gln Gly
100 105 110

Val Leu His Tyr Ser Met Val Leu Glu Gly Gly Asn Asp Ala Leu Lys
115 120 125

Leu Ala Ile Asp Asn Ala Leu Ser Ile Thr Ser Asp Gly Leu Thr Ile
130 135 140

Arg Leu Glu Gly Gly Val Glu Pro Asn Lys Pro Val Arg Tyr Ser Tyr
145 150 155 160

Thr Arg Gln Ala Arg Gly Ser Trp Ser Leu Asn Trp Leu Val Pro Ile
165 170 175

Gly His Glu Lys Pro Ser Asn Ile Lys Val Phe Ile His Glu Leu Asn
180 185 190

Ala Gly Asn Gln Leu Ser His Met Ser Pro Ile Tyr Thr Ile Glu Met
195 200 205

Gly Asp Glu Leu Leu Ala Lys Leu Ala Arg Asp Ala Thr Phe Phe Val
210 215 220

Arg Ala His Glu Ser Asn Glu Met Gln Pro Thr Leu Ala Ile Ser His
225 230 235 240

Ala Gly Val Ser Val Val Met Ala Gln Thr Gln Pro Arg Arg Glu Lys
245 250 255

Arg Trp Ser Glu Trp Ala Ser Gly Lys Val Leu Cys Leu Leu Asp Pro
260 265 270

Leu Asp Gly Val Tyr Asn Tyr Leu Ala Gln Gln Arg Cys Asn Leu Asp
275 280 285

Asp Thr Trp Glu Gly Lys Ile Tyr Arg Val Leu Ala Gly Asn Pro Ala
290 295 300

Lys His Asp Leu Asp Ile Lys Pro Thr Val Ile Ser His Arg Leu His
305 310 315 320

Phe Pro Glu Gly Gly Ser Leu Ala Ala Leu Thr Ala His Gln Ala Cys
325 330 335

His Leu Pro Leu Glu Thr Phe Thr Arg His Arg Gln Pro Arg Gly Trp
340 345 350

Glu Gln Leu Glu Gln Cys Gly Tyr Pro Val Gln Arg Leu Val Ala Leu
355 360 365

Tyr Leu Ala Ala Arg Leu Ser Trp Asn Gln Val Asp Gln Val Ile Arg
370 375 380

Asn Ala Leu Ala Ser Pro Gly Ser Gly Gly Asp Leu Gly Glu Ala Ile
385 390 395 400

Arg Glu Gln Pro Glu Gln Ala Arg Leu Ala Leu Thr Leu Ala Ala Ala
405 410 415

Glu Ser Glu Arg Phe Val Arg Gln Gly Thr Gly Asn Asp Glu Ala Gly
420 425 430

Ala Ala Asn Ala Asp Val Val Ser Leu Thr Cys Pro Val Ala Ala Gly
435 440 445

Glu Cys Ala Gly Pro Ala Asp Ser Gly Asp Ala Leu Leu Glu Arg Asn
450 455 460

Tyr Pro Thr Gly Ala Glu Phe Leu Gly Asp Gly Gly Asp Val Ser Phe
465 470 475 480

Ser Thr Arg Gly Thr Gln Asn Trp Thr Val Glu Arg Leu Leu Gln Ala
485 490 495

Glu Phe Val Asp Lys Asp Glu Leu Arg Glu Val Tyr Asn Phe Ala Phe
500 505 510

Leu Leu Val Leu Arg Arg Glu Val Tyr Asp Lys Asp Glu Leu Leu Leu
515 520 525

Leu Leu Glu Asp Arg Gln Leu Leu Arg Arg Glu Val Phe Cys Gly Phe
530 535 540

Arg Asp Leu Leu Glu Asp Arg Val Tyr Asp Phe Ala Phe Ser Asp Leu
545 550 555 560

Lys Leu Pro Gln Leu Cys Thr Glu Leu Lys Leu Pro Gln Leu Cys Thr
565 570 575

Glu Leu Lys Asp Glu Leu Lys Asp Glu Leu Val Leu Leu Leu Leu Glu
580 585 590

His His His His His His
595

<210> SEQ ID NO 41
<211> LENGTH: 789
<212> TYPE: PRT
<213> ORGANISM: Artificial sequence
<220> FEATURE:
<223> OTHER INFORMATION: fusion biogenic polypeptide

<400> SEQUENCE: 41

-continued

```
Met Ala Glu Gln Leu Val Asp Leu Trp Asn Glu Cys Ala Lys Ala Cys
1               5                   10                  15

Val Leu Asp Leu Lys Asp Gly Val Arg Ser Ser Arg Met Ser Val Asp
            20                  25                  30

Pro Ala Ile Ala Asp Thr Asn Gly Gln Gly Val Leu His Tyr Cys Met
        35                  40                  45

Glu Phe His Met Val Asp Gly Met Ser Ile Arg Ala Lys Arg Arg Lys
    50                  55                  60

Arg Ala Ser Ala Thr Gln Leu Tyr Lys Thr Cys Lys Gln Ala Gly Thr
65                  70                  75                  80

Cys Pro Pro Asp Ile Ile Pro Lys Val Glu Gly Lys Thr Ile Ala Glu
                85                  90                  95

Gln Ile Leu Gln Tyr Gly Ser Met Gly Val Phe Phe Gly Gly Leu Gly
            100                 105                 110

Ile Gly Thr Gly Ser Gly Thr Gly Gly Arg Thr Gly Tyr Ile Pro Leu
        115                 120                 125

Gly Thr Arg Pro Pro Thr Ala Thr Asp Thr Leu Ala Pro Val Arg Pro
    130                 135                 140

Pro Leu Thr Val Asp Pro Val Gly Pro Ser Asp Pro Ser Ile Val Ser
145                 150                 155                 160

Leu Val Glu Glu Thr Ser Phe Ile Asp Ala Gly Ala Pro Thr Ser Val
                165                 170                 175

Pro Ser Ile Pro Pro Asp Val Ser Gly Phe Ser Ile Thr Thr Ser Thr
            180                 185                 190

Asp Thr Thr Pro Ala Ile Leu Asp Ile Asn Asn Asn Thr Val Thr Thr
        195                 200                 205

Val Thr Thr His Asn Asn Pro Thr Phe Thr Asp Pro Ser Val Leu Gln
    210                 215                 220

Pro Pro Thr Pro Ala Glu Thr Gly Gly His Phe Thr Leu Ser Ser Ser
225                 230                 235                 240

Thr Ile Ser Thr His Asn Tyr Glu Glu Ile Pro Met Asp Thr Lys Asp
                245                 250                 255

Glu Leu Leu Glu His Met Ala Glu Glu Ala Phe Asp Leu Trp Asn Glu
            260                 265                 270

Cys Ala Lys Ala Cys Val Leu Asp Leu Lys Asp Gly Val Arg Ser Ser
        275                 280                 285

Arg Met Ser Val Asp Pro Ala Ile Ala Asp Thr Asn Gly Gln Gly Val
    290                 295                 300

Leu His Tyr Ser Met Val Leu Glu Gly Gly Asn Asp Ala Leu Lys Leu
305                 310                 315                 320

Ala Ile Asp Asn Ala Leu Ser Ile Thr Ser Asp Gly Leu Thr Ile Arg
                325                 330                 335

Leu Glu Gly Gly Val Glu Pro Asn Lys Pro Val Arg Tyr Ser Tyr Thr
            340                 345                 350

Arg Gln Ala Arg Gly Ser Trp Ser Leu Asn Trp Leu Val Pro Ile Gly
        355                 360                 365

His Glu Lys Pro Ser Asn Ile Lys Val Phe Ile His Glu Leu Asn Ala
    370                 375                 380

Gly Asn Gln Leu Ser His Met Ser Pro Ile Tyr Thr Ile Glu Met Gly
385                 390                 395                 400

Asp Glu Leu Leu Ala Lys Leu Ala Arg Asp Ala Thr Phe Phe Val Arg
                405                 410                 415

Ala His Glu Ser Asn Glu Met Gln Pro Thr Leu Ala Ile Ser His Ala
```

420 425 430

Gly Val Ser Val Val Met Ala Gln Thr Gln Pro Arg Arg Glu Lys Arg
435 440 445

Trp Ser Glu Trp Ala Ser Gly Lys Val Leu Cys Leu Leu Asp Pro Leu
450 455 460

Asp Gly Val Tyr Asn Tyr Leu Ala Gln Gln Arg Cys Asn Leu Asp Asp
465 470 475 480

Thr Trp Glu Gly Lys Ile Tyr Arg Val Leu Ala Gly Asn Pro Ala Lys
485 490 495

His Asp Leu Asp Ile Lys Pro Thr Val Ile Ser His Arg Leu His Phe
500 505 510

Pro Glu Gly Gly Ser Leu Ala Ala Leu Thr Ala His Gln Ala Cys His
515 520 525

Leu Pro Leu Glu Thr Phe Thr Arg His Arg Gln Pro Arg Gly Trp Glu
530 535 540

Gln Leu Glu Gln Cys Gly Tyr Pro Val Gln Arg Leu Val Ala Leu Tyr
545 550 555 560

Leu Ala Ala Arg Leu Ser Trp Asn Gln Val Asp Gln Val Ile Arg Asn
565 570 575

Ala Leu Ala Ser Pro Gly Ser Gly Gly Asp Leu Gly Glu Ala Ile Arg
580 585 590

Glu Gln Pro Glu Gln Ala Arg Leu Ala Leu Thr Leu Ala Ala Ala Glu
595 600 605

Ser Glu Arg Phe Val Arg Gln Gly Thr Gly Asn Asp Glu Ala Gly Ala
610 615 620

Ala Asn Ala Asp Val Val Ser Leu Thr Cys Pro Val Ala Ala Gly Glu
625 630 635 640

Cys Ala Gly Pro Ala Asp Ser Gly Asp Ala Leu Leu Glu Arg Asn Tyr
645 650 655

Pro Thr Gly Ala Glu Phe Leu Gly Asp Gly Gly Asp Val Ser Phe Ser
660 665 670

Thr Arg Gly Thr Gln Asn Trp Thr Val Glu Arg Leu Leu Gln Ala Glu
675 680 685

Phe Val Asp Lys Asp Glu Leu Arg Glu Val Tyr Asn Phe Ala Phe Leu
690 695 700

Leu Val Leu Arg Arg Glu Val Tyr Asp Lys Asp Glu Leu Leu Leu Leu
705 710 715 720

Leu Glu Asp Arg Gln Leu Leu Arg Arg Glu Val Phe Cys Gly Phe Arg
725 730 735

Asp Leu Leu Glu Asp Arg Val Tyr Asp Phe Ala Phe Ser Asp Leu Lys
740 745 750

Leu Pro Gln Leu Cys Thr Glu Leu Lys Leu Pro Gln Leu Cys Thr Glu
755 760 765

Leu Lys Asp Glu Leu Lys Asp Glu Leu Val Leu Leu Leu Leu Glu His
770 775 780

His His His His His
785

<210> SEQ ID NO 42
<211> LENGTH: 569
<212> TYPE: PRT
<213> ORGANISM: Artificial sequence
<220> FEATURE:
<223> OTHER INFORMATION: fusion biogenic polypeptide

<400> SEQUENCE: 42

```
Met Ala Glu Gln Leu Val Asp Leu Trp Asn Glu Cys Ala Lys Ala Cys
1               5                   10                  15

Val Leu Asp Leu Lys Asp Gly Val Arg Ser Ser Arg Met Ser Val Asp
            20                  25                  30

Pro Ala Ile Ala Asp Thr Asn Gly Gln Gly Val Leu His Tyr Cys Met
        35                  40                  45

Glu Phe Ser Phe His Gln Leu Pro Ala Arg Ser Pro Ala Pro Leu Gln
    50                  55                  60

Leu Glu His Met Ala Glu Glu Ala Phe Asp Leu Trp Asn Glu Cys Ala
65                  70                  75                  80

Lys Ala Cys Val Leu Asp Leu Lys Asp Gly Val Arg Ser Ser Arg Met
                85                  90                  95

Ser Val Asp Pro Ala Ile Ala Asp Thr Asn Gly Gln Gly Val Leu His
            100                 105                 110

Tyr Ser Met Val Leu Glu Gly Gly Asn Asp Ala Leu Lys Leu Ala Ile
        115                 120                 125

Asp Asn Ala Leu Ser Ile Thr Ser Asp Gly Leu Thr Ile Arg Leu Glu
    130                 135                 140

Gly Gly Val Glu Pro Asn Lys Pro Val Arg Tyr Ser Tyr Thr Arg Gln
145                 150                 155                 160

Ala Arg Gly Ser Trp Ser Leu Asn Trp Leu Val Pro Ile Gly His Glu
                165                 170                 175

Lys Pro Ser Asn Ile Lys Val Phe Ile His Glu Leu Asn Ala Gly Asn
            180                 185                 190

Gln Leu Ser His Met Ser Pro Ile Tyr Thr Ile Glu Met Gly Asp Glu
        195                 200                 205

Leu Leu Ala Lys Leu Ala Arg Asp Ala Thr Phe Phe Val Arg Ala His
    210                 215                 220

Glu Ser Asn Glu Met Gln Pro Thr Leu Ala Ile Ser His Ala Gly Val
225                 230                 235                 240

Ser Val Val Met Ala Gln Thr Gln Pro Arg Arg Glu Lys Arg Trp Ser
                245                 250                 255

Glu Trp Ala Ser Gly Lys Val Leu Cys Leu Leu Asp Pro Leu Asp Gly
            260                 265                 270

Val Tyr Asn Tyr Leu Ala Gln Gln Arg Cys Asn Leu Asp Asp Thr Trp
        275                 280                 285

Glu Gly Lys Ile Tyr Arg Val Leu Ala Gly Asn Pro Ala Lys His Asp
    290                 295                 300

Leu Asp Ile Lys Pro Thr Val Ile Ser His Arg Leu His Phe Pro Glu
305                 310                 315                 320

Gly Gly Ser Leu Ala Ala Leu Thr Ala His Gln Ala Cys His Leu Pro
                325                 330                 335

Leu Glu Thr Phe Thr Arg His Arg Gln Pro Arg Gly Trp Glu Gln Leu
            340                 345                 350

Glu Gln Cys Gly Tyr Pro Val Gln Arg Leu Val Ala Leu Tyr Leu Ala
        355                 360                 365

Ala Arg Leu Ser Trp Asn Gln Val Asp Gln Val Ile Arg Asn Ala Leu
    370                 375                 380

Ala Ser Pro Gly Ser Gly Gly Asp Leu Gly Glu Ala Ile Arg Glu Gln
385                 390                 395                 400

Pro Glu Gln Ala Arg Leu Ala Leu Thr Leu Ala Ala Ala Glu Ser Glu
                405                 410                 415
```

```
Arg Phe Val Arg Gln Gly Thr Gly Asn Asp Glu Ala Gly Ala Ala Asn
            420                 425                 430

Ala Asp Val Val Ser Leu Thr Cys Pro Val Ala Ala Gly Glu Cys Ala
        435                 440                 445

Gly Pro Ala Asp Ser Gly Asp Ala Leu Leu Glu Arg Asn Tyr Pro Thr
    450                 455                 460

Gly Ala Glu Phe Leu Gly Asp Gly Gly Asp Val Ser Phe Ser Thr Arg
465                 470                 475                 480

Gly Thr Gln Asn Trp Thr Val Glu Arg Leu Leu Gln Ala Glu Phe Val
                485                 490                 495

Asp Gln Ala Glu Pro Asp Gln Ala Glu Pro Asp Arg Asp Glu Leu Val
            500                 505                 510

Leu Arg Ala Arg Ala His Tyr Asn Ile Arg Ala Arg Ala His Tyr Asn
        515                 520                 525

Ile Leu Glu Asp Arg Leu Leu Val Leu Arg Ala His Tyr Asn Ile Val
    530                 535                 540

Ile Phe Arg Ala His Tyr Asn Ile Val Ile Phe Lys Asp Glu Leu Leu
545                 550                 555                 560

Val Leu Glu His His His His His His
                565


<210> SEQ ID NO 43
<211> LENGTH: 577
<212> TYPE: PRT
<213> ORGANISM: Artificial sequence
<220> FEATURE:
<223> OTHER INFORMATION: fusion biogenic polypeptide

<400> SEQUENCE: 43

Met Ala Glu Gln Leu Val Asp Leu Trp Asn Glu Cys Ala Lys Ala Cys
1               5                   10                  15

Val Leu Asp Leu Lys Asp Gly Val Arg Ser Ser Arg Met Ser Val Asp
            20                  25                  30

Pro Ala Ile Ala Asp Thr Asn Gly Gln Gly Val Leu His Tyr Cys Met
        35                  40                  45

Glu Phe Ser Ser Phe His Leu Phe His His Leu Pro Ala Arg Ala Pro
    50                  55                  60

Leu Ala Pro Ser Glu Leu Gln Pro Leu Glu His Met Ala Glu Glu Ala
65                  70                  75                  80

Phe Asp Leu Trp Asn Glu Cys Ala Lys Ala Cys Val Leu Asp Leu Lys
                85                  90                  95

Asp Gly Val Arg Ser Ser Arg Met Ser Val Asp Pro Ala Ile Ala Asp
            100                 105                 110

Thr Asn Gly Gln Gly Val Leu His Tyr Ser Met Val Leu Glu Gly Gly
        115                 120                 125

Asn Asp Ala Leu Lys Leu Ala Ile Asp Asn Ala Leu Ser Ile Thr Ser
    130                 135                 140

Asp Gly Leu Thr Ile Arg Leu Glu Gly Gly Val Glu Pro Asn Lys Pro
145                 150                 155                 160

Val Arg Tyr Ser Tyr Thr Arg Gln Ala Arg Gly Ser Trp Ser Leu Asn
                165                 170                 175

Trp Leu Val Pro Ile Gly His Glu Lys Pro Ser Asn Ile Lys Val Phe
            180                 185                 190

Ile His Glu Leu Asn Ala Gly Asn Gln Leu Ser His Met Ser Pro Ile
        195                 200                 205
```

Tyr Thr Ile Glu Met Gly Asp Glu Leu Leu Ala Lys Leu Ala Arg Asp
    210                 215                 220

Ala Thr Phe Phe Val Arg Ala His Glu Ser Asn Glu Met Gln Pro Thr
225                 230                 235                 240

Leu Ala Ile Ser His Ala Gly Val Ser Val Val Met Ala Gln Thr Gln
                245                 250                 255

Pro Arg Arg Glu Lys Arg Trp Ser Glu Trp Ala Ser Gly Lys Val Leu
            260                 265                 270

Cys Leu Leu Asp Pro Leu Asp Gly Val Tyr Asn Tyr Leu Ala Gln Gln
        275                 280                 285

Arg Cys Asn Leu Asp Asp Thr Trp Glu Gly Lys Ile Tyr Arg Val Leu
    290                 295                 300

Ala Gly Asn Pro Ala Lys His Asp Leu Asp Ile Lys Pro Thr Val Ile
305                 310                 315                 320

Ser His Arg Leu His Phe Pro Glu Gly Gly Ser Leu Ala Ala Leu Thr
                325                 330                 335

Ala His Gln Ala Cys His Leu Pro Leu Glu Thr Phe Thr Arg His Arg
            340                 345                 350

Gln Pro Arg Gly Trp Glu Gln Leu Glu Gln Cys Gly Tyr Pro Val Gln
        355                 360                 365

Arg Leu Val Ala Leu Tyr Leu Ala Ala Arg Leu Ser Trp Asn Gln Val
    370                 375                 380

Asp Gln Val Ile Arg Asn Ala Leu Ala Ser Pro Gly Ser Gly Gly Asp
385                 390                 395                 400

Leu Gly Glu Ala Ile Arg Glu Gln Pro Glu Gln Ala Arg Leu Ala Leu
                405                 410                 415

Thr Leu Ala Ala Ala Glu Ser Glu Arg Phe Val Arg Gln Gly Thr Gly
            420                 425                 430

Asn Asp Glu Ala Gly Ala Ala Asn Ala Asp Val Val Ser Leu Thr Cys
        435                 440                 445

Pro Val Ala Ala Gly Glu Cys Ala Gly Pro Ala Asp Ser Gly Asp Ala
    450                 455                 460

Leu Leu Glu Arg Asn Tyr Pro Thr Gly Ala Glu Phe Leu Gly Asp Gly
465                 470                 475                 480

Gly Asp Val Ser Phe Ser Thr Arg Gly Thr Gln Asn Trp Thr Val Glu
                485                 490                 495

Arg Leu Leu Gln Ala Glu Phe Val Asp Gln Ala Glu Pro Asp Gln Ala
            500                 505                 510

Glu Pro Asp Arg Asp Glu Leu Val Leu Arg Ala Arg Ala His Tyr Asn
        515                 520                 525

Ile Arg Ala Arg Ala His Tyr Asn Ile Leu Glu Asp Arg Leu Leu Val
    530                 535                 540

Leu Arg Ala His Tyr Asn Ile Val Ile Phe Arg Ala His Tyr Asn Ile
545                 550                 555                 560

Val Ile Phe Lys Asp Glu Leu Leu Val Leu Glu His His His His His
                565                 570                 575

His

<210> SEQ ID NO 44
<211> LENGTH: 572
<212> TYPE: PRT
<213> ORGANISM: Artificial sequence
<220> FEATURE:
<223> OTHER INFORMATION: fusion biogenic polypeptide

<400> SEQUENCE: 44

Met Ala Glu Gln Leu Val Asp Leu Trp Asn Glu Cys Ala Lys Ala Cys
1               5                   10                  15

Val Leu Asp Leu Lys Asp Gly Val Arg Ser Ser Arg Met Ser Val Asp
            20                  25                  30

Pro Ala Ile Ala Asp Thr Asn Gly Gln Gly Val Leu His Tyr Cys Met
        35                  40                  45

Glu Phe Ser Thr Pro Phe His Pro Leu Pro Ala Arg Lys Pro Leu Pro
    50                  55                  60

Leu Val Pro Leu Glu His Met Ala Glu Glu Ala Phe Asp Leu Trp Asn
65                  70                  75                  80

Glu Cys Ala Lys Ala Cys Val Leu Asp Leu Lys Asp Gly Val Arg Ser
                85                  90                  95

Ser Arg Met Ser Val Asp Pro Ala Ile Ala Asp Thr Asn Gly Gln Gly
            100                 105                 110

Val Leu His Tyr Ser Met Val Leu Glu Gly Gly Asn Asp Ala Leu Lys
        115                 120                 125

Leu Ala Ile Asp Asn Ala Leu Ser Ile Thr Ser Asp Gly Leu Thr Ile
    130                 135                 140

Arg Leu Glu Gly Gly Val Glu Pro Asn Lys Pro Val Arg Tyr Ser Tyr
145                 150                 155                 160

Thr Arg Gln Ala Arg Gly Ser Trp Ser Leu Asn Trp Leu Val Pro Ile
                165                 170                 175

Gly His Glu Lys Pro Ser Asn Ile Lys Val Phe Ile His Glu Leu Asn
            180                 185                 190

Ala Gly Asn Gln Leu Ser His Met Ser Pro Ile Tyr Thr Ile Glu Met
        195                 200                 205

Gly Asp Glu Leu Leu Ala Lys Leu Ala Arg Asp Ala Thr Phe Phe Val
    210                 215                 220

Arg Ala His Glu Ser Asn Glu Met Gln Pro Thr Leu Ala Ile Ser His
225                 230                 235                 240

Ala Gly Val Ser Val Val Met Ala Gln Thr Gln Pro Arg Arg Glu Lys
                245                 250                 255

Arg Trp Ser Glu Trp Ala Ser Gly Lys Val Leu Cys Leu Leu Asp Pro
            260                 265                 270

Leu Asp Gly Val Tyr Asn Tyr Leu Ala Gln Gln Arg Cys Asn Leu Asp
        275                 280                 285

Asp Thr Trp Glu Gly Lys Ile Tyr Arg Val Leu Ala Gly Asn Pro Ala
    290                 295                 300

Lys His Asp Leu Asp Ile Lys Pro Thr Val Ile Ser His Arg Leu His
305                 310                 315                 320

Phe Pro Glu Gly Gly Ser Leu Ala Ala Leu Thr Ala His Gln Ala Cys
                325                 330                 335

His Leu Pro Leu Glu Thr Phe Thr Arg His Arg Gln Pro Arg Gly Trp
            340                 345                 350

Glu Gln Leu Glu Gln Cys Gly Tyr Pro Val Gln Arg Leu Val Ala Leu
        355                 360                 365

Tyr Leu Ala Ala Arg Leu Ser Trp Asn Gln Val Asp Gln Val Ile Arg
    370                 375                 380

Asn Ala Leu Ala Ser Pro Gly Ser Gly Gly Asp Leu Gly Glu Ala Ile
385                 390                 395                 400

Arg Glu Gln Pro Glu Gln Ala Arg Leu Ala Leu Thr Leu Ala Ala Ala

```
                405                 410                 415

Glu Ser Glu Arg Phe Val Arg Gln Gly Thr Gly Asn Asp Glu Ala Gly
            420                 425                 430

Ala Ala Asn Ala Asp Val Val Ser Leu Thr Cys Pro Val Ala Ala Gly
        435                 440                 445

Glu Cys Ala Gly Pro Ala Asp Ser Gly Asp Ala Leu Leu Glu Arg Asn
    450                 455                 460

Tyr Pro Thr Gly Ala Glu Phe Leu Gly Asp Gly Gly Asp Val Ser Phe
465                 470                 475                 480

Ser Thr Arg Gly Thr Gln Asn Trp Thr Val Glu Arg Leu Leu Gln Ala
                485                 490                 495

Glu Phe Val Asp Gln Ala Glu Pro Asp Gln Ala Glu Pro Asp Arg Asp
            500                 505                 510

Glu Leu Val Leu Arg Ala Arg Ala His Tyr Asn Ile Arg Ala Arg Ala
        515                 520                 525

His Tyr Asn Ile Leu Glu Asp Arg Leu Leu Val Leu Arg Ala His Tyr
    530                 535                 540

Asn Ile Val Ile Phe Arg Ala His Tyr Asn Ile Val Ile Phe Lys Asp
545                 550                 555                 560

Glu Leu Leu Val Leu Glu His His His His His His
                565                 570


<210> SEQ ID NO 45
<211> LENGTH: 763
<212> TYPE: PRT
<213> ORGANISM: Artificial sequence
<220> FEATURE:
<223> OTHER INFORMATION: fusion biogenic polypeptide

<400> SEQUENCE: 45

Met Ala Glu Gln Leu Val Asp Leu Trp Asn Glu Cys Ala Lys Ala Cys
1               5                   10                  15

Val Leu Asp Leu Lys Asp Gly Val Arg Ser Ser Arg Met Ser Val Asp
            20                  25                  30

Pro Ala Ile Ala Asp Thr Asn Gly Gln Gly Val Leu His Tyr Cys Met
        35                  40                  45

Glu Phe His Met Val Asp Gly Met Ser Ile Arg Ala Lys Arg Arg Lys
    50                  55                  60

Arg Ala Ser Ala Thr Gln Leu Tyr Lys Thr Cys Lys Gln Ala Gly Thr
65                  70                  75                  80

Cys Pro Pro Asp Ile Ile Pro Lys Val Glu Gly Lys Thr Ile Ala Glu
                85                  90                  95

Gln Ile Leu Gln Tyr Gly Ser Met Gly Val Phe Phe Gly Gly Leu Gly
            100                 105                 110

Ile Gly Thr Gly Ser Gly Thr Gly Gly Arg Thr Gly Tyr Ile Pro Leu
        115                 120                 125

Gly Thr Arg Pro Pro Thr Ala Thr Asp Thr Leu Ala Pro Val Arg Pro
    130                 135                 140

Pro Leu Thr Val Asp Pro Val Gly Pro Ser Asp Pro Ser Ile Val Ser
145                 150                 155                 160

Leu Val Glu Glu Thr Ser Phe Ile Asp Ala Gly Ala Pro Thr Ser Val
                165                 170                 175

Pro Ser Ile Pro Pro Asp Val Ser Gly Phe Ser Ile Thr Thr Ser Thr
            180                 185                 190

Asp Thr Thr Pro Ala Ile Leu Asp Ile Asn Asn Asn Thr Val Thr Thr
```

-continued

```
        195                 200                 205

Val Thr Thr His Asn Asn Pro Thr Phe Thr Asp Pro Ser Val Leu Gln
    210                 215                 220

Pro Pro Thr Pro Ala Glu Thr Gly Gly His Phe Thr Leu Ser Ser Ser
225                 230                 235                 240

Thr Ile Ser Thr His Asn Tyr Glu Glu Ile Pro Met Asp Thr Lys Asp
                245                 250                 255

Glu Leu Leu Glu His Met Ala Glu Glu Ala Phe Asp Leu Trp Asn Glu
            260                 265                 270

Cys Ala Lys Ala Cys Val Leu Asp Leu Lys Asp Gly Val Arg Ser Ser
        275                 280                 285

Arg Met Ser Val Asp Pro Ala Ile Ala Asp Thr Asn Gly Gln Gly Val
    290                 295                 300

Leu His Tyr Ser Met Val Leu Glu Gly Gly Asn Asp Ala Leu Lys Leu
305                 310                 315                 320

Ala Ile Asp Asn Ala Leu Ser Ile Thr Ser Asp Gly Leu Thr Ile Arg
                325                 330                 335

Leu Glu Gly Gly Val Glu Pro Asn Lys Pro Val Arg Tyr Ser Tyr Thr
            340                 345                 350

Arg Gln Ala Arg Gly Ser Trp Ser Leu Asn Trp Leu Val Pro Ile Gly
        355                 360                 365

His Glu Lys Pro Ser Asn Ile Lys Val Phe Ile His Glu Leu Asn Ala
    370                 375                 380

Gly Asn Gln Leu Ser His Met Ser Pro Ile Tyr Thr Ile Glu Met Gly
385                 390                 395                 400

Asp Glu Leu Leu Ala Lys Leu Ala Arg Asp Ala Thr Phe Phe Val Arg
                405                 410                 415

Ala His Glu Ser Asn Glu Met Gln Pro Thr Leu Ala Ile Ser His Ala
            420                 425                 430

Gly Val Ser Val Val Met Ala Gln Thr Gln Pro Arg Arg Glu Lys Arg
        435                 440                 445

Trp Ser Glu Trp Ala Ser Gly Lys Val Leu Cys Leu Leu Asp Pro Leu
    450                 455                 460

Asp Gly Val Tyr Asn Tyr Leu Ala Gln Gln Arg Cys Asn Leu Asp Asp
465                 470                 475                 480

Thr Trp Glu Gly Lys Ile Tyr Arg Val Leu Ala Gly Asn Pro Ala Lys
                485                 490                 495

His Asp Leu Asp Ile Lys Pro Thr Val Ile Ser His Arg Leu His Phe
            500                 505                 510

Pro Glu Gly Gly Ser Leu Ala Ala Leu Thr Ala His Gln Ala Cys His
        515                 520                 525

Leu Pro Leu Glu Thr Phe Thr Arg His Arg Gln Pro Arg Gly Trp Glu
    530                 535                 540

Gln Leu Glu Gln Cys Gly Tyr Pro Val Gln Arg Leu Val Ala Leu Tyr
545                 550                 555                 560

Leu Ala Ala Arg Leu Ser Trp Asn Gln Val Asp Gln Val Ile Arg Asn
                565                 570                 575

Ala Leu Ala Ser Pro Gly Ser Gly Gly Asp Leu Gly Glu Ala Ile Arg
            580                 585                 590

Glu Gln Pro Glu Gln Ala Arg Leu Ala Leu Thr Leu Ala Ala Ala Glu
        595                 600                 605

Ser Glu Arg Phe Val Arg Gln Gly Thr Gly Asn Asp Glu Ala Gly Ala
    610                 615                 620
```

Ala Asn Ala Asp Val Val Ser Leu Thr Cys Pro Val Ala Ala Gly Glu
625 630 635 640

Cys Ala Gly Pro Ala Asp Ser Gly Asp Ala Leu Leu Glu Arg Asn Tyr
645 650 655

Pro Thr Gly Ala Glu Phe Leu Gly Asp Gly Gly Asp Val Ser Phe Ser
660 665 670

Thr Arg Gly Thr Gln Asn Trp Thr Val Glu Arg Leu Leu Gln Ala Glu
675 680 685

Phe Val Asp Gln Ala Glu Pro Asp Gln Ala Glu Pro Asp Arg Asp Glu
690 695 700

Leu Val Leu Arg Ala Arg Ala His Tyr Asn Ile Arg Ala Arg Ala His
705 710 715 720

Tyr Asn Ile Leu Glu Asp Arg Leu Leu Val Leu Arg Ala His Tyr Asn
725 730 735

Ile Val Ile Phe Arg Ala His Tyr Asn Ile Val Ile Phe Lys Asp Glu
740 745 750

Leu Leu Val Leu Glu His His His His His His
755 760

<210> SEQ ID NO 46
<211> LENGTH: 553
<212> TYPE: PRT
<213> ORGANISM: Artificial sequence
<220> FEATURE:
<223> OTHER INFORMATION: fusion biogenic polypeptide

<400> SEQUENCE: 46

Met Ala Glu Gln Leu Val Asp Leu Trp Asn Glu Cys Ala Lys Ala Cys
1 5 10 15

Val Leu Asp Leu Lys Asp Gly Val Arg Ser Ser Arg Met Ser Val Asp
20 25 30

Pro Ala Ile Ala Asp Thr Asn Gly Gln Gly Val Leu His Tyr Cys Met
35 40 45

Glu Phe Ser Phe His Gln Leu Pro Ala Arg Ser Pro Ala Pro Leu Gln
50 55 60

Leu Glu His Met Ala Glu Glu Ala Phe Asp Leu Trp Asn Glu Cys Ala
65 70 75 80

Lys Ala Cys Val Leu Asp Leu Lys Asp Gly Val Arg Ser Ser Arg Met
85 90 95

Ser Val Asp Pro Ala Ile Ala Asp Thr Asn Gly Gln Gly Val Leu His
100 105 110

Tyr Ser Met Val Leu Glu Gly Gly Asn Asp Ala Leu Lys Leu Ala Ile
115 120 125

Asp Asn Ala Leu Ser Ile Thr Ser Asp Gly Leu Thr Ile Arg Leu Glu
130 135 140

Gly Gly Val Glu Pro Asn Lys Pro Val Arg Tyr Ser Tyr Thr Arg Gln
145 150 155 160

Ala Arg Gly Ser Trp Ser Leu Asn Trp Leu Val Pro Ile Gly His Glu
165 170 175

Lys Pro Ser Asn Ile Lys Val Phe Ile His Glu Leu Asn Ala Gly Asn
180 185 190

Gln Leu Ser His Met Ser Pro Ile Tyr Thr Ile Glu Met Gly Asp Glu
195 200 205

Leu Leu Ala Lys Leu Ala Arg Asp Ala Thr Phe Phe Val Arg Ala His
210 215 220

```
Glu Ser Asn Glu Met Gln Pro Thr Leu Ala Ile Ser His Ala Gly Val
225                 230                 235                 240

Ser Val Val Met Ala Gln Thr Gln Pro Arg Arg Glu Lys Arg Trp Ser
                245                 250                 255

Glu Trp Ala Ser Gly Lys Val Leu Cys Leu Leu Asp Pro Leu Asp Gly
            260                 265                 270

Val Tyr Asn Tyr Leu Ala Gln Gln Arg Cys Asn Leu Asp Asp Thr Trp
        275                 280                 285

Glu Gly Lys Ile Tyr Arg Val Leu Ala Gly Asn Pro Ala Lys His Asp
    290                 295                 300

Leu Asp Ile Lys Pro Thr Val Ile Ser His Arg Leu His Phe Pro Glu
305                 310                 315                 320

Gly Gly Ser Leu Ala Ala Leu Thr Ala His Gln Ala Cys His Leu Pro
                325                 330                 335

Leu Glu Thr Phe Thr Arg His Arg Gln Pro Arg Gly Trp Glu Gln Leu
            340                 345                 350

Glu Gln Cys Gly Tyr Pro Val Gln Arg Leu Val Ala Leu Tyr Leu Ala
        355                 360                 365

Ala Arg Leu Ser Trp Asn Gln Val Asp Gln Val Ile Arg Asn Ala Leu
    370                 375                 380

Ala Ser Pro Gly Ser Gly Gly Asp Leu Gly Glu Ala Ile Arg Glu Gln
385                 390                 395                 400

Pro Glu Gln Ala Arg Leu Ala Leu Thr Leu Ala Ala Ala Glu Ser Glu
                405                 410                 415

Arg Phe Val Arg Gln Gly Thr Gly Asn Asp Glu Ala Gly Ala Ala Asn
            420                 425                 430

Ala Asp Val Val Ser Leu Thr Cys Pro Val Ala Ala Gly Glu Cys Ala
        435                 440                 445

Gly Pro Ala Asp Ser Gly Asp Ala Leu Leu Glu Arg Asn Tyr Pro Thr
    450                 455                 460

Gly Ala Glu Phe Leu Gly Asp Gly Gly Asp Val Glu Phe Val Asp Val
465                 470                 475                 480

Phe Leu Gln Lys Tyr Pro His Thr His Leu Val His Gln Ala Leu Asp
                485                 490                 495

Val Phe Leu Gln Lys Tyr Pro His Thr His Leu Val His Gln Ala Leu
            500                 505                 510

Asp Val Phe Leu Gln Lys Tyr Pro His Thr His Leu Val His Gln Ala
        515                 520                 525

Leu Asp Val Phe Leu Gln Lys Tyr Pro His Thr His Leu Val His Gln
    530                 535                 540

Ala Leu Glu His His His His His His
545                 550
```

<210> SEQ ID NO 47
<211> LENGTH: 561
<212> TYPE: PRT
<213> ORGANISM: Artificial sequence
<220> FEATURE:
<223> OTHER INFORMATION: fusion biogenic polypeptide

<400> SEQUENCE: 47

```
Met Ala Glu Gln Leu Val Asp Leu Trp Asn Glu Cys Ala Lys Ala Cys
1               5                   10                  15

Val Leu Asp Leu Lys Asp Gly Val Arg Ser Ser Arg Met Ser Val Asp
            20                  25                  30
```

-continued

```
Pro Ala Ile Ala Asp Thr Asn Gly Gln Gly Val Leu His Tyr Cys Met
        35                  40                  45

Glu Phe Ser Ser Phe His Leu Phe His His Leu Pro Ala Arg Ala Pro
    50                  55                  60

Leu Ala Pro Ser Glu Leu Gln Pro Leu Glu His Met Ala Glu Glu Ala
65                  70                  75                  80

Phe Asp Leu Trp Asn Glu Cys Ala Lys Ala Cys Val Leu Asp Leu Lys
                85                  90                  95

Asp Gly Val Arg Ser Ser Arg Met Ser Val Asp Pro Ala Ile Ala Asp
            100                 105                 110

Thr Asn Gly Gln Gly Val Leu His Tyr Ser Met Val Leu Glu Gly Gly
        115                 120                 125

Asn Asp Ala Leu Lys Leu Ala Ile Asp Asn Ala Leu Ser Ile Thr Ser
    130                 135                 140

Asp Gly Leu Thr Ile Arg Leu Glu Gly Gly Val Glu Pro Asn Lys Pro
145                 150                 155                 160

Val Arg Tyr Ser Tyr Thr Arg Gln Ala Arg Gly Ser Trp Ser Leu Asn
                165                 170                 175

Trp Leu Val Pro Ile Gly His Glu Lys Pro Ser Asn Ile Lys Val Phe
            180                 185                 190

Ile His Glu Leu Asn Ala Gly Asn Gln Leu Ser His Met Ser Pro Ile
        195                 200                 205

Tyr Thr Ile Glu Met Gly Asp Glu Leu Leu Ala Lys Leu Ala Arg Asp
    210                 215                 220

Ala Thr Phe Phe Val Arg Ala His Glu Ser Asn Glu Met Gln Pro Thr
225                 230                 235                 240

Leu Ala Ile Ser His Ala Gly Val Ser Val Val Met Ala Gln Thr Gln
                245                 250                 255

Pro Arg Arg Glu Lys Arg Trp Ser Glu Trp Ala Ser Gly Lys Val Leu
            260                 265                 270

Cys Leu Leu Asp Pro Leu Asp Gly Val Tyr Asn Tyr Leu Ala Gln Gln
        275                 280                 285

Arg Cys Asn Leu Asp Asp Thr Trp Glu Gly Lys Ile Tyr Arg Val Leu
    290                 295                 300

Ala Gly Asn Pro Ala Lys His Asp Leu Asp Ile Lys Pro Thr Val Ile
305                 310                 315                 320

Ser His Arg Leu His Phe Pro Glu Gly Gly Ser Leu Ala Ala Leu Thr
                325                 330                 335

Ala His Gln Ala Cys His Leu Pro Leu Glu Thr Phe Thr Arg His Arg
            340                 345                 350

Gln Pro Arg Gly Trp Glu Gln Leu Glu Gln Cys Gly Tyr Pro Val Gln
        355                 360                 365

Arg Leu Val Ala Leu Tyr Leu Ala Ala Arg Leu Ser Trp Asn Gln Val
    370                 375                 380

Asp Gln Val Ile Arg Asn Ala Leu Ala Ser Pro Gly Ser Gly Gly Asp
385                 390                 395                 400

Leu Gly Glu Ala Ile Arg Glu Gln Pro Glu Gln Ala Arg Leu Ala Leu
                405                 410                 415

Thr Leu Ala Ala Ala Glu Ser Glu Arg Phe Val Arg Gln Gly Thr Gly
            420                 425                 430

Asn Asp Glu Ala Gly Ala Ala Asn Ala Asp Val Val Ser Leu Thr Cys
        435                 440                 445
```

```
Pro Val Ala Ala Gly Glu Cys Ala Gly Pro Ala Asp Ser Gly Asp Ala
    450                 455                 460

Leu Leu Glu Arg Asn Tyr Pro Thr Gly Ala Glu Phe Leu Gly Asp Gly
465                 470                 475                 480

Gly Asp Val Glu Phe Val Asp Val Phe Leu Gln Lys Tyr Pro His Thr
                485                 490                 495

His Leu Val His Gln Ala Leu Asp Val Phe Leu Gln Lys Tyr Pro His
            500                 505                 510

Thr His Leu Val His Gln Ala Leu Asp Val Phe Leu Gln Lys Tyr Pro
        515                 520                 525

His Thr His Leu Val His Gln Ala Leu Asp Val Phe Leu Gln Lys Tyr
    530                 535                 540

Pro His Thr His Leu Val His Gln Ala Leu Glu His His His His His
545                 550                 555                 560

His


<210> SEQ ID NO 48
<211> LENGTH: 556
<212> TYPE: PRT
<213> ORGANISM: Artificial sequence
<220> FEATURE:
<223> OTHER INFORMATION: fusion biogenic polypeptide

<400> SEQUENCE: 48

Met Ala Glu Gln Leu Val Asp Leu Trp Asn Glu Cys Ala Lys Ala Cys
1               5                   10                  15

Val Leu Asp Leu Lys Asp Gly Val Arg Ser Ser Arg Met Ser Val Asp
            20                  25                  30

Pro Ala Ile Ala Asp Thr Asn Gly Gln Gly Val Leu His Tyr Cys Met
        35                  40                  45

Glu Phe Ser Thr Pro Phe His Pro Leu Pro Ala Arg Lys Pro Leu Pro
    50                  55                  60

Leu Val Pro Leu Glu His Met Ala Glu Glu Ala Phe Asp Leu Trp Asn
65                  70                  75                  80

Glu Cys Ala Lys Ala Cys Val Leu Asp Leu Lys Asp Gly Val Arg Ser
                85                  90                  95

Ser Arg Met Ser Val Asp Pro Ala Ile Ala Asp Thr Asn Gly Gln Gly
            100                 105                 110

Val Leu His Tyr Ser Met Val Leu Glu Gly Gly Asn Asp Ala Leu Lys
        115                 120                 125

Leu Ala Ile Asp Asn Ala Leu Ser Ile Thr Ser Asp Gly Leu Thr Ile
    130                 135                 140

Arg Leu Glu Gly Gly Val Glu Pro Asn Lys Pro Val Arg Tyr Ser Tyr
145                 150                 155                 160

Thr Arg Gln Ala Arg Gly Ser Trp Ser Leu Asn Trp Leu Val Pro Ile
                165                 170                 175

Gly His Glu Lys Pro Ser Asn Ile Lys Val Phe Ile His Glu Leu Asn
            180                 185                 190

Ala Gly Asn Gln Leu Ser His Met Ser Pro Ile Tyr Thr Ile Glu Met
        195                 200                 205

Gly Asp Glu Leu Leu Ala Lys Leu Ala Arg Asp Ala Thr Phe Phe Val
    210                 215                 220

Arg Ala His Glu Ser Asn Glu Met Gln Pro Thr Leu Ala Ile Ser His
225                 230                 235                 240

Ala Gly Val Ser Val Val Met Ala Gln Thr Gln Pro Arg Arg Glu Lys
```

```
                245                 250                 255

Arg Trp Ser Glu Trp Ala Ser Gly Lys Val Leu Cys Leu Leu Asp Pro
            260                 265                 270

Leu Asp Gly Val Tyr Asn Tyr Leu Ala Gln Gln Arg Cys Asn Leu Asp
        275                 280                 285

Asp Thr Trp Glu Gly Lys Ile Tyr Arg Val Leu Ala Gly Asn Pro Ala
    290                 295                 300

Lys His Asp Leu Asp Ile Lys Pro Thr Val Ile Ser His Arg Leu His
305                 310                 315                 320

Phe Pro Glu Gly Gly Ser Leu Ala Ala Leu Thr Ala His Gln Ala Cys
                325                 330                 335

His Leu Pro Leu Glu Thr Phe Thr Arg His Arg Gln Pro Arg Gly Trp
            340                 345                 350

Glu Gln Leu Glu Gln Cys Gly Tyr Pro Val Gln Arg Leu Val Ala Leu
        355                 360                 365

Tyr Leu Ala Ala Arg Leu Ser Trp Asn Gln Val Asp Gln Val Ile Arg
    370                 375                 380

Asn Ala Leu Ala Ser Pro Gly Ser Gly Gly Asp Leu Gly Glu Ala Ile
385                 390                 395                 400

Arg Glu Gln Pro Glu Gln Ala Arg Leu Ala Leu Thr Leu Ala Ala Ala
                405                 410                 415

Glu Ser Glu Arg Phe Val Arg Gln Gly Thr Gly Asn Asp Glu Ala Gly
            420                 425                 430

Ala Ala Asn Ala Asp Val Val Ser Leu Thr Cys Pro Val Ala Ala Gly
        435                 440                 445

Glu Cys Ala Gly Pro Ala Asp Ser Gly Asp Ala Leu Leu Glu Arg Asn
    450                 455                 460

Tyr Pro Thr Gly Ala Glu Phe Leu Gly Asp Gly Gly Asp Val Glu Phe
465                 470                 475                 480

Val Asp Val Phe Leu Gln Lys Tyr Pro His Thr His Leu Val His Gln
                485                 490                 495

Ala Leu Asp Val Phe Leu Gln Lys Tyr Pro His Thr His Leu Val His
            500                 505                 510

Gln Ala Leu Asp Val Phe Leu Gln Lys Tyr Pro His Thr His Leu Val
        515                 520                 525

His Gln Ala Leu Asp Val Phe Leu Gln Lys Tyr Pro His Thr His Leu
    530                 535                 540

Val His Gln Ala Leu Glu His His His His His His
545                 550                 555
```

<210> SEQ ID NO 49
<211> LENGTH: 758
<212> TYPE: PRT
<213> ORGANISM: Artificial sequence
<220> FEATURE:
<223> OTHER INFORMATION: fusion biogenic polypeptide

<400> SEQUENCE: 49

```
Met Ala Glu Gln Leu Val Asp Leu Trp Asn Glu Cys Ala Lys Ala Cys
1               5                   10                  15

Val Leu Asp Leu Lys Asp Gly Val Arg Ser Ser Arg Met Ser Val Asp
            20                  25                  30

Pro Ala Ile Ala Asp Thr Asn Gly Gln Gly Val Leu His Tyr Cys Met
        35                  40                  45

Glu Phe Ser Phe His Gln Leu Pro Ala Arg Ser Pro Ala Pro Leu Gln
```

-continued

```
    50                  55                  60

Leu Glu His Met Ala Glu Glu Ala Phe Asp Leu Trp Asn Glu Cys Ala
65                  70                  75                  80

Lys Ala Cys Val Leu Asp Leu Lys Asp Gly Val Arg Ser Ser Arg Met
                85                  90                  95

Ser Val Asp Pro Ala Ile Ala Asp Thr Asn Gly Gln Gly Val Leu His
            100                 105                 110

Tyr Ser Met Val Leu Glu Gly Gly Asn Asp Ala Leu Lys Leu Ala Ile
        115                 120                 125

Asp Asn Ala Leu Ser Ile Thr Ser Asp Gly Leu Thr Ile Arg Leu Glu
    130                 135                 140

Gly Gly Val Glu Pro Asn Lys Pro Val Arg Tyr Ser Tyr Thr Arg Gln
145                 150                 155                 160

Ala Arg Gly Ser Trp Ser Leu Asn Trp Leu Val Pro Ile Gly His Glu
                165                 170                 175

Lys Pro Ser Asn Ile Lys Val Phe Ile His Glu Leu Asn Ala Gly Asn
            180                 185                 190

Gln Leu Ser His Met Ser Pro Ile Tyr Thr Ile Glu Met Gly Asp Glu
        195                 200                 205

Leu Leu Ala Lys Leu Ala Arg Asp Ala Thr Phe Phe Val Arg Ala His
    210                 215                 220

Glu Ser Asn Glu Met Gln Pro Thr Leu Ala Ile Ser His Ala Gly Val
225                 230                 235                 240

Ser Val Val Met Ala Gln Thr Gln Pro Arg Arg Glu Lys Arg Trp Ser
                245                 250                 255

Glu Trp Ala Ser Gly Lys Val Leu Cys Leu Leu Asp Pro Leu Asp Gly
            260                 265                 270

Val Tyr Asn Tyr Leu Ala Gln Gln Arg Cys Asn Leu Asp Asp Thr Trp
        275                 280                 285

Glu Gly Lys Ile Tyr Arg Val Leu Ala Gly Asn Pro Ala Lys His Asp
    290                 295                 300

Leu Asp Ile Lys Pro Thr Val Ile Ser His Arg Leu His Phe Pro Glu
305                 310                 315                 320

Gly Gly Ser Leu Ala Ala Leu Thr Ala His Gln Ala Cys His Leu Pro
                325                 330                 335

Leu Glu Thr Phe Thr Arg His Arg Gln Pro Arg Gly Trp Glu Gln Leu
            340                 345                 350

Glu Gln Cys Gly Tyr Pro Val Gln Arg Leu Val Ala Leu Tyr Leu Ala
        355                 360                 365

Ala Arg Leu Ser Trp Asn Gln Val Asp Gln Val Ile Arg Asn Ala Leu
    370                 375                 380

Ala Ser Pro Gly Ser Gly Gly Asp Leu Gly Glu Ala Ile Arg Glu Gln
385                 390                 395                 400

Pro Glu Gln Ala Arg Leu Ala Leu Thr Leu Ala Ala Ala Glu Ser Glu
                405                 410                 415

Arg Phe Val Arg Gln Gly Thr Gly Asn Asp Glu Ala Gly Ala Ala Asn
            420                 425                 430

Ala Asp Val Val Ser Leu Thr Cys Pro Val Ala Ala Gly Glu Cys Ala
        435                 440                 445

Gly Pro Ala Asp Ser Gly Asp Ala Leu Leu Glu Arg Asn Tyr Pro Thr
    450                 455                 460

Gly Ala Glu Phe Leu Gly Asp Gly Gly Asp Val Glu Phe Leu Leu Glu
465                 470                 475                 480
```

-continued

Pro His Thr His Leu Val His Gln Ala Asn Val Leu Leu Ala Leu Gln
485 490 495

Leu Leu Leu Glu Asp Arg Glu Phe Val Phe Leu Gln Lys Tyr Pro His
500 505 510

Val Glu Pro His Thr His Leu Val His Gln Ala Asn Val Leu Leu Ala
515 520 525

Leu Gln Leu Leu Leu Glu Asp Arg Glu Phe Val Phe Leu Gln Lys Tyr
530 535 540

Pro His Val Glu Pro His Thr His Leu Val His Gln Ala Asn Val Leu
545 550 555 560

Leu Ala Leu Gln Leu Leu Leu Glu Asp Arg Glu Phe Val Phe Leu Gln
565 570 575

Lys Tyr Pro His Val Glu Pro His Thr His Leu Val His Gln Ala Asn
580 585 590

Val Leu Leu Ala Leu Gln Leu Leu Leu Glu Asp Arg Glu Phe Val Phe
595 600 605

Leu Gln Lys Tyr Pro His Val Glu Pro His Thr His Leu Val His Gln
610 615 620

Ala Asn Val Leu Leu Ala Leu Gln Leu Leu Leu Glu Asp Arg Glu Phe
625 630 635 640

Val Phe Leu Gln Lys Tyr Pro His Val Glu Pro His Thr His Leu Val
645 650 655

His Gln Ala Asn Val Leu Leu Ala Leu Gln Leu Leu Leu Glu Asp Arg
660 665 670

Glu Phe Val Phe Leu Gln Lys Tyr Pro His Val Glu Pro His Thr His
675 680 685

Leu Val His Gln Ala Asn Val Leu Leu Ala Leu Gln Leu Leu Leu Glu
690 695 700

Asp Arg Glu Phe Val Phe Leu Gln Lys Tyr Pro His Val Glu Pro His
705 710 715 720

Thr His Leu Val His Gln Ala Asn Val Leu Leu Ala Leu Gln Leu Leu
725 730 735

Leu Glu Asp Arg Glu Phe Val Phe Leu Gln Lys Tyr Pro His Val Glu
740 745 750

His His His His His His
755

<210> SEQ ID NO 50
<211> LENGTH: 766
<212> TYPE: PRT
<213> ORGANISM: Artificial sequence
<220> FEATURE:
<223> OTHER INFORMATION: fusion biogenic polypeptide

<400> SEQUENCE: 50

Met Ala Glu Gln Leu Val Asp Leu Trp Asn Glu Cys Ala Lys Ala Cys
1 5 10 15

Val Leu Asp Leu Lys Asp Gly Val Arg Ser Ser Arg Met Ser Val Asp
20 25 30

Pro Ala Ile Ala Asp Thr Asn Gly Gln Gly Val Leu His Tyr Cys Met
35 40 45

Glu Phe Ser Ser Phe His Leu Phe His His Leu Pro Ala Arg Ala Pro
50 55 60

Leu Ala Pro Ser Glu Leu Gln Pro Leu Glu His Met Ala Glu Glu Ala
65 70 75 80

-continued

```
Phe Asp Leu Trp Asn Glu Cys Ala Lys Ala Cys Val Leu Asp Leu Lys
                85                  90                  95

Asp Gly Val Arg Ser Ser Arg Met Ser Val Asp Pro Ala Ile Ala Asp
            100                 105                 110

Thr Asn Gly Gln Gly Val Leu His Tyr Ser Met Val Leu Glu Gly Gly
        115                 120                 125

Asn Asp Ala Leu Lys Leu Ala Ile Asp Asn Ala Leu Ser Ile Thr Ser
    130                 135                 140

Asp Gly Leu Thr Ile Arg Leu Glu Gly Gly Val Glu Pro Asn Lys Pro
145                 150                 155                 160

Val Arg Tyr Ser Tyr Thr Arg Gln Ala Arg Gly Ser Trp Ser Leu Asn
                165                 170                 175

Trp Leu Val Pro Ile Gly His Glu Lys Pro Ser Asn Ile Lys Val Phe
            180                 185                 190

Ile His Glu Leu Asn Ala Gly Asn Gln Leu Ser His Met Ser Pro Ile
        195                 200                 205

Tyr Thr Ile Glu Met Gly Asp Glu Leu Leu Ala Lys Leu Ala Arg Asp
    210                 215                 220

Ala Thr Phe Phe Val Arg Ala His Glu Ser Asn Glu Met Gln Pro Thr
225                 230                 235                 240

Leu Ala Ile Ser His Ala Gly Val Ser Val Val Met Ala Gln Thr Gln
                245                 250                 255

Pro Arg Arg Glu Lys Arg Trp Ser Glu Trp Ala Ser Gly Lys Val Leu
            260                 265                 270

Cys Leu Leu Asp Pro Leu Asp Gly Val Tyr Asn Tyr Leu Ala Gln Gln
        275                 280                 285

Arg Cys Asn Leu Asp Asp Thr Trp Glu Gly Lys Ile Tyr Arg Val Leu
    290                 295                 300

Ala Gly Asn Pro Ala Lys His Asp Leu Asp Ile Lys Pro Thr Val Ile
305                 310                 315                 320

Ser His Arg Leu His Phe Pro Glu Gly Gly Ser Leu Ala Ala Leu Thr
                325                 330                 335

Ala His Gln Ala Cys His Leu Pro Leu Glu Thr Phe Thr Arg His Arg
            340                 345                 350

Gln Pro Arg Gly Trp Glu Gln Leu Glu Gln Cys Gly Tyr Pro Val Gln
        355                 360                 365

Arg Leu Val Ala Leu Tyr Leu Ala Ala Arg Leu Ser Trp Asn Gln Val
    370                 375                 380

Asp Gln Val Ile Arg Asn Ala Leu Ala Ser Pro Gly Ser Gly Gly Asp
385                 390                 395                 400

Leu Gly Glu Ala Ile Arg Glu Gln Pro Glu Gln Ala Arg Leu Ala Leu
                405                 410                 415

Thr Leu Ala Ala Ala Glu Ser Glu Arg Phe Val Arg Gln Gly Thr Gly
            420                 425                 430

Asn Asp Glu Ala Gly Ala Ala Asn Ala Asp Val Val Ser Leu Thr Cys
        435                 440                 445

Pro Val Ala Ala Gly Glu Cys Ala Gly Pro Ala Asp Ser Gly Asp Ala
    450                 455                 460

Leu Leu Glu Arg Asn Tyr Pro Thr Gly Ala Glu Phe Leu Gly Asp Gly
465                 470                 475                 480

Gly Asp Val Glu Phe Leu Leu Glu Pro His Thr His Leu Val His Gln
                485                 490                 495
```

-continued

```
Ala Asn Val Leu Leu Ala Leu Gln Leu Leu Leu Glu Asp Arg Glu Phe
            500                 505                 510

Val Phe Leu Gln Lys Tyr Pro His Val Glu Pro His Thr His Leu Val
        515                 520                 525

His Gln Ala Asn Val Leu Leu Ala Leu Gln Leu Leu Leu Glu Asp Arg
    530                 535                 540

Glu Phe Val Phe Leu Gln Lys Tyr Pro His Val Glu Pro His Thr His
545                 550                 555                 560

Leu Val His Gln Ala Asn Val Leu Leu Ala Leu Gln Leu Leu Leu Glu
                565                 570                 575

Asp Arg Glu Phe Val Phe Leu Gln Lys Tyr Pro His Val Glu Pro His
            580                 585                 590

Thr His Leu Val His Gln Ala Asn Val Leu Leu Ala Leu Gln Leu Leu
        595                 600                 605

Leu Glu Asp Arg Glu Phe Val Phe Leu Gln Lys Tyr Pro His Val Glu
    610                 615                 620

Pro His Thr His Leu Val His Gln Ala Asn Val Leu Leu Ala Leu Gln
625                 630                 635                 640

Leu Leu Leu Glu Asp Arg Glu Phe Val Phe Leu Gln Lys Tyr Pro His
                645                 650                 655

Val Glu Pro His Thr His Leu Val His Gln Ala Asn Val Leu Leu Ala
            660                 665                 670

Leu Gln Leu Leu Leu Glu Asp Arg Glu Phe Val Phe Leu Gln Lys Tyr
        675                 680                 685

Pro His Val Glu Pro His Thr His Leu Val His Gln Ala Asn Val Leu
    690                 695                 700

Leu Ala Leu Gln Leu Leu Leu Glu Asp Arg Glu Phe Val Phe Leu Gln
705                 710                 715                 720

Lys Tyr Pro His Val Glu Pro His Thr His Leu Val His Gln Ala Asn
                725                 730                 735

Val Leu Leu Ala Leu Gln Leu Leu Leu Glu Asp Arg Glu Phe Val Phe
            740                 745                 750

Leu Gln Lys Tyr Pro His Val Glu His His His His His His
        755                 760                 765


<210> SEQ ID NO 51
<211> LENGTH: 761
<212> TYPE: PRT
<213> ORGANISM: Artificial sequence
<220> FEATURE:
<223> OTHER INFORMATION: fusion biogenic polypeptide

<400> SEQUENCE: 51

Met Ala Glu Gln Leu Val Asp Leu Trp Asn Glu Cys Ala Lys Ala Cys
1               5                   10                  15

Val Leu Asp Leu Lys Asp Gly Val Arg Ser Ser Arg Met Ser Val Asp
            20                  25                  30

Pro Ala Ile Ala Asp Thr Asn Gly Gln Gly Val Leu His Tyr Cys Met
        35                  40                  45

Glu Phe Ser Thr Pro Phe His Pro Leu Pro Ala Arg Lys Pro Leu Pro
    50                  55                  60

Leu Val Pro Leu Glu His Met Ala Glu Glu Ala Phe Asp Leu Trp Asn
65                  70                  75                  80

Glu Cys Ala Lys Ala Cys Val Leu Asp Leu Lys Asp Gly Val Arg Ser
                85                  90                  95
```

-continued

```
Ser Arg Met Ser Val Asp Pro Ala Ile Ala Asp Thr Asn Gly Gln Gly
            100                 105                 110

Val Leu His Tyr Ser Met Val Leu Glu Gly Gly Asn Asp Ala Leu Lys
        115                 120                 125

Leu Ala Ile Asp Asn Ala Leu Ser Ile Thr Ser Asp Gly Leu Thr Ile
    130                 135                 140

Arg Leu Glu Gly Gly Val Glu Pro Asn Lys Pro Val Arg Tyr Ser Tyr
145                 150                 155                 160

Thr Arg Gln Ala Arg Gly Ser Trp Ser Leu Asn Trp Leu Val Pro Ile
                165                 170                 175

Gly His Glu Lys Pro Ser Asn Ile Lys Val Phe Ile His Glu Leu Asn
            180                 185                 190

Ala Gly Asn Gln Leu Ser His Met Ser Pro Ile Tyr Thr Ile Glu Met
        195                 200                 205

Gly Asp Glu Leu Leu Ala Lys Leu Ala Arg Asp Ala Thr Phe Phe Val
    210                 215                 220

Arg Ala His Glu Ser Asn Glu Met Gln Pro Thr Leu Ala Ile Ser His
225                 230                 235                 240

Ala Gly Val Ser Val Val Met Ala Gln Thr Gln Pro Arg Arg Glu Lys
                245                 250                 255

Arg Trp Ser Glu Trp Ala Ser Gly Lys Val Leu Cys Leu Leu Asp Pro
            260                 265                 270

Leu Asp Gly Val Tyr Asn Tyr Leu Ala Gln Gln Arg Cys Asn Leu Asp
        275                 280                 285

Asp Thr Trp Glu Gly Lys Ile Tyr Arg Val Leu Ala Gly Asn Pro Ala
    290                 295                 300

Lys His Asp Leu Asp Ile Lys Pro Thr Val Ile Ser His Arg Leu His
305                 310                 315                 320

Phe Pro Glu Gly Gly Ser Leu Ala Ala Leu Thr Ala His Gln Ala Cys
                325                 330                 335

His Leu Pro Leu Glu Thr Phe Thr Arg His Arg Gln Pro Arg Gly Trp
            340                 345                 350

Glu Gln Leu Glu Gln Cys Gly Tyr Pro Val Gln Arg Leu Val Ala Leu
        355                 360                 365

Tyr Leu Ala Ala Arg Leu Ser Trp Asn Gln Val Asp Gln Val Ile Arg
    370                 375                 380

Asn Ala Leu Ala Ser Pro Gly Ser Gly Gly Asp Leu Gly Glu Ala Ile
385                 390                 395                 400

Arg Glu Gln Pro Glu Gln Ala Arg Leu Ala Leu Thr Leu Ala Ala Ala
                405                 410                 415

Glu Ser Glu Arg Phe Val Arg Gln Gly Thr Gly Asn Asp Glu Ala Gly
            420                 425                 430

Ala Ala Asn Ala Asp Val Val Ser Leu Thr Cys Pro Val Ala Ala Gly
        435                 440                 445

Glu Cys Ala Gly Pro Ala Asp Ser Gly Asp Ala Leu Leu Glu Arg Asn
    450                 455                 460

Tyr Pro Thr Gly Ala Glu Phe Leu Gly Asp Gly Gly Asp Val Glu Phe
465                 470                 475                 480

Leu Leu Glu Pro His Thr His Leu Val His Gln Ala Asn Val Leu Leu
                485                 490                 495

Ala Leu Gln Leu Leu Leu Glu Asp Arg Glu Phe Val Phe Leu Gln Lys
            500                 505                 510

Tyr Pro His Val Glu Pro His Thr His Leu Val His Gln Ala Asn Val
```

```
        515                 520                 525

Leu Leu Ala Leu Gln Leu Leu Leu Glu Asp Arg Glu Phe Val Phe Leu
    530                 535                 540

Gln Lys Tyr Pro His Val Glu Pro His Thr His Leu Val His Gln Ala
545                 550                 555                 560

Asn Val Leu Leu Ala Leu Gln Leu Leu Leu Glu Asp Arg Glu Phe Val
                565                 570                 575

Phe Leu Gln Lys Tyr Pro His Val Glu Pro His Thr His Leu Val His
            580                 585                 590

Gln Ala Asn Val Leu Leu Ala Leu Gln Leu Leu Leu Glu Asp Arg Glu
        595                 600                 605

Phe Val Phe Leu Gln Lys Tyr Pro His Val Glu Pro His Thr His Leu
    610                 615                 620

Val His Gln Ala Asn Val Leu Leu Ala Leu Gln Leu Leu Leu Glu Asp
625                 630                 635                 640

Arg Glu Phe Val Phe Leu Gln Lys Tyr Pro His Val Glu Pro His Thr
                645                 650                 655

His Leu Val His Gln Ala Asn Val Leu Leu Ala Leu Gln Leu Leu Leu
            660                 665                 670

Glu Asp Arg Glu Phe Val Phe Leu Gln Lys Tyr Pro His Val Glu Pro
        675                 680                 685

His Thr His Leu Val His Gln Ala Asn Val Leu Leu Ala Leu Gln Leu
    690                 695                 700

Leu Leu Glu Asp Arg Glu Phe Val Phe Leu Gln Lys Tyr Pro His Val
705                 710                 715                 720

Glu Pro His Thr His Leu Val His Gln Ala Asn Val Leu Leu Ala Leu
                725                 730                 735

Gln Leu Leu Leu Glu Asp Arg Glu Phe Val Phe Leu Gln Lys Tyr Pro
            740                 745                 750

His Val Glu His His His His His His
        755                 760


<210> SEQ ID NO 52
<211> LENGTH: 804
<212> TYPE: PRT
<213> ORGANISM: Artificial sequence
<220> FEATURE:
<223> OTHER INFORMATION: fusion biogenic polypeptide

<400> SEQUENCE: 52

Met Ala Glu Gln Leu Val Asp Leu Trp Asn Glu Cys Ala Lys Ala Cys
1               5                   10                  15

Val Leu Asp Leu Lys Asp Gly Val Arg Ser Ser Arg Met Ser Val Asp
            20                  25                  30

Pro Ala Ile Ala Asp Thr Asn Gly Gln Gly Val Leu His Tyr Cys Met
        35                  40                  45

Glu Phe Ser Ser Phe His Leu Phe His His Leu Pro Ala Arg Ala Pro
    50                  55                  60

Leu Ala Pro Ser Glu Leu Gln Pro Leu Glu His Met Ala Glu Glu Ala
65                  70                  75                  80

Phe Asp Leu Trp Asn Glu Cys Ala Lys Ala Cys Val Leu Asp Leu Lys
                85                  90                  95

Asp Gly Val Arg Ser Ser Arg Met Ser Val Asp Pro Ala Ile Ala Asp
            100                 105                 110

Thr Asn Gly Gln Gly Val Leu His Tyr Ser Met Val Leu Glu Gly Gly
```

-continued

```
        115                 120                 125

Asn Asp Ala Leu Lys Leu Ala Ile Asp Asn Ala Leu Ser Ile Thr Ser
    130                 135                 140

Asp Gly Leu Thr Ile Arg Leu Glu Gly Gly Val Glu Pro Asn Lys Pro
145                 150                 155                 160

Val Arg Tyr Ser Tyr Thr Arg Gln Ala Arg Gly Ser Trp Ser Leu Asn
                165                 170                 175

Trp Leu Val Pro Ile Gly His Glu Lys Pro Ser Asn Ile Lys Val Phe
            180                 185                 190

Ile His Glu Leu Asn Ala Gly Asn Gln Leu Ser His Met Ser Pro Ile
        195                 200                 205

Tyr Thr Ile Glu Met Gly Asp Glu Leu Leu Ala Lys Leu Ala Arg Asp
    210                 215                 220

Ala Thr Phe Phe Val Arg Ala His Glu Ser Asn Glu Met Gln Pro Thr
225                 230                 235                 240

Leu Ala Ile Ser His Ala Gly Val Ser Val Val Met Ala Gln Thr Gln
                245                 250                 255

Pro Arg Arg Glu Lys Arg Trp Ser Glu Trp Ala Ser Gly Lys Val Leu
            260                 265                 270

Cys Leu Leu Asp Pro Leu Asp Gly Val Tyr Asn Tyr Leu Ala Gln Gln
        275                 280                 285

Arg Cys Asn Leu Asp Asp Thr Trp Glu Gly Lys Ile Tyr Arg Val Leu
    290                 295                 300

Ala Gly Asn Pro Ala Lys His Asp Leu Asp Ile Lys Pro Thr Val Ile
305                 310                 315                 320

Ser His Arg Leu His Phe Pro Glu Gly Gly Ser Leu Ala Ala Leu Thr
                325                 330                 335

Ala His Gln Ala Cys His Leu Pro Leu Glu Thr Phe Thr Arg His Arg
            340                 345                 350

Gln Pro Arg Gly Trp Glu Gln Leu Glu Gln Cys Gly Tyr Pro Val Gln
        355                 360                 365

Arg Leu Val Ala Leu Tyr Leu Ala Ala Arg Leu Ser Trp Asn Gln Val
    370                 375                 380

Asp Gln Val Ile Arg Asn Ala Leu Ala Ser Pro Gly Ser Gly Gly Asp
385                 390                 395                 400

Leu Gly Glu Ala Ile Arg Glu Gln Pro Glu Gln Ala Arg Leu Ala Leu
                405                 410                 415

Thr Leu Ala Ala Ala Glu Ser Glu Arg Phe Val Arg Gln Gly Thr Gly
            420                 425                 430

Asn Asp Glu Ala Gly Ala Ala Asn Ala Asp Val Val Ser Leu Thr Cys
        435                 440                 445

Pro Val Ala Ala Gly Glu Cys Ala Gly Pro Ala Asp Ser Gly Asp Ala
    450                 455                 460

Leu Leu Glu Arg Asn Tyr Pro Thr Gly Ala Glu Phe Leu Gly Asp Gly
465                 470                 475                 480

Gly Asp Val Ser Phe Ser Thr Arg Gly Thr Gln Asn Trp Thr Val Glu
                485                 490                 495

Arg Leu Leu Gln Ala Glu Phe Val Ser Phe Ser Thr Gly Gly Ser Gln
            500                 505                 510

Asn Trp Thr Val Glu Arg Leu Leu Gln Ala Glu Phe Cys Ser Thr Ser
        515                 520                 525

Gln Ala Ala Arg Gln Arg Leu Glu Thr Gly Arg Asn Cys Ser Thr Gly
    530                 535                 540
```

Gln Ala Ala Arg Gln Arg Leu Glu Pro Gly Arg Asn Leu Val Leu Cys
545 550 555 560

Leu Thr Ser Gln Ala Ala Gln Gln Arg Leu Glu Pro Gly Gly Asn Cys
565 570 575

Gln Thr Ser Gln Ala Ala His Gln Arg Leu Glu Pro Gly Arg Asn Cys
580 585 590

Arg Thr Ser Gln Ala Ala Ser Gln Arg Leu Glu Pro Gly Arg Asn Cys
595 600 605

Arg Thr Ser Gln Ala Ala His Gln Arg Leu Glu Pro Gly Arg Asn Cys
610 615 620

Ser Thr Arg Gln Ala Ala Gln Gln Arg Leu Glu Pro Gly Arg Asn Leu
625 630 635 640

Leu Cys Pro Thr Ser Gln Ala Ala His Gln Arg Arg Leu Glu Pro Gly
645 650 655

Arg Asn Cys Ser Thr Ser Gln Ala Ala Tyr Gln Arg Leu Glu Pro Gly
660 665 670

Arg Asn Cys Pro Thr Ser Arg Ala Ala Arg Gln Arg Leu Glu Pro Gly
675 680 685

Arg Asn Leu Leu Cys Ser Thr Ser Gln Ala Ala Leu Gln Arg Leu Glu
690 695 700

Pro Gly Arg Asn Leu Cys Pro Thr Ser Gln Ala Ala Lys Gln Arg Leu
705 710 715 720

Glu Pro Gly Arg Asn Leu Val Val Cys Leu Thr Ser Gln Ala Ala Arg
725 730 735

Gln Arg Leu Glu Pro Gly Arg Asn Cys Ser Thr Ser Gln Ala Ala Ser
740 745 750

Gln Arg Leu Glu Pro Gly Arg Asn Cys Pro Thr Ser Gln Ala Ala Arg
755 760 765

Gln Arg Leu Glu Pro Gly Arg Asn Val Leu Leu Leu Cys Leu Thr Ser
770 775 780

Gln Ala Ala His Gln Arg Leu Glu Pro Gly Arg Asn Leu Glu His His
785 790 795 800

His His His His

<210> SEQ ID NO 53
<211> LENGTH: 737
<212> TYPE: PRT
<213> ORGANISM: Artificial sequence
<220> FEATURE:
<223> OTHER INFORMATION: fusion biogenic polypeptide

<400> SEQUENCE: 53

Met Ala Glu Gln Leu Val Asp Leu Trp Asn Glu Cys Ala Lys Ala Cys
1 5 10 15

Val Leu Asp Leu Lys Asp Gly Val Arg Ser Ser Arg Met Ser Val Asp
20 25 30

Pro Ala Ile Ala Asp Thr Asn Gly Gln Gly Val Leu His Tyr Cys Met
35 40 45

Glu Phe Ser Ser Phe His Leu Phe His His Leu Pro Ala Arg Ala Pro
50 55 60

Leu Ala Pro Ser Glu Leu Gln Pro Leu Glu His Met Ala Glu Glu Ala
65 70 75 80

Phe Asp Leu Trp Asn Glu Cys Ala Lys Ala Cys Val Leu Asp Leu Lys
85 90 95

```
Asp Gly Val Arg Ser Ser Arg Met Ser Val Asp Pro Ala Ile Ala Asp
            100                 105                 110

Thr Asn Gly Gln Gly Val Leu His Tyr Ser Met Val Leu Glu Gly Gly
        115                 120                 125

Asn Asp Ala Leu Lys Leu Ala Ile Asp Asn Ala Leu Ser Ile Thr Ser
    130                 135                 140

Asp Gly Leu Thr Ile Arg Leu Glu Gly Gly Val Glu Pro Asn Lys Pro
145                 150                 155                 160

Val Arg Tyr Ser Tyr Thr Arg Gln Ala Arg Gly Ser Trp Ser Leu Asn
                165                 170                 175

Trp Leu Val Pro Ile Gly His Glu Lys Pro Ser Asn Ile Lys Val Phe
            180                 185                 190

Ile His Glu Leu Asn Ala Gly Asn Gln Leu Ser His Met Ser Pro Ile
        195                 200                 205

Tyr Thr Ile Glu Met Gly Asp Glu Leu Leu Ala Lys Leu Ala Arg Asp
    210                 215                 220

Ala Thr Phe Phe Val Arg Ala His Glu Ser Asn Glu Met Gln Pro Thr
225                 230                 235                 240

Leu Ala Ile Ser His Ala Gly Val Ser Val Val Met Ala Gln Thr Gln
                245                 250                 255

Pro Arg Arg Glu Lys Arg Trp Ser Glu Trp Ala Ser Gly Lys Val Leu
            260                 265                 270

Cys Leu Leu Asp Pro Leu Asp Gly Val Tyr Asn Tyr Leu Ala Gln Gln
        275                 280                 285

Arg Cys Asn Leu Asp Asp Thr Trp Glu Gly Lys Ile Tyr Arg Val Leu
    290                 295                 300

Ala Gly Asn Pro Ala Lys His Asp Leu Asp Ile Lys Pro Thr Val Ile
305                 310                 315                 320

Ser His Arg Leu His Phe Pro Glu Gly Gly Ser Leu Ala Ala Leu Thr
                325                 330                 335

Ala His Gln Ala Cys His Leu Pro Leu Glu Thr Phe Thr Arg His Arg
            340                 345                 350

Gln Pro Arg Gly Trp Glu Gln Leu Glu Gln Cys Gly Tyr Pro Val Gln
        355                 360                 365

Arg Leu Val Ala Leu Tyr Leu Ala Ala Arg Leu Ser Trp Asn Gln Val
    370                 375                 380

Asp Gln Val Ile Arg Asn Ala Leu Ala Ser Pro Gly Ser Gly Gly Asp
385                 390                 395                 400

Leu Gly Glu Ala Ile Arg Glu Gln Pro Glu Gln Ala Arg Leu Ala Leu
                405                 410                 415

Thr Leu Ala Ala Ala Glu Ser Glu Arg Phe Val Arg Gln Gly Thr Gly
            420                 425                 430

Asn Asp Glu Ala Gly Ala Ala Asn Ala Asp Val Val Ser Leu Thr Cys
        435                 440                 445

Pro Val Ala Ala Gly Glu Cys Ala Gly Pro Ala Asp Ser Gly Asp Ala
    450                 455                 460

Leu Leu Glu Arg Asn Tyr Pro Thr Gly Ala Glu Phe Leu Gly Asp Gly
465                 470                 475                 480

Gly Asp Val Ser Phe Ser Thr Arg Gly Thr Gln Asn Trp Thr Val Glu
                485                 490                 495

Arg Leu Leu Gln Ala Glu Phe Gly Val Ser Ala Ala Gln Glu Lys Ile
            500                 505                 510

Ser Phe Gly Leu Leu Gly Val Pro Thr Ala Gln Glu Thr Thr Ser Ile
```

515 520 525

Arg Glu Val Leu Glu Val Ser Thr Ala Gln Glu Asn Ser Pro Phe Met
530 535 540

Leu Gly Ala Ser Ala Thr Glu Glu Lys Thr Ser Leu Arg Leu Gly Ala
545 550 555 560

Ser Thr Thr Gln Glu Thr Ser Phe Gly Lys Cys Leu Arg Pro His Gly
565 570 575

Val Ser Ala Ala Gln Gly Thr Thr Pro Phe Arg Gly Val Ser Thr Thr
580 585 590

Gln Glu Asn Thr Ser Phe Gly Arg Val Pro Thr Ala Gln Glu Asn Val
595 600 605

Ser Phe Gly Leu His Gly Val Pro Ala Ala Gln Lys Thr Asn Ser Phe
610 615 620

Gly Gly Val Pro Thr Ala Gln Glu Asn Ile Ser Phe Lys Glu Val Ser
625 630 635 640

Ala Thr Gln Arg Glu Ile Pro Phe Arg Cys Leu Arg Pro His Gly Val
645 650 655

Ser Thr Ala Gln Glu Thr Pro Phe Arg Gly Val Ser Thr Ala Gln Glu
660 665 670

Thr Ile Pro Phe Arg Gly Val Ser Ala Thr His Glu Asn Ile Ser Phe
675 680 685

Gly Cys Leu Arg Pro His Gly Val Ser Ala Ala Gln Glu Ser Ile Pro
690 695 700

Ile Arg Leu Gly Ala Ser Ala Ala Gln Glu Asn Thr Ser Phe Arg Gly
705 710 715 720

Thr Pro Ala Ala Gln Glu Lys Ile Pro Leu Glu His His His His His
725 730 735

His

<210> SEQ ID NO 54
<211> LENGTH: 796
<212> TYPE: PRT
<213> ORGANISM: Artificial sequence
<220> FEATURE:
<223> OTHER INFORMATION: fusion biogenic polypeptide

<400> SEQUENCE: 54

Met Ala Glu Gln Leu Val Asp Leu Trp Asn Glu Cys Ala Lys Ala Cys
1 5 10 15

Val Leu Asp Leu Lys Asp Gly Val Arg Ser Ser Arg Met Ser Val Asp
20 25 30

Pro Ala Ile Ala Asp Thr Asn Gly Gln Gly Val Leu His Tyr Cys Met
35 40 45

Glu Phe Ser Ser Phe His Leu Phe His His Leu Pro Ala Arg Ala Pro
50 55 60

Leu Ala Pro Ser Glu Leu Gln Pro Leu Glu His Met Ala Glu Glu Ala
65 70 75 80

Phe Asp Leu Trp Asn Glu Cys Ala Lys Ala Cys Val Leu Asp Leu Lys
85 90 95

Asp Gly Val Arg Ser Ser Arg Met Ser Val Asp Pro Ala Ile Ala Asp
100 105 110

Thr Asn Gly Gln Gly Val Leu His Tyr Ser Met Val Leu Glu Gly Gly
115 120 125

Asn Asp Ala Leu Lys Leu Ala Ile Asp Asn Ala Leu Ser Ile Thr Ser
130 135 140

```
Asp Gly Leu Thr Ile Arg Leu Glu Gly Gly Val Glu Pro Asn Lys Pro
145                 150                 155                 160

Val Arg Tyr Ser Tyr Thr Arg Gln Ala Arg Gly Ser Trp Ser Leu Asn
                165                 170                 175

Trp Leu Val Pro Ile Gly His Glu Lys Pro Ser Asn Ile Lys Val Phe
            180                 185                 190

Ile His Glu Leu Asn Ala Gly Asn Gln Leu Ser His Met Ser Pro Ile
        195                 200                 205

Tyr Thr Ile Glu Met Gly Asp Glu Leu Leu Ala Lys Leu Ala Arg Asp
    210                 215                 220

Ala Thr Phe Phe Val Arg Ala His Glu Ser Asn Glu Met Gln Pro Thr
225                 230                 235                 240

Leu Ala Ile Ser His Ala Gly Val Ser Val Val Met Ala Gln Thr Gln
                245                 250                 255

Pro Arg Arg Glu Lys Arg Trp Ser Glu Trp Ala Ser Gly Lys Val Leu
            260                 265                 270

Cys Leu Leu Asp Pro Leu Asp Gly Val Tyr Asn Tyr Leu Ala Gln Gln
        275                 280                 285

Arg Cys Asn Leu Asp Asp Thr Trp Glu Gly Lys Ile Tyr Arg Val Leu
    290                 295                 300

Ala Gly Asn Pro Ala Lys His Asp Leu Asp Ile Lys Pro Thr Val Ile
305                 310                 315                 320

Ser His Arg Leu His Phe Pro Glu Gly Gly Ser Leu Ala Ala Leu Thr
                325                 330                 335

Ala His Gln Ala Cys His Leu Pro Leu Glu Thr Phe Thr Arg His Arg
            340                 345                 350

Gln Pro Arg Gly Trp Glu Gln Leu Glu Gln Cys Gly Tyr Pro Val Gln
        355                 360                 365

Arg Leu Val Ala Leu Tyr Leu Ala Ala Arg Leu Ser Trp Asn Gln Val
    370                 375                 380

Asp Gln Val Ile Arg Asn Ala Leu Ala Ser Pro Gly Ser Gly Gly Asp
385                 390                 395                 400

Leu Gly Glu Ala Ile Arg Glu Gln Pro Glu Gln Ala Arg Leu Ala Leu
                405                 410                 415

Thr Leu Ala Ala Ala Glu Ser Glu Arg Phe Val Arg Gln Gly Thr Gly
            420                 425                 430

Asn Asp Glu Ala Gly Ala Ala Asn Ala Asp Val Val Ser Leu Thr Cys
        435                 440                 445

Pro Val Ala Ala Gly Glu Cys Ala Gly Pro Ala Asp Ser Gly Asp Ala
    450                 455                 460

Leu Leu Glu Arg Asn Tyr Pro Thr Gly Ala Glu Phe Leu Gly Asp Gly
465                 470                 475                 480

Gly Asp Val Ser Phe Ser Thr Arg Gly Thr Gln Asn Trp Thr Val Glu
                485                 490                 495

Arg Leu Leu Gln Ala Glu Phe Leu Gly Val Ser Ala Ala Gln Glu Arg
            500                 505                 510

Ile Pro Ile Arg Glu Val Ser Ala Asp Lys Glu Val Ser Ala Glu Lys
        515                 520                 525

Lys Glu Ile Ser Phe Gly Val Ser Thr Ala Gln Gly Asn Ile Ser Phe
    530                 535                 540

Gly Leu Gly Val Ser Thr Ala Gln Glu Ala Ile Pro Phe Leu Ala Leu
545                 550                 555                 560
```

-continued

```
Gly Val Ser Thr Ala Gln Glu Thr Ile Pro Phe Gly Leu Leu Gly Val
                565                 570                 575

Ser Thr Ala Gln Gly Ile Ile Ser Phe Gly Gly Val Ser Thr Ala Gln
            580                 585                 590

Glu Asn Ile Ser Phe Gly Gly Val Ser Thr Ala Gln Glu Thr Ile Ser
        595                 600                 605

Phe Gly Leu Leu Gly Val Ser Thr Ala Gln Glu Asn Ile Ser Phe Gly
    610                 615                 620

Cys Leu Arg Thr His Glu Val Ser Ala Ala Gln Glu Lys Ile Ser Phe
625                 630                 635                 640

Gly Gly Val Ser Glu Ala Gln Lys Ile Ser Phe Gly Val Ser Ala Ala
                645                 650                 655

Gly Val Ser Ala Ala Gln Glu Glu Ile Pro Phe Gly Cys Leu Arg Pro
            660                 665                 670

His Gly Leu Pro Ala Ala Gln Glu Lys Thr Ser Phe Gly Gly Val Ser
        675                 680                 685

Ala Ala Gln Glu Lys Thr Ser Phe Gly Gly Val Ser Ala Ala Gln Glu
    690                 695                 700

Glu Phe Ser Phe Gly Cys Leu Arg Pro His Arg Val Ser Ala Ala Gln
705                 710                 715                 720

Glu Lys Ile Ser Phe Glu Val Ser Ala Leu Glu Val Ser Ala Ala Gln
                725                 730                 735

Glu Lys Ile Ser Phe Gly Val Ser Ala Ala Leu Gly Val Ser Ala Ala
            740                 745                 750

Gln Glu Lys Asn Ser Phe Gly Cys Leu Arg Pro His Gly Val Ser Ala
        755                 760                 765

Ala Gln Glu Lys Thr Ser Phe Gly Gly Val Ser Ala Ala Gln Lys Lys
    770                 775                 780

Ile Ser Phe Gly Leu Glu His His His His His His
785                 790                 795
```

<210> SEQ ID NO 55
<211> LENGTH: 48
<212> TYPE: DNA
<213> ORGANISM: Artificial sequence
<220> FEATURE:
<223> OTHER INFORMATION: primer

<400> SEQUENCE: 55
gttgacccgg ttggtccgtc cgacccgtcc atcgtttccc tggttgaa 48

<210> SEQ ID NO 56
<211> LENGTH: 49
<212> TYPE: DNA
<213> ORGANISM: Artificial sequence
<220> FEATURE:
<223> OTHER INFORMATION: primer

<400> SEQUENCE: 56
aggtcggagc accagcgtcg atgaaggagg tttcttcaac cagggaaac 49

<210> SEQ ID NO 57
<211> LENGTH: 48
<212> TYPE: DNA
<213> ORGANISM: Artificial sequence
<220> FEATURE:
<223> OTHER INFORMATION: primer

<400> SEQUENCE: 57

-continued gacaccctgg ctccggttcg tccgccgctg accgttgacc cggttggt 48

<210> SEQ ID NO 58
<211> LENGTH: 48
<212> TYPE: DNA
<213> ORGANISM: Artificial sequence
<220> FEATURE:
<223> OTHER INFORMATION: primer

<400> SEQUENCE: 58
accggaaacg tccggcggga tggacggaac ggaggtcgga gcaccagc 48

<210> SEQ ID NO 59
<211> LENGTH: 51
<212> TYPE: DNA
<213> ORGANISM: Artificial sequence
<220> FEATURE:
<223> OTHER INFORMATION: primer

<400> SEQUENCE: 59
tacatcccgc tgggtacccg tccgccgacc gctaccgaca ccctggctcc g 51

<210> SEQ ID NO 60
<211> LENGTH: 51
<212> TYPE: DNA
<213> ORGANISM: Artificial sequence
<220> FEATURE:
<223> OTHER INFORMATION: primer

<400> SEQUENCE: 60
agccggggta gtgtcggtgg aggtggtgat ggagaaaccg gaaacgtccg g 51

<210> SEQ ID NO 61
<211> LENGTH: 48
<212> TYPE: DNA
<213> ORGANISM: Artificial sequence
<220> FEATURE:
<223> OTHER INFORMATION: primer

<400> SEQUENCE: 61
ggtaccggtt ccggtactgg cggtcgtacc ggttacatcc cgctgggt 48

<210> SEQ ID NO 62
<211> LENGTH: 51
<212> TYPE: DNA
<213> ORGANISM: Artificial sequence
<220> FEATURE:
<223> OTHER INFORMATION: primer

<400> SEQUENCE: 62
tacggtagta acggtgttgt tgttgatgtc caggatagcc ggggtagtgt c 51

<210> SEQ ID NO 63
<211> LENGTH: 51
<212> TYPE: DNA
<213> ORGANISM: Artificial sequence
<220> FEATURE:
<223> OTHER INFORMATION: primer

<400> SEQUENCE: 63
ggttctatgg gtgttttctt cggcggtctg ggcatcggta ccggttccgg t 51

<210> SEQ ID NO 64
<211> LENGTH: 48
<212> TYPE: DNA
<213> ORGANISM: Artificial sequence
<220> FEATURE:
<223> OTHER INFORMATION: primer

<400> SEQUENCE: 64
cgggtcggtg aaggtcgggt tgttgtgagt ggttacggta gtaacggt 48

<210> SEQ ID NO 65
<211> LENGTH: 48
<212> TYPE: DNA
<213> ORGANISM: Artificial sequence
<220> FEATURE:
<223> OTHER INFORMATION: primer

<400> SEQUENCE: 65
ggtaaaacca tcgctgaaca gatcctgcaa tacggttcta tgggtgtt 48

<210> SEQ ID NO 66
<211> LENGTH: 48
<212> TYPE: DNA
<213> ORGANISM: Artificial sequence
<220> FEATURE:
<223> OTHER INFORMATION: primer

<400> SEQUENCE: 66
ggtttcagcc ggggtcggcg gttgcagaac ggacgggtcg gtgaaggt 48

<210> SEQ ID NO 67
<211> LENGTH: 51
<212> TYPE: DNA
<213> ORGANISM: Artificial sequence
<220> FEATURE:
<223> OTHER INFORMATION: primer

<400> SEQUENCE: 67
ggtacctgcc cgccggacat catcccgaaa gttgaaggta aaaccatcgc t 51

<210> SEQ ID NO 68
<211> LENGTH: 51
<212> TYPE: DNA
<213> ORGANISM: Artificial sequence
<220> FEATURE:
<223> OTHER INFORMATION: primer

<400> SEQUENCE: 68
ggagatggtg gaagaggaca gggtgaagtg accaccggtt tcagccgggg t 51

<210> SEQ ID NO 69
<211> LENGTH: 45
<212> TYPE: DNA
<213> ORGANISM: Artificial sequence
<220> FEATURE:
<223> OTHER INFORMATION: primer

<400> SEQUENCE: 69
acccagctgt acaaaacctg caaacaggct ggtacctgcc cgccg 45

<210> SEQ ID NO 70
<211> LENGTH: 45
<212> TYPE: DNA
<213> ORGANISM: Artificial sequence
<220> FEATURE:
<223> OTHER INFORMATION: primer

<400> SEQUENCE: 70
gtccatcggg atttcttcgt agttgtgggt ggagatggtg gaaga 45

<210> SEQ ID NO 71
<211> LENGTH: 47
<212> TYPE: DNA
<213> ORGANISM: Artificial sequence
<220> FEATURE:
<223> OTHER INFORMATION: primer

<400> SEQUENCE: 71
ccgtgctaaa cgtcgtaaac gtgcttccgc tacccagctg tacaaaa 47

<210> SEQ ID NO 72
<211> LENGTH: 48
<212> TYPE: DNA
<213> ORGANISM: Artificial sequence
<220> FEATURE:
<223> OTHER INFORMATION: primer

<400> SEQUENCE: 72
attatttttc tcgagcagtt cgtctttggt gtccatcggg atttcttc 48

<210> SEQ ID NO 73
<211> LENGTH: 48
<212> TYPE: DNA
<213> ORGANISM: Artificial sequence
<220> FEATURE:
<223> OTHER INFORMATION: primer

<400> SEQUENCE: 73
cccgaattcc atatggtcga cggtatgtcc atccgtgcta aacgtcgt 48

<210> SEQ ID NO 74
<211> LENGTH: 48
<212> TYPE: DNA
<213> ORGANISM: Artificial sequence
<220> FEATURE:
<223> OTHER INFORMATION: primer

<400> SEQUENCE: 74
attatttttc tcgagcagtt cgtctttggt gtccatcggg atttcttc 48

<210> SEQ ID NO 75
<211> LENGTH: 21
<212> TYPE: DNA
<213> ORGANISM: Artificial sequence
<220> FEATURE:
<223> OTHER INFORMATION: primer

<400> SEQUENCE: 75
ccccatatgg ccgaagaagc t 21

<210> SEQ ID NO 76
<211> LENGTH: 49
<212> TYPE: DNA
<213> ORGANISM: Artificial sequence
<220> FEATURE:
<223> OTHER INFORMATION: primer

<400> SEQUENCE: 76
tttctcgagt tgaattccat ggagtagttc atcactccct ggccgttgg 49

<210> SEQ ID NO 77
<211> LENGTH: 21
<212> TYPE: DNA
<213> ORGANISM: Artificial sequence
<220> FEATURE:
<223> OTHER INFORMATION: primer -continued

```
<400> SEQUENCE: 77

ccccatatgg ccgaagaagc t                                              21


<210> SEQ ID NO 78
<211> LENGTH: 44
<212> TYPE: DNA
<213> ORGANISM: Artificial sequence
<220> FEATURE:
<223> OTHER INFORMATION: primer

<400> SEQUENCE: 78

tttctcgagg aattcgacgt cgccgccgtc gccgaggaac tccg                     44


<210> SEQ ID NO 79
<211> LENGTH: 21
<212> TYPE: DNA
<213> ORGANISM: Artificial sequence
<220> FEATURE:
<223> OTHER INFORMATION: primer

<400> SEQUENCE: 79

ccccatatgg ccgaagaagc t                                              21


<210> SEQ ID NO 80
<211> LENGTH: 38
<212> TYPE: DNA
<213> ORGANISM: Artificial sequence
<220> FEATURE:
<223> OTHER INFORMATION: primer

<400> SEQUENCE: 80

tttctcgagg aattccgcct ggagcagccg ctccaccg                            38


<210> SEQ ID NO 81
<211> LENGTH: 30
<212> TYPE: DNA
<213> ORGANISM: Artificial sequence
<220> FEATURE:
<223> OTHER INFORMATION: primer

<400> SEQUENCE: 81

tataccatgg ccgaacaatt ggtggacctc                                     30


<210> SEQ ID NO 82
<211> LENGTH: 40
<212> TYPE: DNA
<213> ORGANISM: Artificial sequence
<220> FEATURE:
<223> OTHER INFORMATION: primer

<400> SEQUENCE: 82

tttctcgagg aattcttcca tgcagtagtg cagcacgccc                          40
```